United States Patent
Shin et al.

(10) Patent No.: US 9,525,515 B2
(45) Date of Patent: Dec. 20, 2016

(54) APPARATUS AND METHOD FOR SENDING AND RECEIVING BROADCAST SIGNALS

(71) Applicant: LG ELECTRONICS INC., Seoul (KR)

(72) Inventors: Jongwoong Shin, Seoul (KR); Jinwoo Kim, Seoul (KR); Woosuk Ko, Seoul (KR); Sungryong Hong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 14/841,957

(22) Filed: Sep. 1, 2015

(65) Prior Publication Data

US 2016/0149682 A1 May 26, 2016

Related U.S. Application Data

(60) Provisional application No. 62/085,227, filed on Nov. 26, 2014, provisional application No. 62/112,134, filed on Feb. 4, 2015.

(51) Int. Cl.

| | |
|---|---|
| H04L 1/00 | (2006.01) |
| H04L 12/18 | (2006.01) |
| H04L 5/00 | (2006.01) |
| H04W 4/06 | (2009.01) |
| H03M 13/11 | (2006.01) |
| H03M 13/25 | (2006.01) |
| H03M 13/27 | (2006.01) |
| H03M 13/29 | (2006.01) |
| H03M 13/00 | (2006.01) |

(Continued)

(52) U.S. Cl.
CPC ........ *H04L 1/0057* (2013.01); *H03M 13/1165* (2013.01); *H03M 13/255* (2013.01); *H03M 13/271* (2013.01); *H03M 13/2778* (2013.01); *H03M 13/2906* (2013.01); *H03M 13/6356* (2013.01); *H03M 13/6362* (2013.01); *H04L 1/0041* (2013.01); *H04L 1/0071* (2013.01); *H04L 5/0053* (2013.01); *H04L 12/18* (2013.01); *H04W 4/06* (2013.01); *H03M 13/09* (2013.01); *H03M 13/152* (2013.01)

(58) Field of Classification Search
USPC ........ 375/260, 136, 135; 370/329, 338, 474
See application file for complete search history.

(56) References Cited

U.S. PATENT DOCUMENTS

| | | | | |
|---|---|---|---|---|
| 2010/0303130 | A1* | 12/2010 | Moh | H04L 27/2628 375/135 |
| 2011/0231725 | A1* | 9/2011 | Gotman | H04L 1/1845 714/748 |

(Continued)

FOREIGN PATENT DOCUMENTS

| | | |
|---|---|---|
| WO | WO 2008/069492 A1 | 6/2008 |
| WO | WO 2011/062444 A2 | 5/2011 |

(Continued)

*Primary Examiner* — Eva Puente
(74) *Attorney, Agent, or Firm* — Birch, Stewart, Kolasch & Birch, LLP

(57) ABSTRACT

A broadcast signal receiver is disclosed. A broadcast signal receiver according to an embodiment of the present invention comprises a constellation mapper for symbol-demapping by using the signaling information as LLR values; a bit deinterleaver for bit multiplexing and block deinterleaving of the signaling information; an FEC decoder for FEC decoding the signaling information; and a descrambler for descrambling the signaling information.

14 Claims, 36 Drawing Sheets

(51) Int. Cl.
*H03M 13/15* (2006.01)
*H03M 13/09* (2006.01)

(56) References Cited

U.S. PATENT DOCUMENTS

| | | | |
|---|---|---|---|
| 2012/0243600 A1 | 9/2012 | Jeong et al. | |
| 2014/0010243 A1* | 1/2014 | Yu | H04L 1/0041 |
| | | | 370/474 |
| 2014/0314063 A1* | 10/2014 | Yu | H04W 84/12 |
| | | | 370/338 |
| 2015/0256295 A1* | 9/2015 | Nammi | H04L 1/1845 |
| | | | 370/329 |

FOREIGN PATENT DOCUMENTS

| | | |
|---|---|---|
| WO | WO 2013/109113 A1 | 7/2013 |
| WO | WO 2014/148785 A1 | 9/2014 |

* cited by examiner

FIG.12

| Content | Bits |
|---|---|
| PHY_PROFILE | 3 |
| FFT_SIZE | 2 |
| GI_FRACTION | 3 |
| EAC_FLAG | 1 |
| PQLOT_MODE | 1 |
| PAPR_FLAG | 1 |
| FRU_CONFIGURE | 3 |
| RESERVED | 7 |

FIG.14

| Content | Bit |
|---|---|
| FIC_FLAG | 1 |
| AUX_FLAG | 1 |
| NUM_DP | 6 |
| for i = NUM_DP | |
| DP_ID | 6 |
| DP_TYPE | 3 |
| DP_GROUP_ID | 8 |
| BASE_DP_ID | 6 |
| DP_FEC_TYPE | 2 |
| DP_COD | 4 |
| DP_MOD | 4 |
| DP_SSD_FLAG | 1 |
| if PHY_PROFILE = '010' | |
| DP_MIMO | 3 |
| end | |
| DP_TI_TYPE | 1 |
| DP_TI_LENGTH | 2 |
| DP_TI_BYPASS | 1 |
| DP_FRAME_INTERVAL | 2 |
| DP_FIRST_FRAME_IDX | 5 |
| DP_NUM_BLOCK_MAX | 10 |
| DP_PAYLOAD_TYPE | 2 |
| DP_INBAND_MODE | 2 |
| DP_PROTOCAL_TYPE | 2 |
| DP_CRC_MODE | 2 |

| Content | Bit |
|---|---|
| if DP_PAYLOAD_TYPE==TS('00') | |
| DNP_MODE | 2 |
| ISSY_MODE | 2 |
| HC_MODE_TS | 2 |
| if HC_MODE_TS=='01' or '10' | |
| PID | 13 |
| end | |
| if DP_PAYLOAD_TYPE==IP('01') | |
| HC_MODE_IP | 2 |
| end | |
| RESERVED | 8 |
| end | |
| if FIC_FLAG == 1 | |
| FIC_VERSION | 8 |
| FIC_LENGTH_BYTE | 13 |
| RESERVED | 8 |
| end | |
| if AUX_FLAG == 1 | |
| NUM_AUX | 4 |
| AUX_CONFIG_RFU | 8 |
| for i=1:NUM_AUX | |
| AUX_STREAM_TYPE | 4 |
| AUX_PRIVATE_CONF | 28 |
| end | |
| end | |

FIG. 15

| Content | Bit |
|---|---|
| FRAME_INDEX | 5 |
| PLS_CHANGE_COUNTER | 4 |
| FIC_CHANGE_COUNTER | 4 |
| RESERVED | 16 |
| for i = 1:NUM_DP | |
|   DP_ID | 6 |
|   DP_START | 15 (or 13) |
|   DP_NUM_BLOCK | 10 |
|   RESERVED | 8 |
| end | |
| EAC_FLAG | 1 |
| EAS_WAKE_UP_VERSION_NUM | 8 |
| if EAC_FLAG == 1 | |
|   EAC_LENGTH_BYTE | 12 |
| else   EAC_COUNTER | 12 |
| end | |
| for i = 1:NUM_AUX | |
|   AUX_PRIVATE_DYN | 48 |
| end | |
| CRC 32 | 32 |

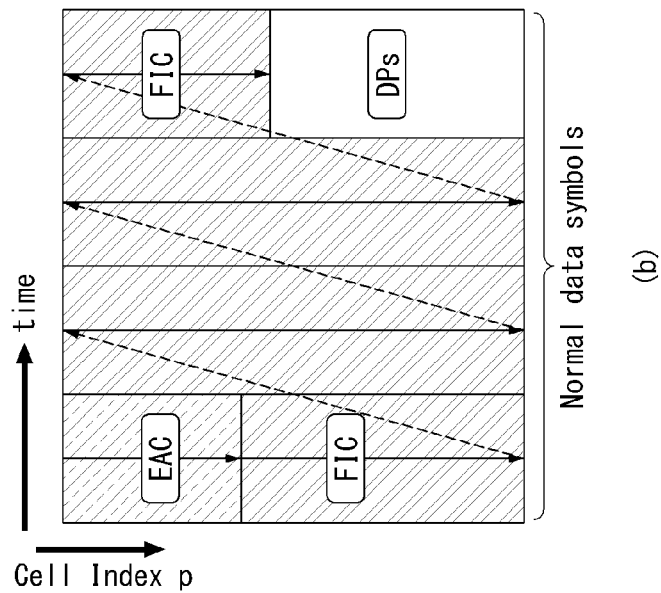
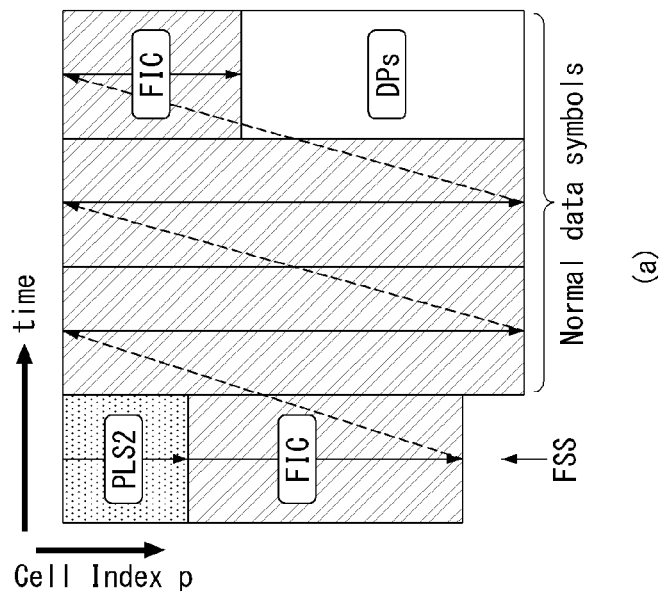
FIG.19

APPARATUS AND METHOD FOR SENDING AND RECEIVING BROADCAST SIGNALS

CROSS-REFERENCE TO RELATED APPLICATIONS

This application claims the benefit under 35 U.S.C. §119 (e) to U.S. Provisional Application No. 62/085,227 filed on Nov. 26, 2014, and to U.S. Provisional Application No. 62/112,134 filed on Feb. 4, 2015. The entire contents of all these applications are hereby incorporated by reference in its entirety.

BACKGROUND OF THE INVENTION

Field of the Invention

The present invention relates to an apparatus for transmitting broadcast signals, an apparatus for receiving broadcast signals and methods for transmitting and receiving broadcast signals.

Discussion of the Related Art

As analog broadcast signal transmission comes to an end, various technologies for transmitting/receiving digital broadcast signals are being developed. A digital broadcast signal may include a larger amount of video/audio data than an analog broadcast signal and further include various types of additional data in addition to the video/audio data.

That is, a digital broadcast system can provide HD (high definition) images, multi-channel audio and various additional services. However, data transmission efficiency for transmission of large amounts of data, robustness of transmission/reception networks and network flexibility in consideration of mobile reception equipment need to be improved for digital broadcast.

SUMMARY OF THE INVENTION

To solve the technical problem above, a broadcast signal receiver for processing a broadcast signal including signaling information according to an embodiment of the present invention comprises a constellation mapper for symbol-demapping by using the signaling information as log-likelihood ratio (LLR) values; a bit deinterleaver for bit multiplexing and block deinterleaving of the signaling information; a forward error correction (FEC) decoder for FEC decoding the signaling information; and a descrambler for descrambling the signaling information, wherein the FEC decoder further comprises a zero inserting/parity inserting unit for inserting shortened zero bits and punctured parity bits into the signaling information; a low-density parity-check (LDPC) decoder for LDPC decoding the signaling information; and a Bose-Chaudhuri-Hochquenghem (BCH) decoder for removing zero bits of the signaling information and BCH decoding the signaling information.

In a broadcast signal receiver according to an embodiment of the present invention, the zero inserting and parity inserting unit inserts LLRs of infinite values as the zero bits, and inserts LLRs of zero values as the parity bits.

In a broadcast signal receiver according to an embodiment of the present invention, parity bits included in the signaling information are split into at least one of bit group units and permuted on the basis of the bit group units.

In a broadcast signal receiver according to an embodiment of the present invention, the zero inserting and parity inserting unit inserts LLRs of zero values into the positions of punctured, last parity bits among the permuted parity bits of bit group units.

In a broadcast signal receiver according to an embodiment of the present invention, the signaling information is characterized such that the zero bits are padded in bit group units according to a shortening pattern order and the BCH encoded signaling information is padded sequentially into the bit positions which are not padded with the zero bits.

In a broadcast signal receiver according to an embodiment of the present invention, the zero bits are padded to fill up the LDPC information bits in case the number of BCH encoded bits is smaller than the number of LDPC information bits.

In a broadcast signal receiver according to an embodiment of the present invention, the signaling information includes information for configuring physical layer parameters, layer 1 (L1) static information with a fixed length, and L1 dynamic information with a variable length.

A method for receiving a broadcast signal according to an embodiment of the present invention comprises performing symbol-demapping of the signaling information to LLR values; performing bit multiplexing and block interleaving on the signaling information; FEC decoding the signaling information; and descrambling the signaling information, wherein the FEC decoding further comprises inserting shortened zero bits and punctured parity bits into the signaling information; LDPC decoding the signaling information; and removing zero bits of the signaling information and BCH decoding the signaling information.

In a method for receiving a broadcast signal according to an embodiment of the present invention, the inserting zero bits and parity bits inserts LLRs of infinite values as the zero bits and LLRs of zero values as the parity bits.

In a method for receiving a broadcast signal according to an embodiment of the present invention, parity bits included in the signaling information are split into at least one of bit group units and permuted on the basis of the bit group units.

In a method for receiving a broadcast signal according to an embodiment of the present invention, the inserting zero bits and parity bits inserts LLRs of zero values into the positions of punctured, last parity bits among the permuted parity bits of bit group units.

In a method for receiving a broadcast signal according to an embodiment of the present invention, the signaling information is characterized such that the zero bits are padded in bit group units according to a shortening pattern order and the BCH encoded signaling information is padded sequentially into the bit positions which are not padded with the zero bits.

In a method for receiving a broadcast signal according to an embodiment of the present invention, the zero bits are padded to fill up the LDPC information bits in case the number of BCH encoded bits is smaller than the number of LDPC information bits.

In a method for receiving a broadcast signal according to an embodiment of the present invention, the signaling information includes information for configuring physical layer parameters, L1 static information with a fixed length, and L1 dynamic information with a variable length.

The present invention can process data according to service characteristics to control QoS (Quality of Services) for each service or service component, thereby providing various broadcast services.

The present invention can achieve transmission flexibility by transmitting various broadcast services through the same RF signal bandwidth.

The present invention can improve data transmission efficiency and increase robustness of transmission/reception of broadcast signals using a MIMO system.

According to the present invention, it is possible to provide broadcast signal transmission and reception methods and apparatus capable of receiving digital broadcast signals without error even with mobile reception equipment or in an indoor environment.

Further aspects and effects of the present invention will be described more detail with embodiments in belows.

BRIEF DESCRIPTION OF THE DRAWINGS

FIG. 12 illustrates preamble signaling data according to an embodiment of the present invention.

FIG. 14 illustrates PLS2 data according to an embodiment of the present invention.

FIG. 15 illustrates PLS2 data according to another embodiment of the present invention.

FIG. 19 illustrates FIC mapping according to an embodiment of the present invention.

DETAILED DESCRIPTION OF THE EMBODIMENTS

Figure 1:
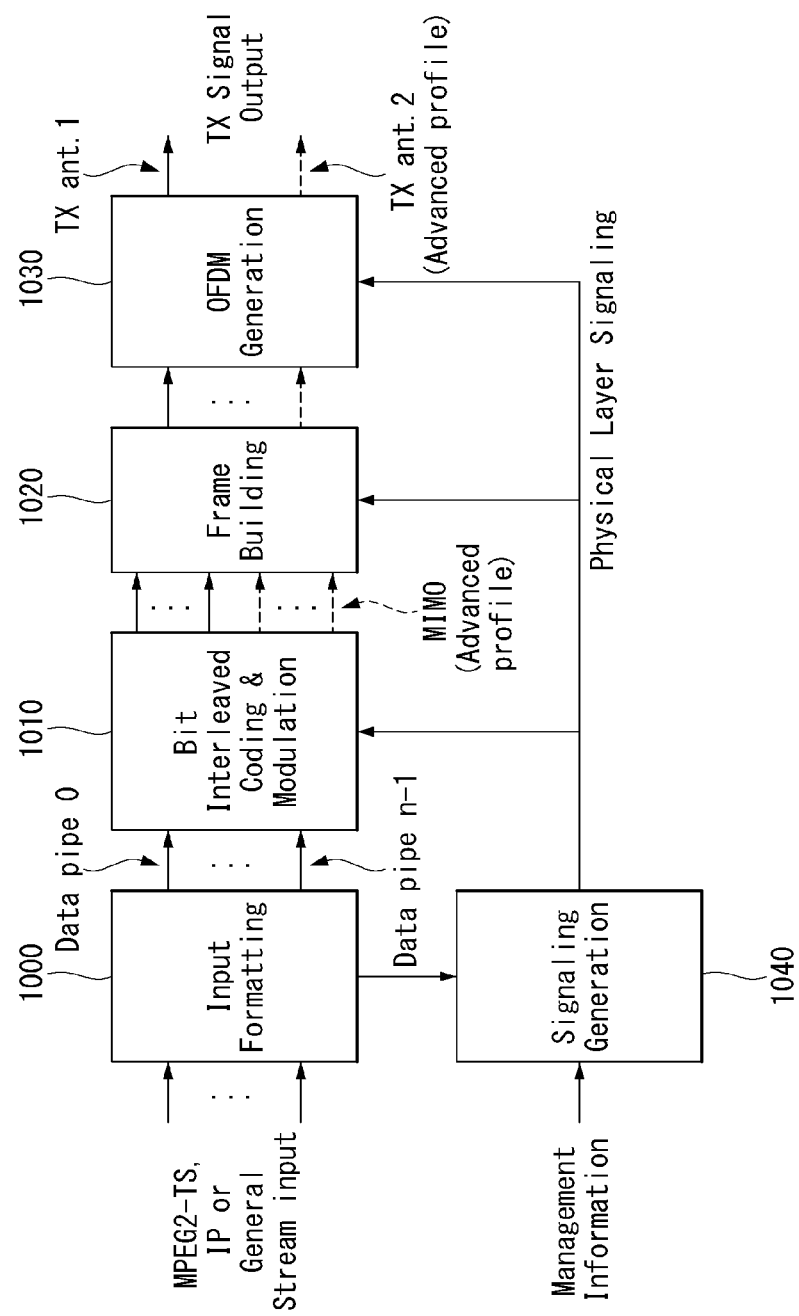
FIG. 1 illustrates a structure of an apparatus for transmitting broadcast signals for future broadcast services according to an embodiment of the present invention.

Reference will now be made in detail to the preferred embodiments of the present invention, examples of which are illustrated in the accompanying drawings. The detailed description, which will be given below with reference to the accompanying drawings, is intended to explain exemplary embodiments of the present invention, rather than to show the only embodiments that can be implemented according to the present invention. The following detailed description includes specific details in order to provide a thorough understanding of the present invention. However, it will be apparent to those skilled in the art that the present invention may be practiced without such specific details.

Although most terms used in the present invention have been selected from general ones widely used in the art, some terms have been arbitrarily selected by the applicant and their meanings are explained in detail in the following description as needed. Thus, the present invention should be understood based upon the intended meanings of the terms rather than their simple names or meanings. Also, the term block and module are used similarly to indicate logical/functional unit of particular signal/data processing.

The present invention provides apparatuses and methods for transmitting and receiving broadcast signals for future broadcast services. Future broadcast services according to an embodiment of the present invention include a terrestrial broadcast service, a mobile broadcast service, a UHDTV service, etc. The present invention may process broadcast signals for the future broadcast services through non-MIMO (Multiple Input Multiple Output) or MIMO according to one embodiment. A non-MIMO scheme according to an embodiment of the present invention may include a MISO (Multiple Input Single Output) scheme, a SISO (Single Input Single Output) scheme, etc.

While MISO or MIMO uses two antennas in the following for convenience of description, the present invention is applicable to systems using two or more antennas.

The present invention may defines three physical layer (PL) profiles—base, handheld and advanced profiles—each optimized to minimize receiver complexity while attaining the performance required for a particular use case. The physical layer (PHY) profiles are subsets of all configurations that a corresponding receiver should implement.

The three PHY profiles share most of the functional blocks but differ slightly in specific blocks and/or parameters. Additional PHY profiles can be defined in the future. For the system evolution, future profiles can also be multiplexed with the existing profiles in a single RF channel through a future extension frame (FEF). The details of each PHY profile are described below.

1. Base Profile

The base profile represents a main use case for fixed receiving devices that are usually connected to a roof-top antenna. The base profile also includes portable devices that could be transported to a place but belong to a relatively stationary reception category. Use of the base profile could be extended to handheld devices or even vehicular by some improved implementations, but those use cases are not expected for the base profile receiver operation.

Target SNR range of reception is from approximately 10 to 20 dB, which includes the 15 dB SNR reception capability of the existing broadcast system (e.g. ATSC A/53). The receiver complexity and power consumption is not as critical as in the battery-operated handheld devices, which will use the handheld profile. Key system parameters for the base profile are listed in below table 1.

TABLE 1

| | |
|---|---|
| LDPC codeword length | 16K, 64K bits |
| Constellation size | 4~10 bpcu (bits per channel use) |
| Time de-interleaving memory size | ≤$2^{19}$ data cells |
| Pilot patterns | Pilot pattern for fixed reception |
| FFT size | 16K, 32K points |

2. Handheld Profile

The handheld profile is designed for use in handheld and vehicular devices that operate with battery power. The devices can be moving with pedestrian or vehicle speed. The power consumption as well as the receiver complexity is very important for the implementation of the devices of the handheld profile. The target SNR range of the handheld profile is approximately 0 to 10 dB, but can be configured to reach below 0 dB when intended for deeper indoor reception.

In addition to low SNR capability, resilience to the Doppler Effect caused by receiver mobility is the most important performance attribute of the handheld profile.

Key system parameters for the handheld profile are listed in the below table 2.

TABLE 2

| | |
|---|---|
| LDPC codeword length | 16 Kbits |
| Constellation size | 2~8 bpcu |
| Time de-interleaving memory size | ≤$2^{18}$ data cells |
| Pilot patterns | Pilot patterns for mobile and indoor reception |
| FFT size | 8K, 16K points |

3. Advanced Profile

The advanced profile provides highest channel capacity at the cost of more implementation complexity. This profile requires using MIMO transmission and reception, and UHDTV service is a target use case for which this profile is specifically designed. The increased capacity can also be used to allow an increased number of services in a given bandwidth, e.g., multiple SDTV or HDTV services.

The target SNR range of the advanced profile is approximately 20 to 30 dB. MIMO transmission may initially use existing elliptically-polarized transmission equipment, with extension to full-power cross-polarized transmission in the future. Key system parameters for the advanced profile are listed in below table 3.

TABLE 3

| | |
|---|---|
| LDPC codeword length | 16K, 64K bits |
| Constellation size | 8~12 bpcu |
| Time de-interleaving memory size | ≤$2^{19}$ data cells |
| Pilot patterns | Pilot pattern for fixed reception |
| FFT size | 16K, 32K points |

In this case, the base profile can be used as a profile for both the terrestrial broadcast service and the mobile broadcast service. That is, the base profile can be used to define a concept of a profile which includes the mobile profile. Also, the advanced profile can be divided advanced profile for a base profile with MIMO and advanced profile for a handheld profile with MIMO. Moreover, the three profiles can be changed according to intention of the designer.

The following terms and definitions may apply to the present invention. The following terms and definitions can be changed according to design.

auxiliary stream: sequence of cells carrying data of as yet undefined modulation and coding, which may be used for future extensions or as required by broadcasters or network operators base data pipe: data pipe that carries service signaling data baseband frame (or BBFRAME): set of Kbch bits which form the input to one FEC encoding process (BCH and LDPC encoding)

cell: modulation value that is carried by one carrier of the OFDM transmission coded block: LDPC-encoded block of PLS1 data or one of the LDPC-encoded blocks of PLS2 data data pipe: logical channel in the physical layer that carries service data or related metadata, which may carry one or multiple service(s) or service component(s).

data pipe unit: a basic unit for allocating data cells to a DP in a frame.

data symbol: OFDM symbol in a frame which is not a preamble symbol (the frame signaling symbol and frame edge symbol is included in the data symbol)

DP_ID: this 8-bit field identifies uniquely a DP within the system identified by the SYSTEM_ID dummy cell: cell carrying a pseudo-random value used to fill the remaining capacity not used for PLS signaling, DPs or auxiliary streams emergency alert channel: part of a frame that carries EAS information data frame: physical layer time slot that starts with a preamble and ends with a frame edge symbol frame repetition unit: a set of frames belonging to same or different physical layer profile including a FEF, which is repeated eight times in a super-frame fast information channel: a logical channel in a frame that carries the mapping information between a service and the corresponding base DP FECBLOCK: set of LDPC-encoded bits of a DP data FFT size: nominal FFT size used for a particular mode, equal to the active symbol period Is expressed in cycles of the elementary period T frame signaling symbol: OFDM symbol with higher pilot density used at the start of a frame in certain combinations of FFT size, guard interval and scattered pilot (sp) pattern, which carries a part of the PLS data frame edge symbol: OFDM symbol with higher pilot density used at the end of a frame in certain combinations of FFT size, guard interval and scattered pilot pattern frame-group: the set of all the frames having the same PHY profile type in a super-frame.

future extension frame: physical layer time slot within the super-frame that could be used for future extension, which starts with a preamble Futurecast UTB system: proposed physical layer broadcasting system, of which the input is one or more MPEG2-TS or IP or general stream(s) and of which the output is an RF signal input stream: A stream of data for an ensemble of services delivered to the end users by the system.

normal data symbol: data symbol excluding the frame signaling symbol and the frame edge symbol PHY profile: subset of all configurations that a corresponding receiver should implement PLS: physical layer signaling data consisting of PLS1 and PLS2

PLS1: a first set of PLS data carried in the FSS symbols having a fixed size, coding and modulation, which carries basic information about the system as well as the parameters needed to decode the PLS2

NOTE: PLS1 data remains constant for the duration of a frame-group.

PLS2: a second set of PLS data transmitted in the FSS symbol, which carries more detailed PLS data about the system and the DPs PLS2 dynamic data: PLS2 data that may dynamically change frame-by-frame PLS2 static data: PLS2 data that remains static for the duration of a frame-group preamble signaling data: signaling data carried by the preamble symbol and used to identify the basic mode of the system preamble symbol: fixed-length pilot symbol that carries basic PLS data and is located in the beginning of a frame NOTE: The preamble symbol is mainly used for fast initial band scan to detect the system signal, its timing, frequency offset, and FFT-size.

reserved for future use: not defined by the present document but may be defined in future super-frame: set of eight frame repetition units time interleaving block (TI block): set of cells within which time interleaving is carried out, corresponding to one use of the time interleaver memory TI group: unit over which dynamic capacity allocation for a particular DP is carried out, made up of an integer, dynamically varying number of XFECBLOCKs NOTE: The TI group may be mapped directly to one frame or may be mapped to multiple frames. It may contain one or more TI blocks.

Type 1 DP: DP of a frame where all DPs are mapped into the frame in TDM fashion

Type 2 DP: DP of a frame where all DPs are mapped into the frame in FDM fashion

XFECBLOCK: set of Ncells cells carrying all the bits of one LDPC FECBLOCK

FIG. 1 illustrates a structure of an apparatus for transmitting broadcast signals for future broadcast services according to an embodiment of the present invention.

The apparatus for transmitting broadcast signals for future broadcast services according to an embodiment of the present invention can include an input formatting block 1000, a BICM (Bit interleaved coding & modulation) block 1010, a frame structure block 1020, an OFDM (Orthogonal Frequency Division Multiplexing) generation block 1030 and a signaling generation block 1040. A description will be given of the operation of each module of the apparatus for transmitting broadcast signals.

IP stream/packets and MPEG2-TS are the main input formats, other stream types are handled as General Streams. In addition to these data inputs, Management Information is input to control the scheduling and allocation of the corresponding bandwidth for each input stream. One or multiple TS stream(s), IP stream(s) and/or General Stream(s) inputs are simultaneously allowed.

The input formatting block 1000 can demultiplex each input stream into one or multiple data pipe(s), to each of which an independent coding and modulation is applied. The data pipe (DP) is the basic unit for robustness control, thereby affecting quality-of-service (QoS). One or multiple service(s) or service component(s) can be carried by a single DP. Details of operations of the input formatting block 1000 will be described later.

The data pipe is a logical channel in the physical layer that carries service data or related metadata, which may carry one or multiple service(s) or service component(s).

Also, the data pipe unit: a basic unit for allocating data cells to a DP in a frame.

In the BICM block 1010, parity data is added for error correction and the encoded bit streams are mapped to complex-value constellation symbols. The symbols are interleaved across a specific interleaving depth that is used for the corresponding DP. For the advanced profile, MIMO encoding is performed in the BICM block 1010 and the additional data path is added at the output for MIMO transmission. Details of operations of the BICM block 1010 will be described later.

The Frame Building block 1020 can map the data cells of the input DPs into the OFDM symbols within a frame. After mapping, the frequency interleaving is used for frequency-domain diversity, especially to combat frequency-selective fading channels. Details of operations of the Frame Building block 1020 will be described later.

After inserting a preamble at the beginning of each frame, the OFDM Generation block 1030 can apply conventional OFDM modulation having a cyclic prefix as guard interval. For antenna space diversity, a distributed MISO scheme is applied across the transmitters. In addition, a Peak-to-Average Power Reduction (PAPR) scheme is performed in the time domain. For flexible network planning, this proposal provides a set of various FFT sizes, guard interval lengths and corresponding pilot patterns. Details of operations of the OFDM Generation block 1030 will be described later.

The Signaling Generation block 1040 can create physical layer signaling information used for the operation of each functional block. This signaling information is also transmitted so that the services of interest are properly recovered at the receiver side. Details of operations of the Signaling Generation block 1040 will be described later.

Figure 2:
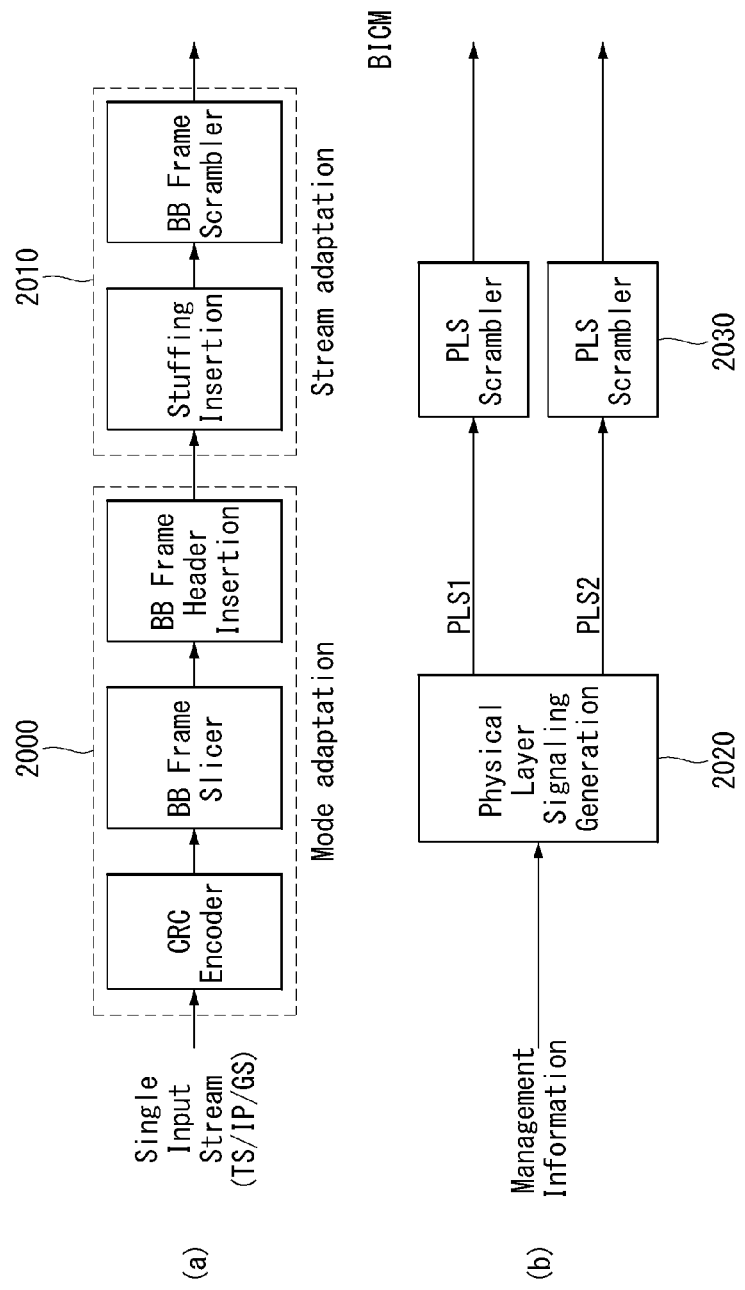
FIG. 2 illustrates an input formatting block according to one embodiment of the present invention.
Figure 3:
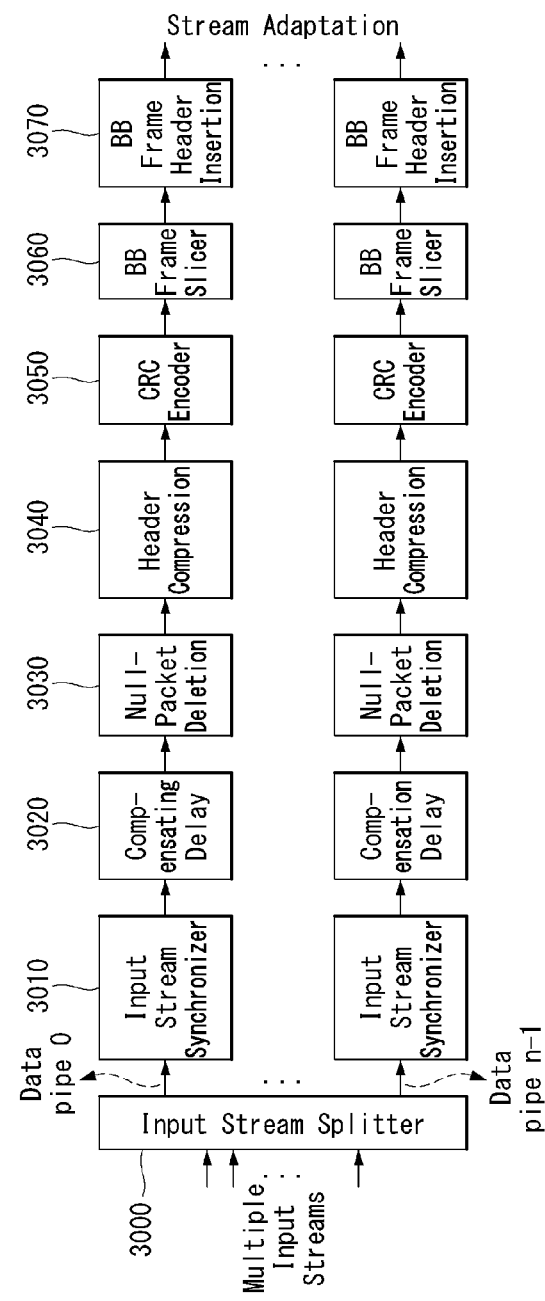
FIG. 3 illustrates an input formatting block according to another embodiment of the present invention.
Figure 4:
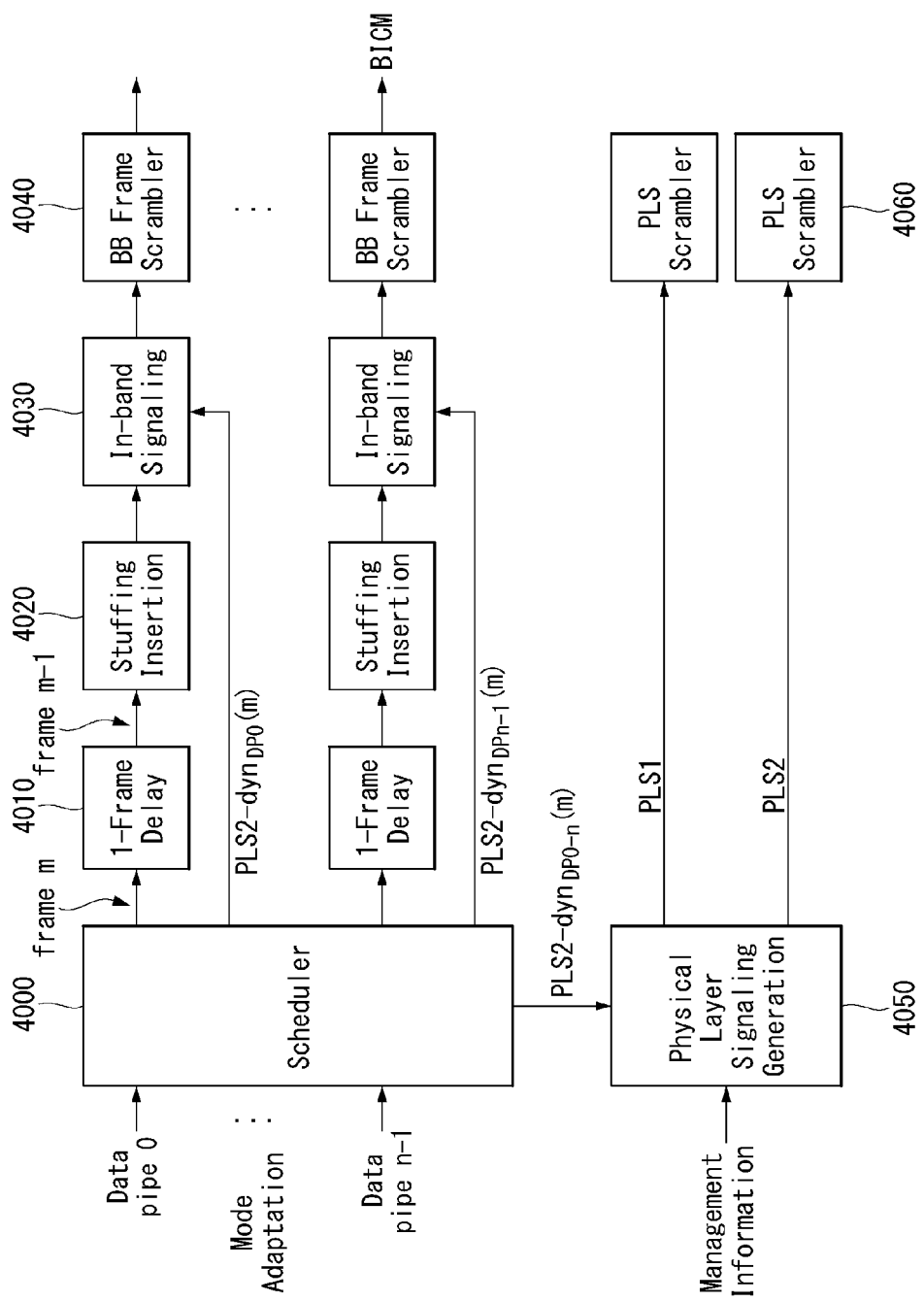
FIG. 4 illustrates an input formatting block according to another embodiment of the present invention.

FIGS. 2, 3 and 4 illustrate the input formatting block 1000 according to embodiments of the present invention. A description will be given of each figure.

FIG. 2 illustrates an input formatting block according to one embodiment of the present invention. FIG. 2 shows an input formatting module when the input signal is a single input stream.

The input formatting block illustrated in FIG. 2 corresponds to an embodiment of the input formatting block 1000 described with reference to FIG. 1.

The input to the physical layer may be composed of one or multiple data streams. Each data stream is carried by one DP. The mode adaptation modules slice the incoming data stream into data fields of the baseband frame (BBF). The system supports three types of input data streams: MPEG2-TS, Internet protocol (IP) and Generic stream (GS). MPEG2-TS is characterized by fixed length (188 byte) packets with the first byte being a sync-byte (0x47). An IP stream is composed of variable length IP datagram packets, as signaled within IP packet headers. The system supports both IPv4 and IPv6 for the IP stream. GS may be composed of variable length packets or constant length packets, signaled within encapsulation packet headers.

(a) shows a mode adaptation block 2000 and a stream adaptation 2010 for signal DP and (b) shows a PLS generation block 2020 and a PLS scrambler 2030 for generating and processing PLS data. A description will be given of the operation of each block.

The Input Stream Splitter splits the input TS, IP, GS streams into multiple service or service component (audio, video, etc.) streams. The mode adaptation module 2010 is comprised of a CRC Encoder, BB (baseband) Frame Slicer, and BB Frame Header Insertion block.

The CRC Encoder provides three kinds of CRC encoding for error detection at the user packet (UP) level, i.e., CRC-8, CRC-16, and CRC-32. The computed CRC bytes are appended after the UP. CRC-8 is used for TS stream and CRC-32 for IP stream. If the GS stream doesn't provide the CRC encoding, the proposed CRC encoding should be applied.

BB Frame Slicer maps the input into an internal logical-bit format. The first received bit is defined to be the MSB. The BB Frame Slicer allocates a number of input bits equal to the available data field capacity. To allocate a number of input bits equal to the BBF payload, the UP packet stream is sliced to fit the data field of BBF.

BB Frame Header Insertion block can insert fixed length BBF header of 2 bytes is inserted in front of the BB Frame. The BBF header is composed of STUFFI (1 bit), SYNCD (13 bits), and RFU (2 bits). In addition to the fixed 2-Byte BBF header, BBF can have an extension field (1 or 3 bytes) at the end of the 2-byte BBF header.

The stream adaptation 2010 is comprised of stuffing insertion block and BB scrambler.

The stuffing insertion block can insert stuffing field into a payload of a BB frame. If the input data to the stream adaptation is sufficient to fill a BB-Frame, STUFFI is set to '0' and the BBF has no stuffing field. Otherwise STUFFI is set to '1' and the stuffing field is inserted immediately after the BBF header. The stuffing field comprises two bytes of the stuffing field header and a variable size of stuffing data.

The BB scrambler scrambles complete BBF for energy dispersal. The scrambling sequence is synchronous with the BBF. The scrambling sequence is generated by the feedback shift register.

The PLS generation block 2020 can generate physical layer signaling (PLS) data. The PLS provides the receiver with a means to access physical layer DPs. The PLS data consists of PLS1 data and PLS2 data.

The PLS1 data is a first set of PLS data carried in the FSS symbols in the frame having a fixed size, coding and modulation, which carries basic information about the system as well as the parameters needed to decode the PLS2 data. The PLS1 data provides basic transmission parameters including parameters required to enable the reception and decoding of the PLS2 data. Also, the PLS1 data remains constant for the duration of a frame-group.

The PLS2 data is a second set of PLS data transmitted in the FSS symbol, which carries more detailed PLS data about the system and the DPs. The PLS2 contains parameters that provide sufficient information for the receiver to decode the desired DP. The PLS2 signaling further consists of two types of parameters, PLS2 Static data (PLS2-STAT data) and PLS2 dynamic data (PLS2-DYN data). The PLS2 Static data is PLS2 data that remains static for the duration of a frame-group and the PLS2 dynamic data is PLS2 data that may dynamically change frame-by-frame.

Details of the PLS data will be described later.

The PLS scrambler 2030 can scramble the generated PLS data for energy dispersal.

The above-described blocks may be omitted or replaced by blocks having similar or identical functions.

FIG. 3 illustrates an input formatting block according to another embodiment of the present invention.

The input formatting block illustrated in FIG. 3 corresponds to an embodiment of the input formatting block 1000 described with reference to FIG. 1.

FIG. 3 shows a mode adaptation block of the input formatting block when the input signal corresponds to multiple input streams.

The mode adaptation block of the input formatting block for processing the multiple input streams can independently process the multiple input streams.

Referring to FIG. 3, the mode adaptation block for respectively processing the multiple input streams can include an input stream splitter 3000, an input stream synchronizer 3010, a compensating delay block 3020, a null packet deletion block 3030, a head compression block 3040, a CRC encoder 3050, a BB frame slicer 3060 and a BB header insertion block 3070. Description will be given of each block of the mode adaptation block.

Operations of the CRC encoder 3050, BB frame slicer 3060 and BB header insertion block 3070 correspond to those of the CRC encoder, BB frame slicer and BB header insertion block described with reference to FIG. 2 and thus description thereof is omitted.

The input stream splitter 3000 can split the input TS, IP, GS streams into multiple service or service component (audio, video, etc.) streams.

The input stream synchronizer 3010 may be referred as ISSY. The ISSY can provide suitable means to guarantee Constant Bit Rate (CBR) and constant end-to-end transmission delay for any input data format. The ISSY is always used for the case of multiple DPs carrying TS, and optionally used for multiple DPs carrying GS streams.

The compensating delay block 3020 can delay the split TS packet stream following the insertion of ISSY information to allow a TS packet recombining mechanism without requiring additional memory in the receiver.

The null packet deletion block 3030, is used only for the TS input stream case. Some TS input streams or split TS streams may have a large number of null-packets present in order to accommodate VBR (variable bit-rate) services in a CBR TS stream. In this case, in order to avoid unnecessary transmission overhead, null-packets can be identified and not transmitted. In the receiver, removed null-packets can be re-inserted in the exact place where they were originally by reference to a deleted null-packet (DNP) counter that is inserted in the transmission, thus guaranteeing constant bit-rate and avoiding the need for time-stamp (PCR) updating.

The head compression block 3040 can provide packet header compression to increase transmission efficiency for TS or IP input streams. Because the receiver can have a priori information on certain parts of the header, this known information can be deleted in the transmitter.

For Transport Stream, the receiver has a-priori information about the sync-byte configuration (0x47) and the packet length (188 Byte). If the input TS stream carries content that has only one PID, i.e., for only one service component (video, audio, etc.) or service sub-component (SVC base layer, SVC enhancement layer, MVC base view or MVC dependent views), TS packet header compression can be applied (optionally) to the Transport Stream. IP packet header compression is used optionally if the input steam is an IP stream.

The above-described blocks may be omitted or replaced by blocks having similar or identical functions.

FIG. 4 illustrates an input formatting block according to another embodiment of the present invention.

The input formatting block illustrated in FIG. 4 corresponds to an embodiment of the input formatting block 1000 described with reference to FIG. 1.

FIG. 4 illustrates a stream adaptation block of the input formatting module when the input signal corresponds to multiple input streams.

Referring to FIG. 4, the mode adaptation block for respectively processing the multiple input streams can include a scheduler 4000, an 1-Frame delay block 4010, a stuffing insertion block 4020, an in-band signaling 4030, a BB Frame scrambler 4040, a PLS generation block 4050 and a PLS scrambler 4060. Description will be given of each block of the stream adaptation block.

Operations of the stuffing insertion block 4020, the BB Frame scrambler 4040, the PLS generation block 4050 and the PLS scrambler 4060 correspond to those of the stuffing insertion block, BB scrambler, PLS generation block and the PLS scrambler described with reference to FIG. 2 and thus description thereof is omitted.

The scheduler 4000 can determine the overall cell allocation across the entire frame from the amount of FEC-BLOCKs of each DP. Including the allocation for PLS, EAC and FIC, the scheduler generate the values of PLS2-DYN data, which is transmitted as in-band signaling or PLS cell in FSS of the frame. Details of FECBLOCK, EAC and FIC will be described later.

The 1-Frame delay block 4010 can delay the input data by one transmission frame such that scheduling information about the next frame can be transmitted through the current frame for in-band signaling information to be inserted into the DPs.

The in-band signaling 4030 can insert un-delayed part of the PLS2 data into a DP of a frame.

The above-described blocks may be omitted or replaced by blocks having similar or identical functions.

Figure 5:
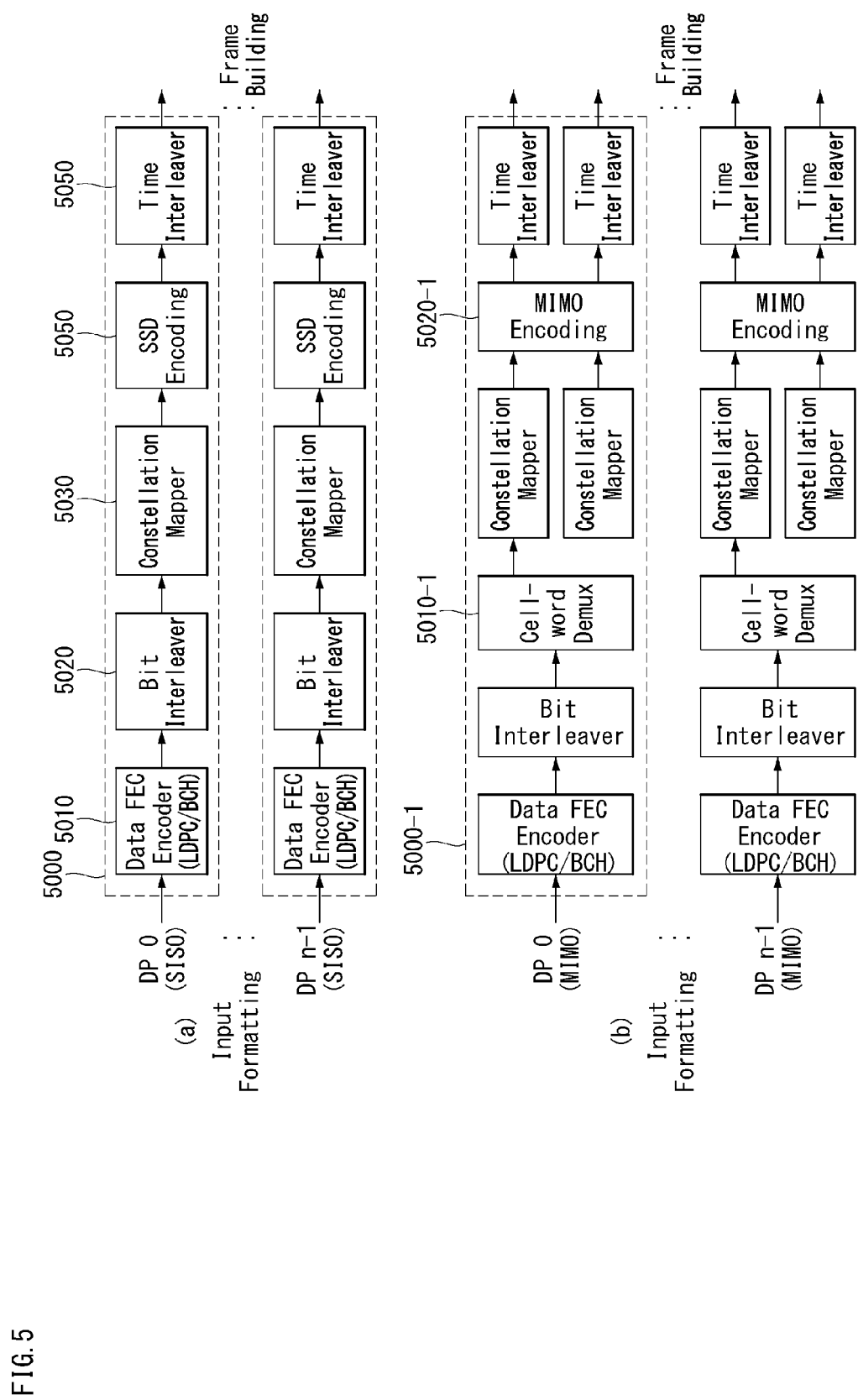
FIG. 5 illustrates a BICM block according to an embodiment of the present invention.

FIG. 5 illustrates a BICM block according to an embodiment of the present invention.

The BICM block illustrated in FIG. 5 corresponds to an embodiment of the BICM block 1010 described with reference to FIG. 1.

As described above, the apparatus for transmitting broadcast signals for future broadcast services according to an embodiment of the present invention can provide a terrestrial broadcast service, mobile broadcast service, UHDTV service, etc.

Since QoS (quality of service) depends on characteristics of a service provided by the apparatus for transmitting broadcast signals for future broadcast services according to an embodiment of the present invention, data corresponding to respective services needs to be processed through different schemes. Accordingly, the a BICM block according to an embodiment of the present invention can independently process DPs input thereto by independently applying SISO, MISO and MIMO schemes to the data pipes respectively corresponding to data paths. Consequently, the apparatus for transmitting broadcast signals for future broadcast services according to an embodiment of the present invention can control QoS for each service or service component transmitted through each DP.

(a) shows the BICM block shared by the base profile and the handheld profile and (b) shows the BICM block of the advanced profile.

The BICM block shared by the base profile and the handheld profile and the BICM block of the advanced profile can include plural processing blocks for processing each DP.

A description will be given of each processing block of the BICM block for the base profile and the handheld profile and the BICM block for the advanced profile.

A processing block 5000 of the BICM block for the base profile and the handheld profile can include a Data FEC encoder 5010, a bit interleaver 5020, a constellation mapper 5030, an SSD (Signal Space Diversity) encoding block 5040 and a time interleaver 5050.

The Data FEC encoder 5010 can perform the FEC encoding on the input BBF to generate FECBLOCK procedure using outer coding (BCH), and inner coding (LDPC). The outer coding (BCH) is optional coding method. Details of operations of the Data FEC encoder 5010 will be described later.

The bit interleaver 5020 can interleave outputs of the Data FEC encoder 5010 to achieve optimized performance with combination of the LDPC codes and modulation scheme while providing an efficiently implementable structure. Details of operations of the bit interleaver 5020 will be described later.

The constellation mapper 5030 can modulate each cell word from the bit interleaver 5020 in the base and the handheld profiles, or cell word from the Cell-word demultiplexer 5010-1 in the advanced profile using either QPSK, QAM-16, non-uniform QAM (NUQ-64, NUQ-256, NUQ-1024) or non-uniform constellation (NUC-16, NUC-64, NUC-256, NUC-1024) to give a power-normalized constellation point, el. This constellation mapping is applied only for DPs. Observe that QAM-16 and NUQs are square shaped, while NUCs have arbitrary shape. When each constellation is rotated by any multiple of 90 degrees, the rotated constellation exactly overlaps with its original one. This "rotation-sense" symmetric property makes the capacities and the average powers of the real and imaginary components equal to each other. Both NUQs and NUCs are defined specifically for each code rate and the particular one used is signaled by the parameter DP_MOD filed in PLS2 data.

The SSD encoding block 5040 can precode cells in two (2D), three (3D), and four (4D) dimensions to increase the reception robustness under difficult fading conditions.

The time interleaver 5050 can operates at the DP level. The parameters of time interleaving (TI) may be set differently for each DP. Details of operations of the time interleaver 5050 will be described later.

A processing block 5000-1 of the BICM block for the advanced profile can include the Data FEC encoder, bit interleaver, constellation mapper, and time interleaver. However, the processing block 5000-1 is distinguished from the processing block 5000 further includes a cell-word demultiplexer 5010-1 and a MIMO encoding block 5020-1.

Also, the operations of the Data FEC encoder, bit interleaver, constellation mapper, and time interleaver in the processing block 5000-1 correspond to those of the Data FEC encoder 5010, bit interleaver 5020, constellation mapper 5030, and time interleaver 5050 described and thus description thereof is omitted.

The cell-word demultiplexer 5010-1 is used for the DP of the advanced profile to divide the single cell-word stream into dual cell-word streams for MIMO processing. Details of operations of the cell-word demultiplexer 5010-1 will be described later.

The MIMO encoding block 5020-1 can processing the output of the cell-word demultiplexer 5010-1 using MIMO encoding scheme. The MIMO encoding scheme was optimized for broadcasting signal transmission. The MIMO technology is a promising way to get a capacity increase but it depends on channel characteristics. Especially for broadcasting, the strong LOS component of the channel or a difference in the received signal power between two antennas caused by different signal propagation characteristics makes it difficult to get capacity gain from MIMO. The proposed MIMO encoding scheme overcomes this problem using a rotation-based pre-coding and phase randomization of one of the MIMO output signals.

MIMO encoding is intended for a 2×2 MIMO system requiring at least two antennas at both the transmitter and the receiver. Two MIMO encoding modes are defined in this proposal; full-rate spatial multiplexing (FR-SM) and full-rate full-diversity spatial multiplexing (FRFD-SM). The FR-SM encoding provides capacity increase with relatively small complexity increase at the receiver side while the FRFD-SM encoding provides capacity increase and additional diversity gain with a great complexity increase at the receiver side. The proposed MIMO encoding scheme has no restriction on the antenna polarity configuration.

MIMO processing is required for the advanced profile frame, which means all DPs in the advanced profile frame are processed by the MIMO encoder. MIMO processing is applied at DP level. Pairs of the Constellation Mapper outputs NUQ (e1,$i$ and e2,$i$) are fed to the input of the MIMO Encoder. Paired MIMO Encoder output (g1,$i$ and g2,$i$) is transmitted by the same carrier k and OFDM symbol 1 of their respective TX antennas.

The above-described blocks may be omitted or replaced by blocks having similar or identical functions.

Figure 6:
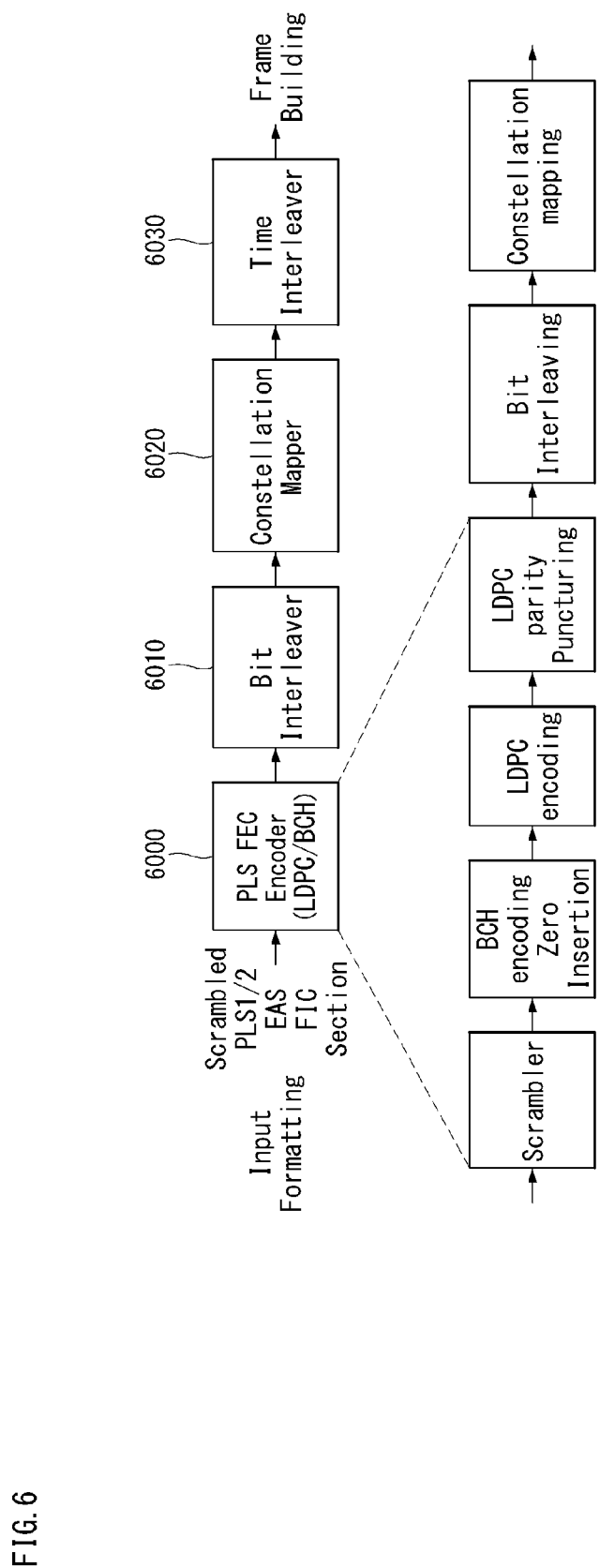
FIG. 6 illustrates a BICM block according to another embodiment of the present invention.

FIG. 6 illustrates a BICM block according to another embodiment of the present invention.

The BICM block illustrated in FIG. 6 corresponds to an embodiment of the BICM block 1010 described with reference to FIG. 1.

FIG. 6 illustrates a BICM block for protection of physical layer signaling (PLS), emergency alert channel (EAC) and fast information channel (FIC). EAC is a part of a frame that carries EAS information data and FIC is a logical channel in a frame that carries the mapping information between a service and the corresponding base DP. Details of the EAC and FIC will be described later.

Referring to FIG. 6, the BICM block for protection of PLS, EAC and FIC can include a PLS FEC encoder 6000, a bit interleaver 6010, a constellation mapper 6020 and time interleaver 6030.

Also, the PLS FEC encoder 6000 can include a scrambler, BCH encoding/zero insertion block, LDPC encoding block and LDPC parity puncturing block. Description will be given of each block of the BICM block.

The PLS FEC encoder 6000 can encode the scrambled PLS 1/2 data, EAC and FIC section.

The scrambler can scramble PLS1 data and PLS2 data before BCH encoding and shortened and punctured LDPC encoding.

The BCH encoding/zero insertion block can perform outer encoding on the scrambled PLS 1/2 data using the shortened BCH code for PLS protection and insert zero bits after the BCH encoding. For PLS1 data only, the output bits of the zero insertion may be permutted before LDPC encoding.

The LDPC encoding block can encode the output of the BCH encoding/zero insertion block using LDPC code. To generate a complete coded block, Cldpc, parity bits, Pldpc are encoded systematically from each zero-inserted PLS information block, Ildpc and appended after it.

$$C_{ldpc} = [I_{ldpc} P_{ldpc}] = [i_0, i_1, \ldots, i_{K_{ldpc}-1}, p_0, p_1, \ldots, p_{N_{ldpc}-K_{ldpc}-1}]$$ [Equation 1]

The LDPC code parameters for PLS1 and PLS2 are as following table 4.

TABLE 4

| Signaling Type | Ksig | Kbch | Nbch_parity | Kldpc (=Nbch) | Nldpc | Nldpc_parity | code rate | Qldpc |
|---|---|---|---|---|---|---|---|---|
| PLS1 | 342 | 1020 | 60 | 1080 | 4320 | 3240 | 1/4 | 36 |
| PLS2 | <1021 | | | | | | | |
| | >1020 | 2100 | | 2160 | 7200 | 5040 | 3/10 | 56 |

The LDPC parity puncturing block can perform puncturing on the PLS1 data and PLS 2 data.

When shortening is applied to the PLS1 data protection, some LDPC parity bits are punctured after LDPC encoding. Also, for the PLS2 data protection, the LDPC parity bits of PLS2 are punctured after LDPC encoding. These punctured bits are not transmitted.

The bit interleaver 6010 can interleave the each shortened and punctured PLS1 data and PLS2 data.

The constellation mapper 6020 can map the bit interleaved PLS1 data and PLS2 data onto constellations.

The time interleaver 6030 can interleave the mapped PLS1 data and PLS2 data.

The above-described blocks may be omitted or replaced by blocks having similar or identical functions.

Figure 7:
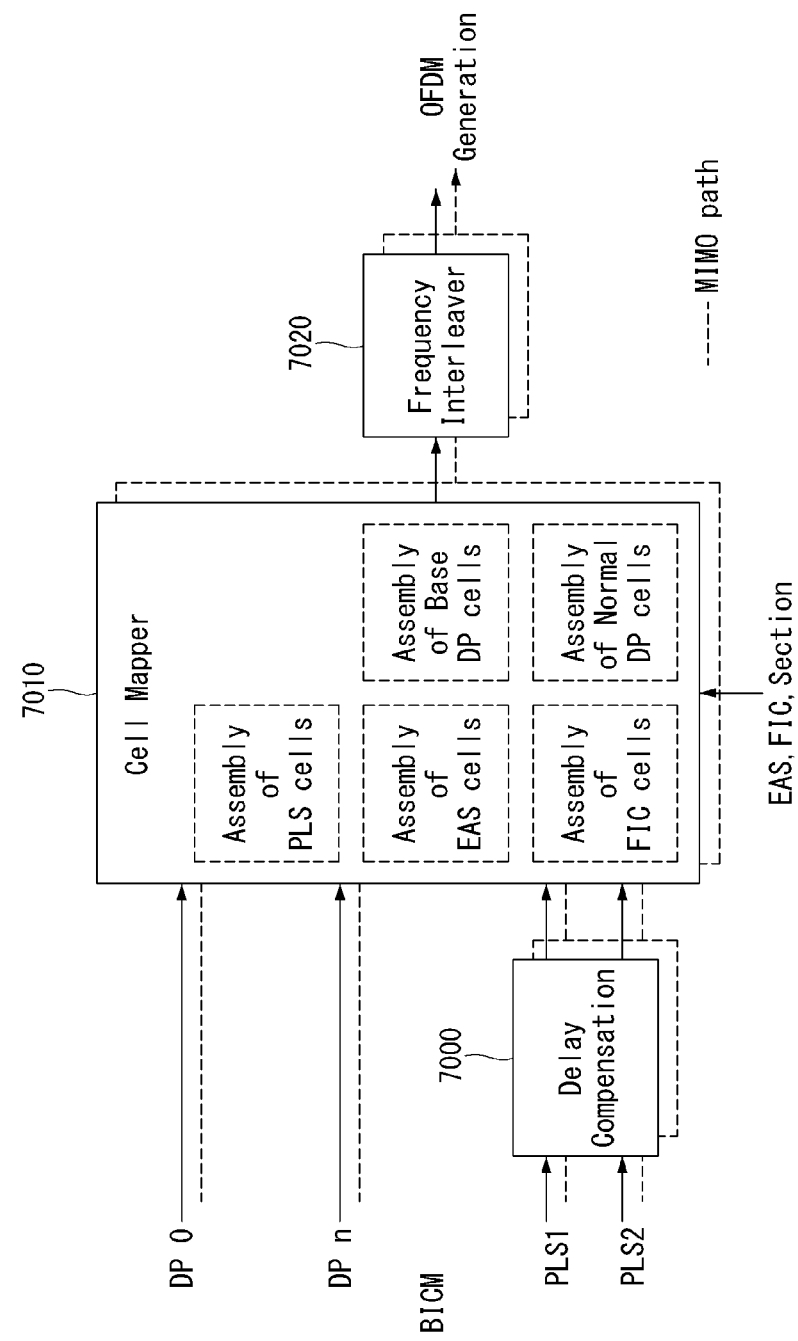
FIG. 7 illustrates a frame building block according to one embodiment of the present invention.

FIG. 7 illustrates a frame building block according to one embodiment of the present invention.

The frame building block illustrated in FIG. 7 corresponds to an embodiment of the frame building block 1020 described with reference to FIG. 1.

Referring to FIG. 7, the frame building block can include a delay compensation block 7000, a cell mapper 7010 and a frequency interleaver 7020. Description will be given of each block of the frame building block.

The delay compensation block 7000 can adjust the timing between the data pipes and the corresponding PLS data to ensure that they are co-timed at the transmitter end. The PLS data is delayed by the same amount as data pipes are by addressing the delays of data pipes caused by the Input Formatting block and BICM block. The delay of the BICM block is mainly due to the time interleaver 5050. In-band signaling data carries information of the next TI group so that they are carried one frame ahead of the DPs to be signaled. The Delay Compensating block delays in-band signaling data accordingly.

The cell mapper 7010 can map PLS, EAC, FIC, DPs, auxiliary streams and dummy cells into the active carriers of the OFDM symbols in the frame. The basic function of the cell mapper 7010 is to map data cells produced by the TIs for each of the DPs, PLS cells, and EAC/FIC cells, if any, into arrays of active OFDM cells corresponding to each of the OFDM symbols within a frame. Service signaling data (such as PSI (program specific information)/SI) can be separately gathered and sent by a data pipe. The Cell Mapper operates according to the dynamic information produced by the scheduler and the configuration of the frame structure. Details of the frame will be described later.

The frequency interleaver 7020 can randomly interleave data cells received from the cell mapper 7010 to provide frequency diversity. Also, the frequency interleaver 7020 can operate on very OFDM symbol pair comprised of two sequential OFDM symbols using a different interleaving-seed order to get maximum interleaving gain in a single frame. Details of operations of the frequency interleaver 7020 will be described later.

The above-described blocks may be omitted or replaced by blocks having similar or identical functions.

Figure 8:
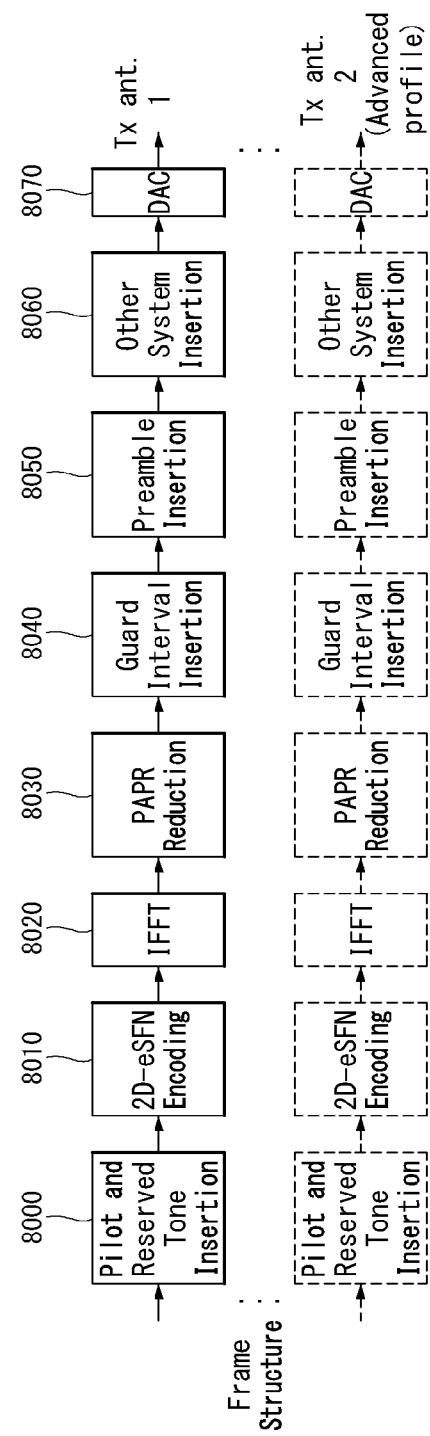
FIG. 8 illustrates an OFDM generation block according to an embodiment of the present invention.

FIG. 8 illustrates an OFMD generation block according to an embodiment of the present invention.

The OFMD generation block illustrated in FIG. 8 corresponds to an embodiment of the OFMD generation block 1030 described with reference to FIG. 1.

The OFDM generation block modulates the OFDM carriers by the cells produced by the Frame Building block, inserts the pilots, and produces the time domain signal for transmission. Also, this block subsequently inserts guard intervals, and applies PAPR (Peak-to-Average Power Radio) reduction processing to produce the final RF signal.

Referring to FIG. 8, the frame building block can include a pilot and reserved tone insertion block 8000, a 2D-eSFN encoding block 8010, an IFFT (Inverse Fast Fourier Transform) block 8020, a PAPR reduction block 8030, a guard interval insertion block 8040, a preamble insertion block 8050, other system insertion block 8060 and a DAC block 8070. Description will be given of each block of the frame building block.

The pilot and reserved tone insertion block 8000 can insert pilots and the reserved tone.

Various cells within the OFDM symbol are modulated with reference information, known as pilots, which have transmitted values known a priori in the receiver. The information of pilot cells is made up of scattered pilots (SP), continual pilots (CP), edge pilots (EP), FSS (frame signaling symbol) pilots and FES (frame edge symbol) pilots. Each pilot is transmitted at a particular boosted power level according to pilot type and pilot pattern. The value of the pilot information is derived from a reference sequence, which is a series of values, one for each transmitted carrier on any given symbol. The pilots can be used for frame synchronization, frequency synchronization, time synchronization, channel estimation, and transmission mode identification, and also can be used to follow the phase noise.

Reference information, taken from the reference sequence, is transmitted in scattered pilot cells in every symbol except the preamble, FSS and FES of the frame. Continual pilots are inserted in every symbol of the frame. The number and location of continual pilots depends on both the FFT size and the scattered pilot pattern. The edge carriers are edge pilots in every symbol except for the preamble symbol. They are inserted in order to allow frequency interpolation up to the edge of the spectrum. FSS pilots are inserted in FSS(s) and FES pilots are inserted in FES. They are inserted in order to allow time interpolation up to the edge of the frame.

The system according to an embodiment of the present invention supports the SFN network, where distributed MISO scheme is optionally used to support very robust transmission mode. The 2D-eSFN is a distributed MISO scheme that uses multiple TX antennas, each of which is located in the different transmitter site in the SFN network.

The 2D-eSFN encoding block 8010 can process a 2D-eSFN processing to distorts the phase of the signals transmitted from multiple transmitters, in order to create both time and frequency diversity in the SFN configuration. Hence, burst errors due to low flat fading or deep-fading for a long time can be mitigated.

The IFFT block 8020 can modulate the output from the 2D-eSFN encoding block 8010 using OFDM modulation scheme. Any cell in the data symbols which has not been designated as a pilot (or as a reserved tone) carries one of the data cells from the frequency interleaver. The cells are mapped to OFDM carriers.

The PAPR reduction block 8030 can perform a PAPR reduction on input signal using various PAPR reduction algorithm in the time domain.

The guard interval insertion block 8040 can insert guard intervals and the preamble insertion block 8050 can insert preamble in front of the signal. Details of a structure of the preamble will be described later. The other system insertion block 8060 can multiplex signals of a plurality of broadcast transmission/reception systems in the time domain such that data of two or more different broadcast transmission/reception systems providing broadcast services can be simultaneously transmitted in the same RF signal bandwidth. In this case, the two or more different broadcast transmission/reception systems refer to systems providing different broadcast services. The different broadcast services may refer to a terrestrial broadcast service, mobile broadcast service, etc. Data related to respective broadcast services can be transmitted through different frames.

The DAC block 8070 can convert an input digital signal into an analog signal and output the analog signal. The signal output from the DAC block 7800 can be transmitted through multiple output antennas according to the physical layer profiles. A Tx antenna according to an embodiment of the present invention can have vertical or horizontal polarity.

The above-described blocks may be omitted or replaced by blocks having similar or identical functions according to design.

Figure 9:
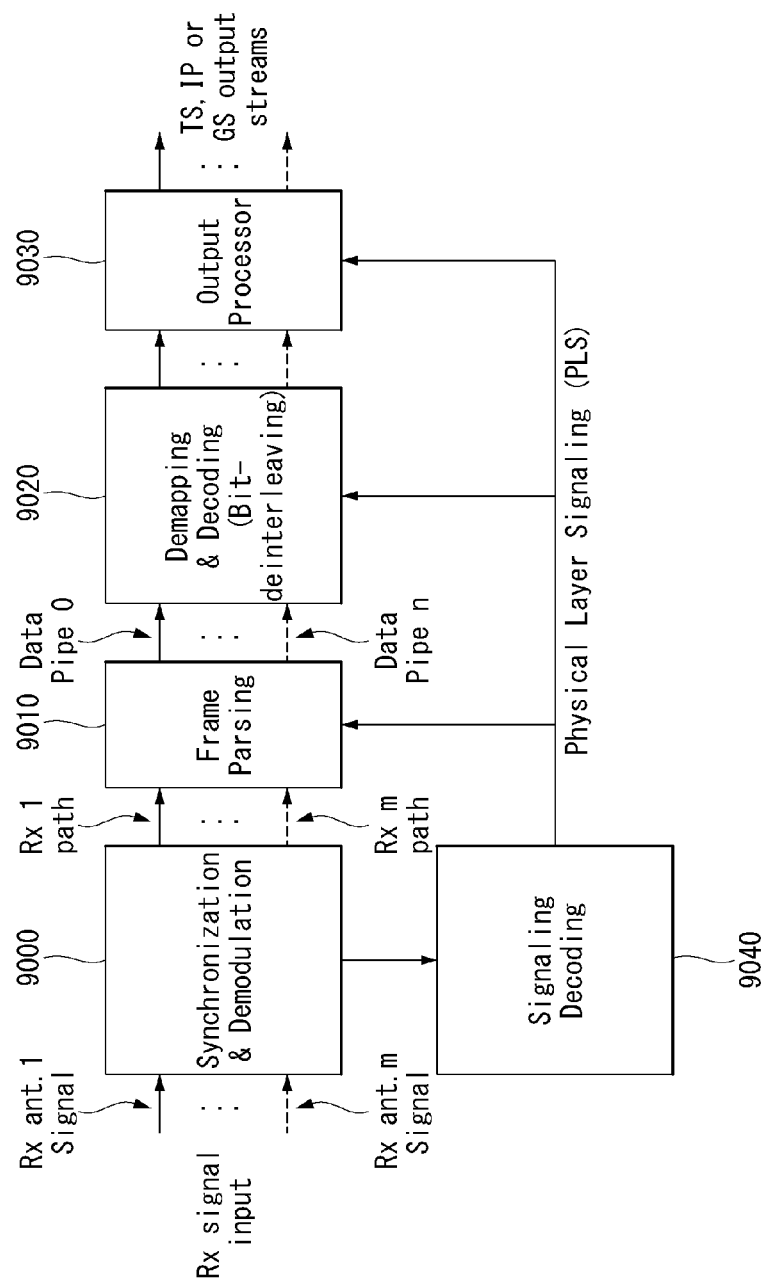
FIG. 9 illustrates a structure of an apparatus for receiving broadcast signals for future broadcast services according to an embodiment of the present invention.

FIG. 9 illustrates a structure of an apparatus for receiving broadcast signals for future broadcast services according to an embodiment of the present invention.

The apparatus for receiving broadcast signals for future broadcast services according to an embodiment of the present invention can correspond to the apparatus for transmitting broadcast signals for future broadcast services, described with reference to FIG. 1.

The apparatus for receiving broadcast signals for future broadcast services according to an embodiment of the present invention can include a synchronization & demodulation module 9000, a frame parsing module 9010, a demapping & decoding module 9020, an output processor 9030 and a signaling decoding module 9040. A description will be given of operation of each module of the apparatus for receiving broadcast signals.

The synchronization & demodulation module 9000 can receive input signals through m Rx antennas, perform signal detection and synchronization with respect to a system corresponding to the apparatus for receiving broadcast signals and carry out demodulation corresponding to a reverse procedure of the procedure performed by the apparatus for transmitting broadcast signals.

The frame parsing module 9010 can parse input signal frames and extract data through which a service selected by a user is transmitted. If the apparatus for transmitting broadcast signals performs interleaving, the frame parsing module 9010 can carry out deinterleaving corresponding to a reverse procedure of interleaving. In this case, the positions of a signal and data that need to be extracted can be obtained by decoding data output from the signaling decoding module 9400 to restore scheduling information generated by the apparatus for transmitting broadcast signals.

The demapping & decoding module 9020 can convert the input signals into bit domain data and then deinterleave the same as necessary. The demapping & decoding module 9200 can perform demapping for mapping applied for transmission efficiency and correct an error generated on a transmission channel through decoding. In this case, the demapping & decoding module 9020 can obtain transmission parameters necessary for demapping and decoding by decoding the data output from the signaling decoding module 9040.

The output processor 9030 can perform reverse procedures of various compression/signal processing procedures which are applied by the apparatus for transmitting broadcast signals to improve transmission efficiency. In this case, the output processor 9030 can acquire necessary control information from data output from the signaling decoding module 9040. The output of the output processor 9030 corresponds to a signal input to the apparatus for transmitting broadcast signals and may be MPEG-TSs, IP streams (v4 or v6) and generic streams.

The signaling decoding module 9040 can obtain PLS information from the signal demodulated by the synchronization & demodulation module 9000. As described above, the frame parsing module 9010, demapping & decoding module 9020 and output processor 9030 can execute functions thereof using the data output from the signaling decoding module 9040.

Figure 10:
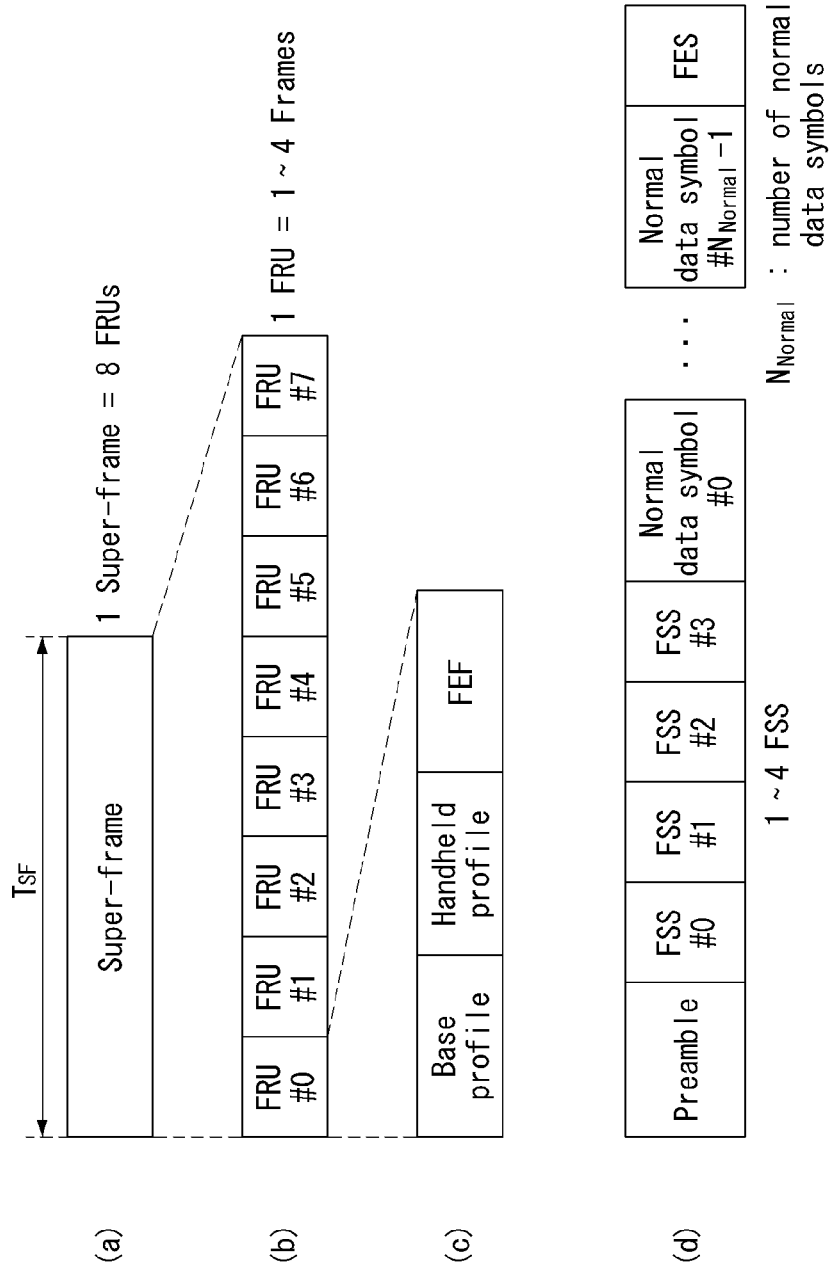
FIG. 10 illustrates a frame structure according to an embodiment of the present invention.

FIG. 10 illustrates a frame structure according to an embodiment of the present invention.

FIG. 10 shows an example configuration of the frame types and FRUs in a super-frame. (a) shows a super frame according to an embodiment of the present invention, (b) shows FRU (Frame Repetition Unit) according to an embodiment of the present invention, (c) shows frames of variable PHY profiles in the FRU and (d) shows a structure of a frame.

A super-frame may be composed of eight FRUs. The FRU is a basic multiplexing unit for TDM of the frames, and is repeated eight times in a super-frame.

Each frame in the FRU belongs to one of the PHY profiles, (base, handheld, advanced) or FEF. The maximum allowed number of the frames in the FRU is four and a given PHY profile can appear any number of times from zero times to four times in the FRU (e.g., base, base, handheld, advanced). PHY profile definitions can be extended using reserved values of the PHY_PROFILE in the preamble, if required.

The FEF part is inserted at the end of the FRU, if included. When the FEF is included in the FRU, the minimum number of FEFs is 8 in a super-frame. It is not recommended that FEF parts be adjacent to each other.

One frame is further divided into a number of OFDM symbols and a preamble. As shown in (d), the frame comprises a preamble, one or more frame signaling symbols (FSS), normal data symbols and a frame edge symbol (FES).

The preamble is a special symbol that enables fast Futurecast UTB system signal detection and provides a set of basic transmission parameters for efficient transmission and reception of the signal. The detailed description of the preamble will be will be described later.

The main purpose of the FSS(s) is to carry the PLS data. For fast synchronization and channel estimation, and hence fast decoding of PLS data, the FSS has more dense pilot pattern than the normal data symbol. The FES has exactly the same pilots as the FSS, which enables frequency-only interpolation within the FES and temporal interpolation, without extrapolation, for symbols immediately preceding the FES.

Figure 11:
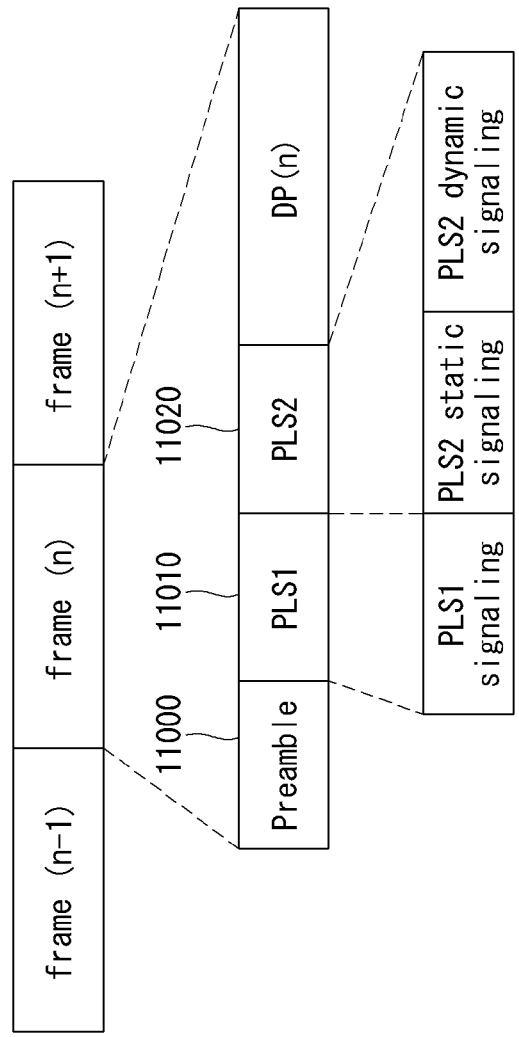
FIG. 11 illustrates a signaling hierarchy structure of the frame according to an embodiment of the present invention.

FIG. 11 illustrates a signaling hierarchy structure of the frame according to an embodiment of the present invention.

FIG. 11 illustrates the signaling hierarchy structure, which is split into three main parts: the preamble signaling data 11000, the PLS1 data 11010 and the PLS2 data 11020. The purpose of the preamble, which is carried by the preamble symbol in every frame, is to indicate the transmission type and basic transmission parameters of that frame. The PLS1 enables the receiver to access and decode the PLS2 data, which contains the parameters to access the DP of interest. The PLS2 is carried in every frame and split into two main parts: PLS2-STAT data and PLS2-DYN data. The static and dynamic portion of PLS2 data is followed by padding, if necessary.

FIG. 12 illustrates preamble signaling data according to an embodiment of the present invention.

Preamble signaling data carries 21 bits of information that are needed to enable the receiver to access PLS data and trace DPs within the frame structure. Details of the preamble signaling data are as follows:

PHY_PROFILE: This 3-bit field indicates the PHY profile type of the current frame. The mapping of different PHY profile types is given in below table 5.

TABLE 5

| Value | PHY profile |
|---|---|
| 000 | Base profile |
| 001 | Handheld profile |
| 010 | Advanced profiled |
| 011~110 | Reserved |
| 111 | FEF |

FFT_SIZE: This 2 bit field indicates the FFT size of the current frame within a frame-group, as described in below table 6.

TABLE 6

| Value | FFT size |
|---|---|
| 00 | 8K FFT |
| 01 | 16K FFT |
| 10 | 32K FFT |
| 11 | Reserved |

GI_FRACTION: This 3 bit field indicates the guard interval fraction value in the current super-frame, as described in below table 7.

TABLE 7

| Value | GI_FRACTION |
|---|---|
| 000 | 1/5 |
| 001 | 1/10 |
| 010 | 1/20 |
| 011 | 1/40 |
| 100 | 1/80 |
| 101 | 1/160 |
| 110~111 | Reserved |

EAC_FLAG: This 1 bit field indicates whether the EAC is provided in the current frame. If this field is set to '1', emergency alert service (EAS) is provided in the current frame. If this field set to '0', EAS is not carried in the current frame. This field can be switched dynamically within a super-frame.

PILOT_MODE: This 1-bit field indicates whether the pilot mode is mobile mode or fixed mode for the current frame in the current frame-group. If this field is set to '0', mobile pilot mode is used. If the field is set to '1', the fixed pilot mode is used.

PAPR_FLAG: This 1-bit field indicates whether PAPR reduction is used for the current frame in the current frame-group. If this field is set to value '1', tone reservation is used for PAPR reduction. If this field is set to '0', PAPR reduction is not used.

FRU_CONFIGURE: This 3-bit field indicates the PHY profile type configurations of the frame repetition units (FRU) that are present in the current super-frame. All profile types conveyed in the current super-frame are identified in this field in all preambles in the current super-frame. The 3-bit field has a different definition for each profile, as show in below table 8.

PLS1 data provides basic transmission parameters including parameters required to enable the reception and decoding of the PLS2. As above mentioned, the PLS1 data remain unchanged for the entire duration of one frame-group. The detailed definition of the signaling fields of the PLS1 data are as follows:

PREAMBLE_DATA: This 20-bit field is a copy of the preamble signaling data excluding the EAC_FLAG.

NUM_FRAME_FRU: This 2-bit field indicates the number of the frames per FRU.

PAYLOAD_TYPE: This 3-bit field indicates the format of the payload data carried in the frame-group. PAYLOAD_TYPE is signaled as shown in table 9.

TABLE 9

| value | Payload type |
|---|---|
| 1XX | TS stream is transmitted |
| X1X | IP stream is transmitted |
| XX1 | GS stream is transmitted |

NUM_FSS: This 2-bit field indicates the number of FSS symbols in the current frame.

SYSTEM_VERSION: This 8-bit field indicates the version of the transmitted signal format. The SYSTEM_VERSION is divided into two 4-bit fields, which are a major version and a minor version.

Major version: The MSB four bits of SYSTEM_VERSION field indicate major version information. A change in the major version field indicates a non-backward-compatible change. The default value is '0000'. For the version described in this standard, the value is set to '0000'.

Minor version: The LSB four bits of SYSTEM_VERSION field indicate minor version information. A change in the minor version field is backward-compatible.

CELL_ID: This is a 16-bit field which uniquely identifies a geographic cell in an ATSC network. An ATSC cell coverage area may consist of one or more frequencies, depending on the number of frequencies used per Futurecast UTB system. If the value of the CELL_ID is not known or unspecified, this field is set to '0'.

NETWORK_ID: This is a 16-bit field which uniquely identifies the current ATSC network.

SYSTEM_ID: This 16-bit field uniquely identifies the Futurecast UTB system within the ATSC network. The Futurecast UTB system is the terrestrial broadcast system whose input is one or more input streams (TS, IP, GS) and whose output is an RF signal. The Futurecast UTB system carries one or more PHY profiles and FEF, if any. The same

TABLE 8

| | Current PHY_PROFILE = '000' (base) | Current PHY_PROFILE = '001' (handheld) | Current PHY_PROFILE = '010' (advanced) | Current PHY_PROFILE = '111' (FEF) |
|---|---|---|---|---|
| FRU_CONFIGURE = 000 | Only base profile present | Only handheld profile present | Only advanced profile present | Only FEF present |
| FRU_CONFIGURE = 1XX | Handheld profile present | Base profile present | Base profile present | Base profile present |
| FRU_CONFIGURE = X1X | Advanced profile present | Advanced profile present | Handheld profile present | Handheld profile present |
| FRU_CONFIGURE = XX1 | FEF present | FEF present | FEF present | Advanced profile present |

RESERVED: This 7-bit field is reserved for future use.

Figure 13:
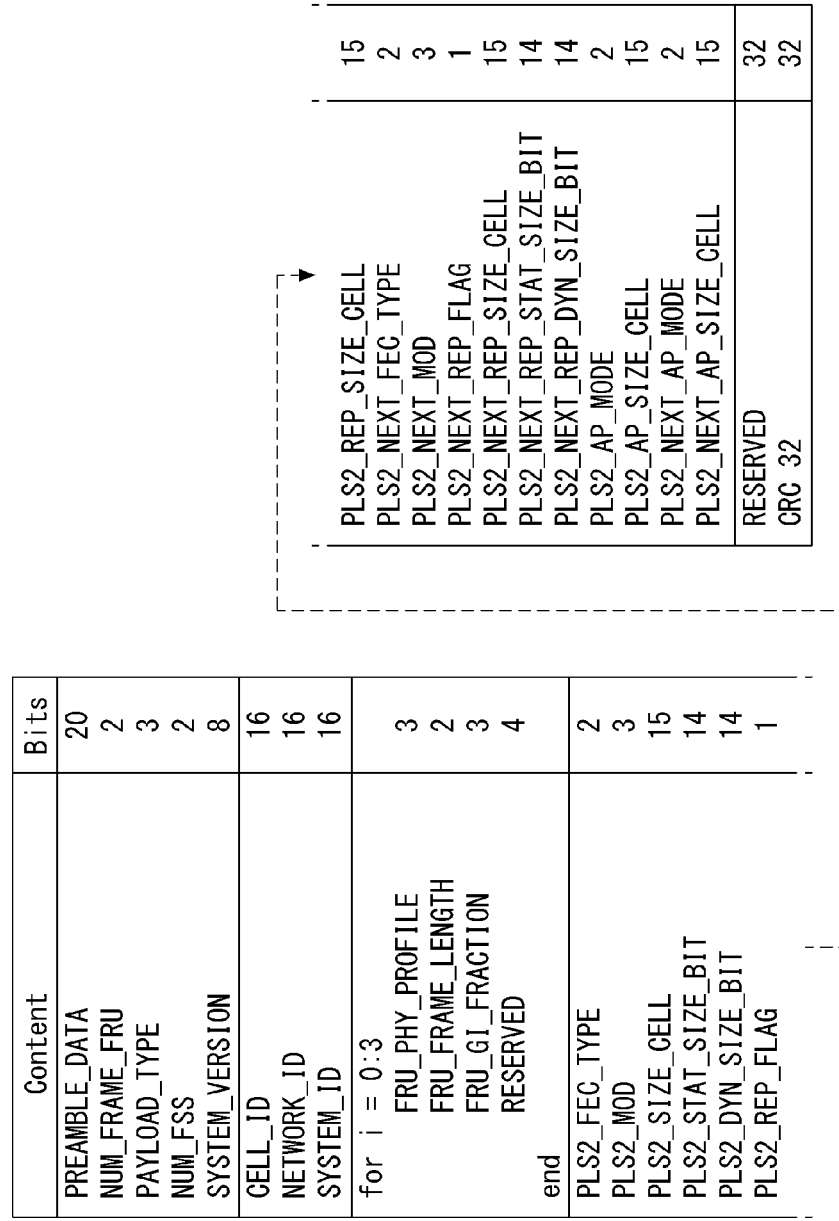
FIG. 13 illustrates PLS1 data according to an embodiment of the present invention.

FIG. 13 illustrates PLS1 data according to an embodiment of the present invention.

Futurecast UTB system may carry different input streams and use different RF frequencies in different geographical areas, allowing local service insertion. The frame structure and scheduling is controlled in one place and is identical for all transmissions within a Futurecast UTB system. One or more Futurecast UTB systems may have the same SYSTEM_ID meaning that they all have the same physical layer structure and configuration.

The following loop consists of FRU_PHY_PROFILE, FRU_FRAME_LENGTH, FRU_GI_FRACTION, and RESERVED which are used to indicate the FRU configuration and the length of each frame type. The loop size is fixed so that four PHY profiles (including a FEF) are signaled within the FRU. If NUM_FRAME_FRU is less than 4, the unused fields are filled with zeros.

FRU_PHY_PROFILE: This 3-bit field indicates the PHY profile type of the (i+1)th (i is the loop index) frame of the associated FRU. This field uses the same signaling format as shown in the table 8.

FRU_FRAME_LENGTH: This 2-bit field indicates the length of the (i+1)th frame of the associated FRU. Using FRU_FRAME_LENGTH together with FRU_GI_FRACTION, the exact value of the frame duration can be obtained.

FRU_GI_FRACTION: This 3-bit field indicates the guard interval fraction value of the (i+1)th frame of the associated FRU. FRU_GI_FRACTION is signaled according to the table 7.

RESERVED: This 4-bit field is reserved for future use.

The following fields provide parameters for decoding the PLS2 data.

PLS2_FEC_TYPE: This 2-bit field indicates the FEC type used by the PLS2 protection. The FEC type is signaled according to table 10. The details of the LDPC codes will be described later.

TABLE 10

| Content | PLS2 FEC type |
| --- | --- |
| 00 | 4K-1/4 and 7K-3/10 LDPC codes |
| 01~11 | Reserved |

PLS2_MOD: This 3-bit field indicates the modulation type used by the PLS2. The modulation type is signaled according to table 11.

TABLE 11

| Value | PLS2_MODE |
| --- | --- |
| 000 | BPSK |
| 001 | QPSK |
| 010 | QAM-16 |
| 011 | NUQ-64 |
| 100~111 | Reserved |

PLS2_SIZE_CELL: This 15-bit field indicates Ctotal_partial_block, the size (specified as the number of QAM cells) of the collection of full coded blocks for PLS2 that is carried in the current frame-group. This value is constant during the entire duration of the current frame-group.

PLS2_STAT_SIZE_BIT: This 14-bit field indicates the size, in bits, of the PLS2-STAT for the current frame-group. This value is constant during the entire duration of the current frame-group.

PLS2_DYN_SIZE_BIT: This 14-bit field indicates the size, in bits, of the PLS2-DYN for the current frame-group. This value is constant during the entire duration of the current frame-group.

PLS2_REP_FLAG: This 1-bit flag indicates whether the PLS2 repetition mode is used in the current frame-group. When this field is set to value '1', the PLS2 repetition mode is activated. When this field is set to value '0', the PLS2 repetition mode is deactivated.

PLS2_REP_SIZE_CELL: This 15-bit field indicates Ctotal_partial_block, the size (specified as the number of QAM cells) of the collection of partial coded blocks for PLS2 carried in every frame of the current frame-group, when PLS2 repetition is used. If repetition is not used, the value of this field is equal to 0. This value is constant during the entire duration of the current frame-group.

PLS2_NEXT_FEC_TYPE: This 2-bit field indicates the FEC type used for PLS2 that is carried in every frame of the next frame-group. The FEC type is signaled according to the table 10.

PLS2_NEXT_MOD: This 3-bit field indicates the modulation type used for PLS2 that is carried in every frame of the next frame-group. The modulation type is signaled according to the table 11.

PLS2_NEXT_REP_FLAG: This 1-bit flag indicates whether the PLS2 repetition mode is used in the next frame-group. When this field is set to value '1', the PLS2 repetition mode is activated. When this field is set to value '0', the PLS2 repetition mode is deactivated.

PLS2_NEXT_REP_SIZE_CELL: This 15-bit field indicates Ctotal_full_block, The size (specified as the number of QAM cells) of the collection of full coded blocks for PLS2 that is carried in every frame of the next frame-group, when PLS2 repetition is used. If repetition is not used in the next frame-group, the value of this field is equal to 0. This value is constant during the entire duration of the current frame-group.

PLS2_NEXT_REP_STAT_SIZE_BIT: This 14-bit field indicates the size, in bits, of the PLS2-STAT for the next frame-group. This value is constant in the current frame-group.

PLS2_NEXT_REP_DYN_SIZE_BIT: This 14-bit field indicates the size, in bits, of the PLS2-DYN for the next frame-group. This value is constant in the current frame-group.

PLS2_AP_MODE: This 2-bit field indicates whether additional parity is provided for PLS2 in the current frame-group. This value is constant during the entire duration of the current frame-group. The below table 12 gives the values of this field. When this field is set to '00', additional parity is not used for the PLS2 in the current frame-group.

TABLE 12

| Value | PLS2-AP mode |
| --- | --- |
| 00 | AP is not provided |
| 01 | AP1 mode |
| 10~11 | Reserved |

PLS2_AP_SIZE_CELL: This 15-bit field indicates the size (specified as the number of QAM cells) of the additional parity bits of the PLS2. This value is constant during the entire duration of the current frame-group.

PLS2_NEXT_AP_MODE: This 2-bit field indicates whether additional parity is provided for PLS2 signaling in every frame of next frame-group. This value is constant during the entire duration of the current frame-group. The table 12 defines the values of this field PLS2_NEXT_AP_SIZE_CELL: This 15-bit field indicates the size (specified as the number of QAM cells) of the additional parity bits of the PLS2 in every frame of the next frame-group. This value is constant during the entire duration of the current frame-group.

RESERVED: This 32-bit field is reserved for future use.

CRC_32: A 32-bit error detection code, which is applied to the entire PLS1 signaling.

FIG. 14 illustrates PLS2 data according to an embodiment of the present invention.

FIG. 14 illustrates PLS2-STAT data of the PLS2 data. The PLS2-STAT data are the same within a frame-group, while the PLS2-DYN data provide information that is specific for the current frame.

The details of fields of the PLS2-STAT data are as follows:

FIC_FLAG: This 1-bit field indicates whether the FIC is used in the current frame-group. If this field is set to '1', the FIC is provided in the current frame. If this field set to '0', the FIC is not carried in the current frame. This value is constant during the entire duration of the current frame-group.

AUX_FLAG: This 1-bit field indicates whether the auxiliary stream(s) is used in the current frame-group. If this field is set to '1', the auxiliary stream is provided in the current frame. If this field set to '0', the auxiliary stream is not carried in the current frame. This value is constant during the entire duration of current frame-group.

NUM_DP: This 6-bit field indicates the number of DPs carried within the current frame. The value of this field ranges from 1 to 64, and the number of DPs is NUM_DP+1.

DP_ID: This 6-bit field identifies uniquely a DP within a PHY profile.

DP_TYPE: This 3-bit field indicates the type of the DP. This is signaled according to the below table 13.

TABLE 13

| Value | DP Type |
|---|---|
| 000 | DP Type 1 |
| 001 | DP Type 2 |
| 010~111 | reserved |

DP_GROUP_ID: This 8-bit field identifies the DP group with which the current DP is associated. This can be used by a receiver to access the DPs of the service components associated with a particular service, which will have the same DP_GROUP_ID.

BASE_DP_ID: This 6-bit field indicates the DP carrying service signaling data (such as PSI/SI) used in the Management layer. The DP indicated by BASE_DP_ID may be either a normal DP carrying the service signaling data along with the service data or a dedicated DP carrying only the service signaling data DP_FEC_TYPE: This 2-bit field indicates the FEC type used by the associated DP. The FEC type is signaled according to the below table 14.

TABLE 14

| Value | FEC_TYPE |
|---|---|
| 00 | 16K LDPC |
| 01 | 64K LDPC |
| 10~11 | Reserved |

DP_COD: This 4-bit field indicates the code rate used by the associated DP. The code rate is signaled according to the below table 15.

TABLE 15

| Value | Code rate |
|---|---|
| 0000 | 5/15 |
| 0001 | 6/15 |
| 0010 | 7/15 |
| 0011 | 8/15 |
| 0100 | 9/15 |
| 0101 | 10/15 |
| 0110 | 11/15 |
| 0111 | 12/15 |
| 1000 | 13/15 |
| 1001~1111 | Reserved |

DP_MOD: This 4-bit field indicates the modulation used by the associated DP. The modulation is signaled according to the below table 16.

TABLE 16

| Value | Modulation |
|---|---|
| 0000 | QPSK |
| 0001 | QAM-16 |
| 0010 | NUQ-64 |
| 0011 | NUQ-256 |
| 0100 | NUQ-1024 |
| 0101 | NUC-16 |
| 0110 | NUC-64 |
| 0111 | NUC-256 |
| 1000 | NUC-1024 |
| 1001~1111 | reserved |

DP_SSD_FLAG: This 1-bit field indicates whether the SSD mode is used in the associated DP. If this field is set to value '1', SSD is used. If this field is set to value '0', SSD is not used.

The following field appears only if PHY_PROFILE is equal to '010', which indicates the advanced profile:

DP_MIMO: This 3-bit field indicates which type of MIMO encoding process is applied to the associated DP. The type of MIMO encoding process is signaled according to the table 17.

TABLE 17

| Value | MIMO encoding |
|---|---|
| 000 | FR-SM |
| 001 | FRFD-SM |
| 010~111 | reserved |

DP_TI_TYPE: This 1-bit field indicates the type of time-interleaving. A value of '0' indicates that one TI group corresponds to one frame and contains one or more TI-blocks. A value of '1' indicates that one TI group is carried in more than one frame and contains only one TI-block.

DP_TI_LENGTH: The use of this 2-bit field (the allowed values are only 1, 2, 4, 8) is determined by the values set within the DP_TI_TYPE field as follows:

If the DP_TI_TYPE is set to the value '1', this field indicates PI, the number of the frames to which each TI group is mapped, and there is one TI-block per TI group (NTI=1). The allowed PI values with 2-bit field are defined in the below table 18.

If the DP_TI_TYPE is set to the value '0', this field indicates the number of TI-blocks NTI per TI group, and there is one TI group per frame (Pi=1). The allowed PI values with 2-bit field are defined in the below table 18.

TABLE 18

| 2-bit field | PI | NTI |
|---|---|---|
| 00 | 1 | 1 |
| 01 | 2 | 2 |
| 10 | 4 | 3 |
| 11 | 8 | 4 |

DP_FRAME_INTERVAL: This 2-bit field indicates the frame interval (IJUMP) within the frame-group for the associated DP and the allowed values are 1, 2, 4, 8 (the corresponding 2-bit field is '00', '01', '10', or '11', respectively). For DPs that do not appear every frame of the frame-group, the value of this field is equal to the interval between successive frames. For example, if a DP appears on the frames 1, 5, 9, 13, etc., this field is set to '4'. For DPs that appear in every frame, this field is set to '1'.

DP_TI_BYPASS: This 1-bit field determines the availability of time interleaver 5050. If time interleaving is not used for a DP, it is set to '1'. Whereas if time interleaving is used it is set to '0'.

DP_FIRST_FRAME_IDX: This 5-bit field indicates the index of the first frame of the super-frame in which the current DP occurs. The value of DP_FIRST_FRAME_IDX ranges from 0 to 31

DP_NUM_BLOCK_MAX: This 10-bit field indicates the maximum value of DP_NUM_BLOCKS for this DP. The value of this field has the same range as DP_NUM_BLOCKS.

DP_PAYLOAD_TYPE: This 2-bit field indicates the type of the payload data carried by the given DP. DP_PAYLOAD_TYPE is signaled according to the below table 19.

TABLE 19

| Value | Payload Type |
|---|---|
| 00 | TS. |
| 01 | IP |
| 10 | GS |
| 11 | reserved |

DP_INBAND_MODE: This 2-bit field indicates whether the current DP carries in-band signaling information. The in-band signaling type is signaled according to the below table 20.

TABLE 20

| Value | In-band mode |
|---|---|
| 00 | In-band signaling is not carried. |
| 01 | INBAND-PLS is carried only |
| 10 | INBAND-ISSY is carried only |
| 11 | INBAND-PLS and INBAND-ISSY are carried |

DP_PROTOCOL_TYPE: This 2-bit field indicates the protocol type of the payload carried by the given DP. It is signaled according to the below table 21 when input payload types are selected.

TABLE 21

| Value | If DP_PAYLOAD_TYPE Is TS | If DP_PAYLOAD_TYPE Is IP | If DP_PAYLOAD_TYPE Is GS |
|---|---|---|---|
| 00 | MPEG2-TS | IPv4 | (Note) |
| 01 | Reserved | IPv6 | Reserved |
| 10 | Reserved | Reserved | Reserved |
| 11 | Reserved | Reserved | Reserved |

DP_CRC_MODE: This 2-bit field indicates whether CRC encoding is used in the Input Formatting block. The CRC mode is signaled according to the below table 22.

TABLE 22

| Value | CRC mode |
|---|---|
| 00 | Not used |
| 01 | CRC-8 |
| 10 | CRC-16 |
| 11 | CRC-32 |

DNP_MODE: This 2-bit field indicates the null-packet deletion mode used by the associated DP when DP_PAYLOAD_TYPE is set to TS ('00'). DNP_MODE is signaled according to the below table 23. If DP_PAYLOAD_TYPE is not TS ('00'), DNP_MODE is set to the value '00'.

TABLE 23

| Value | Null-packet deletion mode |
|---|---|
| 00 | Not used |
| 01 | DNP-NORMAL |
| 10 | DNP-OFFSET |
| 11 | reserved |

ISSY_MODE: This 2-bit field indicates the ISSY mode used by the associated DP when DP_PAYLOAD_TYPE is set to TS ('00'). The ISSY_MODE is signaled according to the below table 24 If DP_PAYLOAD_TYPE is not TS ('00'), ISSY_MODE is set to the value '00'.

TABLE 24

| Value | ISSY mode |
|---|---|
| 00 | Not used |
| 01 | ISSY-UP |
| 10 | ISSY-BBF |
| 11 | reserved |

HC_MODE_TS: This 2-bit field indicates the TS header compression mode used by the associated DP when DP_PAYLOAD_TYPE is set to TS ('00'). The HC_MODE_TS is signaled according to the below table 25.

TABLE 25

| Value | Header compression mode |
|---|---|
| 00 | HC_MODE_TS 1 |
| 01 | HC_MODE_TS 2 |
| 10 | HC_MODE_TS 3 |
| 11 | HC_MODE_TS 4 |

HC_MODE_IP: This 2-bit field indicates the IP header compression mode when DP_PAYLOAD_TYPE is set to IP ('01'). The HC_MODE_IP is signaled according to the below table 26.

TABLE 26

| Value | Header compression mode |
| --- | --- |
| 00 | No compression |
| 01 | HC_MODE_IP 1 |
| 10~11 | reserved |

PID: This 13-bit field indicates the PID number for TS header compression when DP_PAYLOAD_TYPE is set to TS ('00') and HC_MODE_TS is set to '01' or '10'.

RESERVED: This 8-bit field is reserved for future use.

The following field appears only if FIC_FLAG is equal to '1':

FIC_VERSION: This 8-bit field indicates the version number of the FIC.

FIC_LENGTH_BYTE: This 13-bit field indicates the length, in bytes, of the FIC.

RESERVED: This 8-bit field is reserved for future use.

The following field appears only if AUX_FLAG is equal to '1':

NUM_AUX: This 4-bit field indicates the number of auxiliary streams. Zero means no auxiliary streams are used.

AUX_CONFIG_RFU: This 8-bit field is reserved for future use.

AUX_STREAM_TYPE: This 4-bit is reserved for future use for indicating the type of the current auxiliary stream.

AUX_PRIVATE_CONFIG: This 28-bit field is reserved for future use for signaling auxiliary streams.

FIG. 15 illustrates PLS2 data according to another embodiment of the present invention.

FIG. 15 illustrates PLS2-DYN data of the PLS2 data. The values of the PLS2-DYN data may change during the duration of one frame-group, while the size of fields remains constant.

The details of fields of the PLS2-DYN data are as follows:

FRAME_INDEX: This 5-bit field indicates the frame index of the current frame within the super-frame. The index of the first frame of the super-frame is set to '0'.

PLS_CHANGE_COUNTER: This 4-bit field indicates the number of super-frames ahead where the configuration will change. The next super-frame with changes in the configuration is indicated by the value signaled within this field. If this field is set to the value '0000', it means that no scheduled change is foreseen: e.g., value '1' indicates that there is a change in the next super-frame.

FIC_CHANGE_COUNTER: This 4-bit field indicates the number of super-frames ahead where the configuration (i.e., the contents of the FIC) will change. The next super-frame with changes in the configuration is indicated by the value signaled within this field. If this field is set to the value '0000', it means that no scheduled change is foreseen: e.g. value '0001' indicates that there is a change in the next super-frame.

RESERVED: This 16-bit field is reserved for future use.

The following fields appear in the loop over NUM_DP, which describe the parameters associated with the DP carried in the current frame.

DP_ID: This 6-bit field indicates uniquely the DP within a PHY profile.

DP_START: This 15-bit (or 13-bit) field indicates the start position of the first of the DPs using the DPU addressing scheme. The DP_START field has differing length according to the PHY profile and FFT size as shown in the below table 27.

TABLE 27

| | DP_START field size | |
| --- | --- | --- |
| PHY profile | 64K | 16K |
| Base | 13 bit | 15 bit |
| Handheld | — | 13 bit |
| Advanced | 13 bit | 15 bit |

DP_NUM_BLOCK: This 10-bit field indicates the number of FEC blocks in the current TI group for the current DP. The value of DP_NUM_BLOCK ranges from 0 to 1023

RESERVED: This 8-bit field is reserved for future use.

The following fields indicate the FIC parameters associated with the EAC.

EAC_FLAG: This 1-bit field indicates the existence of the EAC in the current frame. This bit is the same value as the EAC_FLAG in the preamble.

EAS_WAKE_UP_VERSION_NUM: This 8-bit field indicates the version number of a wake-up indication.

If the EAC_FLAG field is equal to '1', the following 12 bits are allocated for EAC_LENGTH_BYTE field. If the EAC_FLAG field is equal to '0', the following 12 bits are allocated for EAC_COUNTER.

EAC_LENGTH_BYTE: This 12-bit field indicates the length, in byte, of the EAC.

EAC_COUNTER: This 12-bit field indicates the number of the frames before the frame where the EAC arrives.

The following field appears only if the AUX_FLAG field is equal to '1':

AUX_PRIVATE_DYN: This 48-bit field is reserved for future use for signaling auxiliary streams. The meaning of this field depends on the value of AUX_STREAM_TYPE in the configurable PLS2-STAT.

CRC_32: A 32-bit error detection code, which is applied to the entire PLS2.

Figure 16:
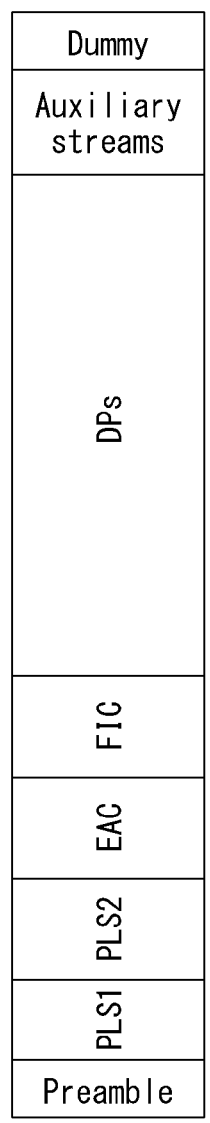
FIG. 16 illustrates a logical structure of a frame according to an embodiment of the present invention.

FIG. 16 illustrates a logical structure of a frame according to an embodiment of the present invention.

As above mentioned, the PLS, EAC, FIC, DPs, auxiliary streams and dummy cells are mapped into the active carriers of the OFDM symbols in the frame. The PLS1 and PLS2 are first mapped into one or more FSS(s). After that, EAC cells, if any, are mapped immediately following the PLS field, followed next by FIC cells, if any. The DPs are mapped next after the PLS or EAC, FIC, if any. Type 1 DPs follows first, and Type 2 DPs next. The details of a type of the DP will be described later. In some case, DPs may carry some special data for EAS or service signaling data. The auxiliary stream or streams, if any, follow the DPs, which in turn are followed by dummy cells. Mapping them all together in the above mentioned order, i.e. PLS, EAC, FIC, DPs, auxiliary streams and dummy data cells exactly fill the cell capacity in the frame.

Figure 17:
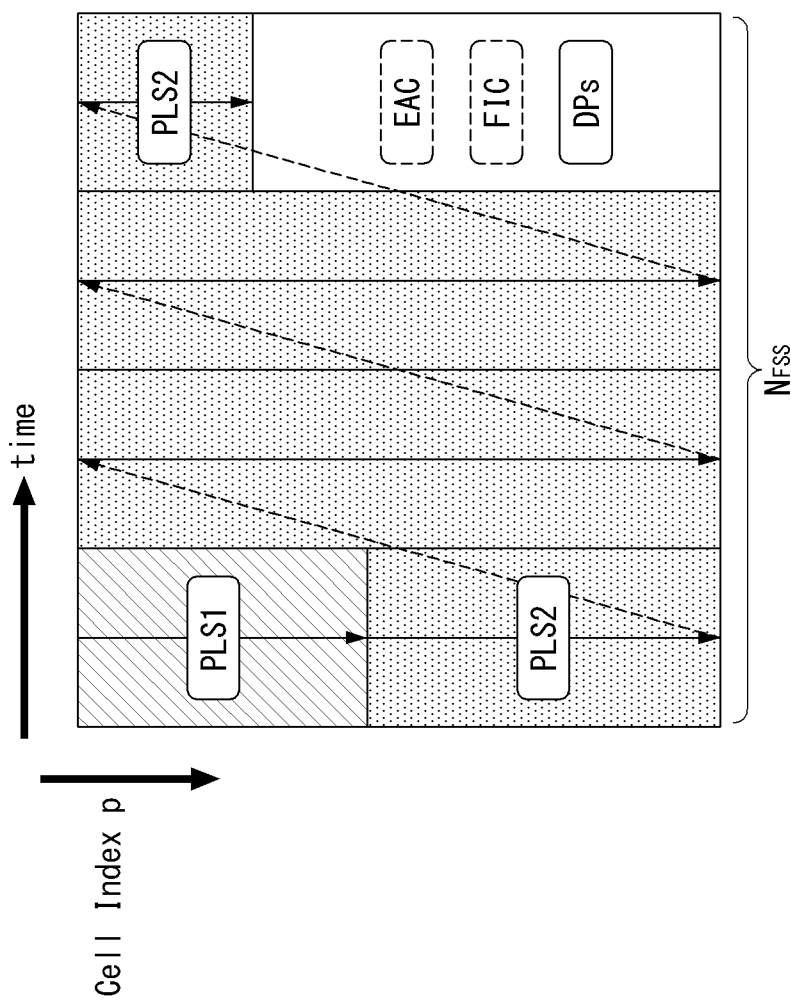
FIG. 17 illustrates PLS mapping according to an embodiment of the present invention.

FIG. 17 illustrates PLS mapping according to an embodiment of the present invention.

PLS cells are mapped to the active carriers of FSS(s). Depending on the number of cells occupied by PLS, one or more symbols are designated as FSS(s), and the number of FSS(s) N_FSS is signaled by NUM_FSS in PLS1. The FSS is a special symbol for carrying PLS cells. Since robustness and latency are critical issues in the PLS, the FSS(s) has higher density of pilots allowing fast synchronization and frequency-only interpolation within the FSS.

PLS cells are mapped to active carriers of the NFSS FSS(s) in a top-down manner as shown in an example in FIG. 17. The PLS1 cells are mapped first from the first cell of the first FSS in an increasing order of the cell index. The PLS2 cells follow immediately after the last cell of the PLS1 and mapping continues downward until the last cell index of the first FSS. If the total number of required PLS cells exceeds the number of active carriers of one FSS, mapping proceeds to the next FSS and continues in exactly the same manner as the first FSS.

After PLS mapping is completed, DPs are carried next. If EAC, FIC or both are present in the current frame, they are placed between PLS and "normal" DPs.

Figure 18:
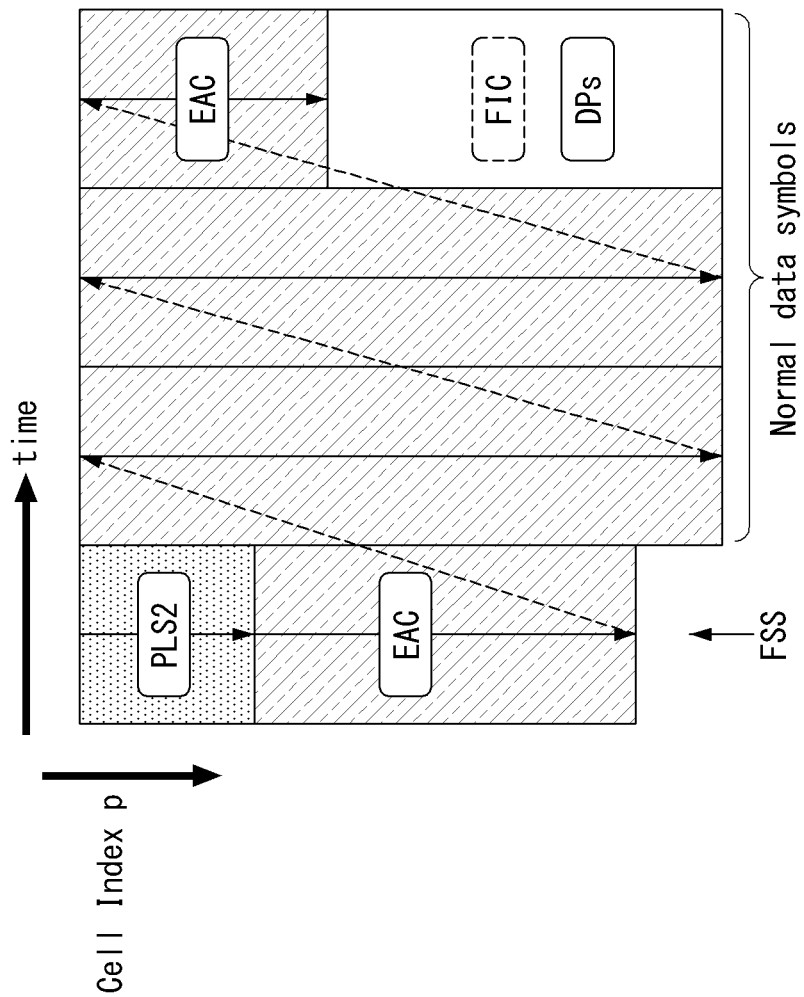
FIG. 18 illustrates EAC mapping according to an embodiment of the present invention.

FIG. 18 illustrates EAC mapping according to an embodiment of the present invention.

EAC is a dedicated channel for carrying EAS messages and links to the DPs for EAS. EAS support is provided but EAC itself may or may not be present in every frame. EAC, if any, is mapped immediately after the PLS2 cells. EAC is not preceded by any of the FIC, DPs, auxiliary streams or dummy cells other than the PLS cells. The procedure of mapping the EAC cells is exactly the same as that of the PLS.

The EAC cells are mapped from the next cell of the PLS2 in increasing order of the cell index as shown in the example in FIG. 18. Depending on the EAS message size, EAC cells may occupy a few symbols, as shown in FIG. 18.

EAC cells follow immediately after the last cell of the PLS2, and mapping continues downward until the last cell index of the last FSS. If the total number of required EAC cells exceeds the number of remaining active carriers of the last FSS mapping proceeds to the next symbol and continues in exactly the same manner as FSS(s). The next symbol for mapping in this case is the normal data symbol, which has more active carriers than a FSS.

After EAC mapping is completed, the FIC is carried next, if any exists. If FIC is not transmitted (as signaled in the PLS2 field), DPs follow immediately after the last cell of the EAC.

FIG. 19 illustrates FIC mapping according to an embodiment of the present invention.

(a) shows an example mapping of FIC cell without EAC and (b) shows an example mapping of FIC cell with EAC.

FIC is a dedicated channel for carrying cross-layer information to enable fast service acquisition and channel scanning. This information primarily includes channel binding information between DPs and the services of each broadcaster. For fast scan, a receiver can decode FIC and obtain information such as broadcaster ID, number of services, and BASE_DP_ID. For fast service acquisition, in addition to FIC, base DP can be decoded using BASE_DP_ID. Other than the content it carries, a base DP is encoded and mapped to a frame in exactly the same way as a normal DP. Therefore, no additional description is required for a base DP. The FIC data is generated and consumed in the Management Layer. The content of FIC data is as described in the Management Layer specification.

The FIC data is optional and the use of FIC is signaled by the FIC_FLAG parameter in the static part of the PLS2. If FIC is used, FIC_FLAG is set to '1' and the signaling field for FIC is defined in the static part of PLS2. Signaled in this field are FIC_VERSION, and FIC_LENGTH_BYTE. FIC uses the same modulation, coding and time interleaving parameters as PLS2. FIC shares the same signaling parameters such as PLS2_MOD and PLS2_FEC. FIC data, if any, is mapped immediately after PLS2 or EAC if any. FIC is not preceded by any normal DPs, auxiliary streams or dummy cells. The method of mapping FIC cells is exactly the same as that of EAC which is again the same as PLS.

Without EAC after PLS, FIC cells are mapped from the next cell of the PLS2 in an increasing order of the cell index as shown in an example in (a). Depending on the FIC data size, FIC cells may be mapped over a few symbols, as shown in (b).

FIC cells follow immediately after the last cell of the PLS2, and mapping continues downward until the last cell index of the last FSS. If the total number of required FIC cells exceeds the number of remaining active carriers of the last FSS, mapping proceeds to the next symbol and continues in exactly the same manner as FSS(s). The next symbol for mapping in this case is the normal data symbol which has more active carriers than a FSS.

If EAS messages are transmitted in the current frame, EAC precedes FIC, and FIC cells are mapped from the next cell of the EAC in an increasing order of the cell index as shown in (b).

After FIC mapping is completed, one or more DPs are mapped, followed by auxiliary streams, if any, and dummy cells.

Figure 20:
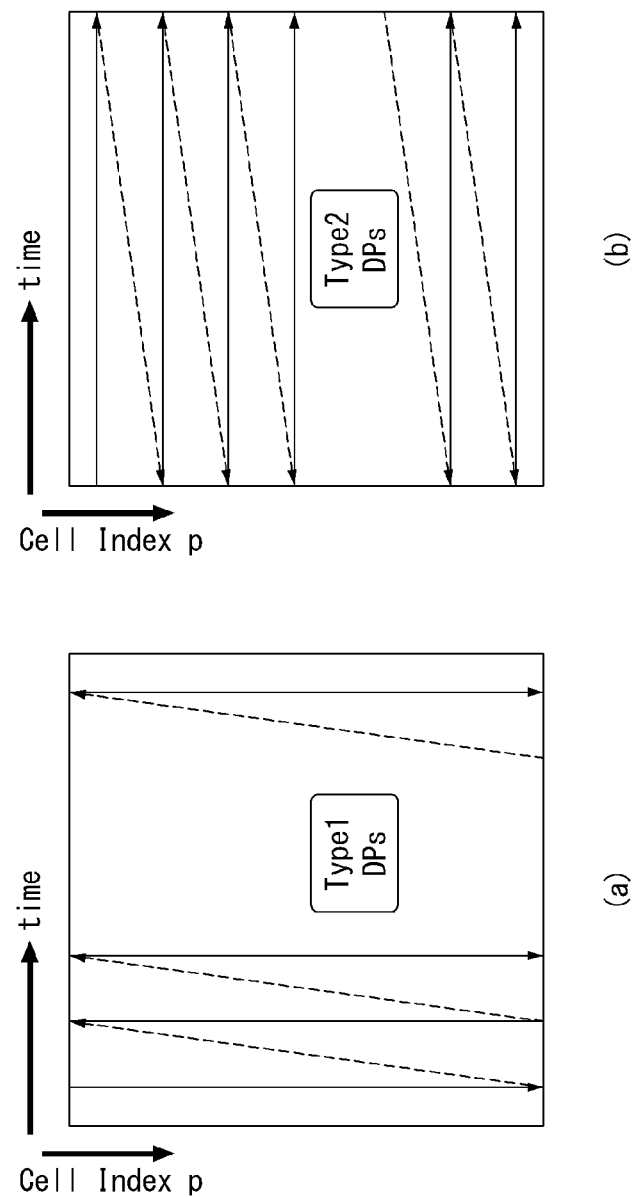
FIG. 20 illustrates a type of DP according to an embodiment of the present invention.

FIG. 20 illustrates a type of DP according to an embodiment of the present invention.

shows type 1 DP and (b) shows type 2 DP.

After the preceding channels, i.e., PLS, EAC and FIC, are mapped, cells of the DPs are mapped. A DP is categorized into one of two types according to mapping method:

Type 1 DP: DP is mapped by TDM
Type 2 DP: DP is mapped by FDM

The type of DP is indicated by DP_TYPE field in the static part of PLS2. FIG. 20 illustrates the mapping orders of Type 1 DPs and Type 2 DPs. Type 1 DPs are first mapped in the increasing order of cell index, and then after reaching the last cell index, the symbol index is increased by one. Within the next symbol, the DP continues to be mapped in the increasing order of cell index starting from p=0. With a number of DPs mapped together in one frame, each of the Type 1 DPs are grouped in time, similar to TDM multiplexing of DPs.

Type 2 DPs are first mapped in the increasing order of symbol index, and then after reaching the last OFDM symbol of the frame, the cell index increases by one and the symbol index rolls back to the first available symbol and then increases from that symbol index. After mapping a number of DPs together in one frame, each of the Type 2 DPs are grouped in frequency together, similar to FDM multiplexing of DPs.

Type 1 DPs and Type 2 DPs can coexist in a frame if needed with one restriction; Type 1 DPs always precede Type 2 DPs. The total number of OFDM cells carrying Type 1 and Type 2 DPs cannot exceed the total number of OFDM cells available for transmission of DPs:

$$D_{DP1}+D_{DP2} \leq D_{DP} \qquad \text{[Equation 2]}$$

where DDP1 is the number of OFDM cells occupied by Type 1 DPs, DDP2 is the number of cells occupied by Type 2 DPs. Since PLS, EAC, FIC are all mapped in the same way as Type 1 DP, they all follow "Type 1 mapping rule". Hence, overall, Type 1 mapping always precedes Type 2 mapping.

Figure 21:
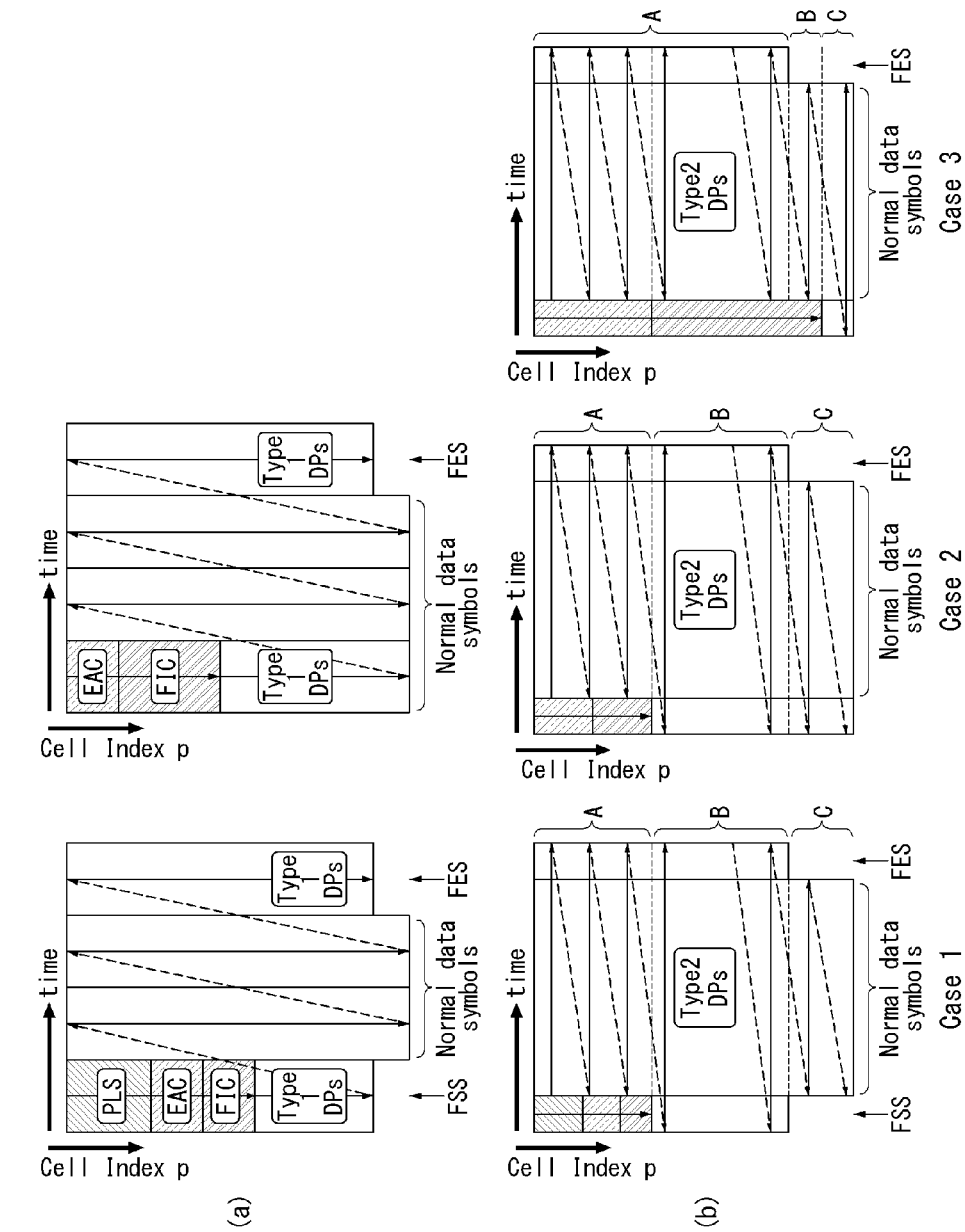
FIG. 21 illustrates DP mapping according to an embodiment of the present invention.

FIG. 21 illustrates DP mapping according to an embodiment of the present invention.

shows an addressing of OFDM cells for mapping type 1 DPs and (b) shows an addressing of OFDM cells for mapping for type 2 DPs.

Addressing of OFDM cells for mapping Type 1 DPs (0, . . . , DDP1-1) is defined for the active data cells of Type 1 DPs. The addressing scheme defines the order in which the cells from the TIs for each of the Type 1 DPs are allocated to the active data cells. It is also used to signal the locations of the DPs in the dynamic part of the PLS2.

Without EAC and FIC, address 0 refers to the cell immediately following the last cell carrying PLS in the last FSS. If EAC is transmitted and FIC is not in the corresponding frame, address 0 refers to the cell immediately following the last cell carrying EAC. If FIC is transmitted in the corresponding frame, address 0 refers to the cell immediately following the last cell carrying FIC. Address 0 for Type 1 DPs can be calculated considering two different cases as shown in (a). In the example in (a), PLS, EAC and FIC are assumed to be all transmitted. Extension to the cases where either or both of EAC and FIC are omitted is straightforward. If there are remaining cells in the FSS after mapping all the cells up to FIC as shown on the left side of (a).

Addressing of OFDM cells for mapping Type 2 DPs (0, . . . , DDP2-1) is defined for the active data cells of Type 2 DPs. The addressing scheme defines the order in which the cells from the TIs for each of the Type 2 DPs are allocated to the active data cells. It is also used to signal the locations of the DPs in the dynamic part of the PLS2.

Three slightly different cases are possible as shown in (b). For the first case shown on the left side of (b), cells in the last FSS are available for Type 2 DP mapping. For the second case shown in the middle, FIC occupies cells of a normal symbol, but the number of FIC cells on that symbol is not larger than CFSS. The third case, shown on the right side in (b), is the same as the second case except that the number of FIC cells mapped on that symbol exceeds CFSS.

The extension to the case where Type 1 DP(s) precede Type 2 DP(s) is straightforward since PLS, EAC and FIC follow the same "Type 1 mapping rule" as the Type 1 DP(s).

A data pipe unit (DPU) is a basic unit for allocating data cells to a DP in a frame.

A DPU is defined as a signaling unit for locating DPs in a frame. A Cell Mapper 7010 may map the cells produced by the TIs for each of the DPs. A Time interleaver 5050 outputs a series of TI-blocks and each TI-block comprises a variable number of XFECBLOCKs which is in turn composed of a set of cells. The number of cells in an XFECBLOCK, Ncells, is dependent on the FECBLOCK size, Nldpc, and the number of transmitted bits per constellation symbol. A DPU is defined as the greatest common divisor of all possible values of the number of cells in a XFECBLOCK, Ncells, supported in a given PHY profile. The length of a DPU in cells is defined as LDPU. Since each PHY profile supports different combinations of FECBLOCK size and a different number of bits per constellation symbol, LDPU is defined on a PHY profile basis.

Figure 22:
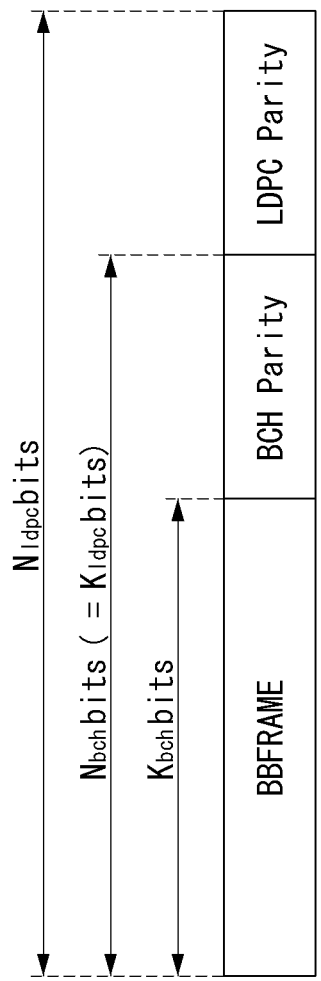
FIG. 22 illustrates an FEC structure according to an embodiment of the present invention.

FIG. 22 illustrates an FEC structure according to an embodiment of the present invention.

FIG. 22 illustrates an FEC structure according to an embodiment of the present invention before bit interleaving. As above mentioned, Data FEC encoder may perform the FEC encoding on the input BBF to generate FECBLOCK procedure using outer coding (BCH), and inner coding (LDPC). The illustrated FEC structure corresponds to the FECBLOCK. Also, the FECBLOCK and the FEC structure have same value corresponding to a length of LDPC codeword.

The BCH encoding is applied to each BBF (Kbch bits), and then LDPC encoding is applied to BCH-encoded BBF (Kldpc bits=Nbch bits) as illustrated in FIG. 22.

The value of Nldpc is either 64800 bits (long FECBLOCK) or 16200 bits (short FECBLOCK).

The below table 28 and table 29 show FEC encoding parameters for a long FECBLOCK and a short FECBLOCK, respectively.

TABLE 28

| LDPC Rate | Nldpc | Kldpc | Kbch | BCH error correction capability | Nbch − Kbch |
|---|---|---|---|---|---|
| 5/15 | 64800 | 21600 | 21408 | 12 | 192 |
| 6/15 | | 25920 | 25728 | | |
| 7/15 | | 30240 | 30048 | | |
| 8/15 | | 34560 | 34368 | | |
| 9/15 | | 38880 | 38688 | | |
| 10/15 | | 43200 | 43008 | | |
| 11/15 | | 47520 | 47328 | | |
| 12/15 | | 51840 | 51648 | | |
| 13/15 | | 56160 | 55968 | | |

TABLE 29

| LDPC Rate | Nldpc | Kldpc | Kbch | BCH error correction capability | Nbch − Kbch |
|---|---|---|---|---|---|
| 5/15 | 16200 | 5400 | 5232 | 12 | 168 |
| 6/15 | | 6480 | 6312 | | |
| 7/15 | | 7560 | 7392 | | |
| 8/15 | | 8640 | 8472 | | |
| 9/15 | | 9720 | 9552 | | |
| 10/15 | | 10800 | 10632 | | |
| 11/15 | | 11880 | 11712 | | |
| 12/15 | | 12960 | 12792 | | |
| 13/15 | | 14040 | 13872 | | |

The details of operations of the BCH encoding and LDPC encoding are as follows:

A 12-error correcting BCH code is used for outer encoding of the BBF. The BCH generator polynomial for short FECBLOCK and long FECBLOCK are obtained by multiplying together all polynomials.

LDPC code is used to encode the output of the outer BCH encoding. To generate a completed Bldpc (FECBLOCK), Pldpc (parity bits) is encoded systematically from each Ildpc (BCH-encoded BBF), and appended to Ildpc. The completed Bldpc (FECBLOCK) are expressed as follow Equation.

$$B_{ldpc} = [I_{ldpc} P_{ldpc}] = [i_0, i_1, \ldots, i_{K_{ldpc}-1}, p_0, p_1, \ldots, p_{N_{ldpc}-K_{ldpc}-1}]$$ [Equation 3]

The parameters for long FECBLOCK and short FECBLOCK are given in the above table 28 and 29, respectively.

The detailed procedure to calculate Nldpc−Kldpc parity bits for long FECBLOCK, is as follows:

1) Initialize the parity bits, $$p_0 = p_1 = p_2 = \ldots = p_{N_{ldpc}-K_{ldpc}-1} = 0$$ [Equation 4]

2) Accumulate the first information bit—i0, at parity bit addresses specified in the first row of an addresses of parity check matrix. The details of addresses of parity check matrix will be described later. For example, for rate 13/15:

$$p_{983} = p_{983} \oplus i_0$$

$$p_{2814} = p_{2815} \oplus i_0$$

$$p_{4837} = p_{4837} \oplus i_0$$

$$p_{4989} = p_{4989} \oplus i_0$$

$$p_{6138} = p_{6138} \oplus i_0$$

$$p_{6458} = p_{6458} \oplus i_0$$

$$p_{6921} = p_{6921} \oplus i_0$$

$p_{6974} = p_{6974} \oplus i_0$ $p_{7572} = p_{7572} \oplus i_0$ $p_{8260} = p_{8260} \oplus i_0$ $p_{8496} = p_{8496} \oplus i_0$ [Equation 5]

3) For the next 359 information bits, is, s=1, 2, ..., 359 accumulate is at parity bit addresses using following Equation.

$\{x + (s \bmod 360) \times Q_{ldpc}\} \bmod(N_{ldpc} - K_{ldpc})$ [Equation 6]

where x denotes the address of the parity bit accumulator corresponding to the first bit i0, and Qldpc is a code rate dependent constant specified in the addresses of parity check matrix. Continuing with the example, Qldpc=24 for rate 13/15, so for information bit i1, the following operations are performed:

$p_{1007} = p_{1007} \oplus i_1$ $p_{2839} = p_{2839} \oplus i_1$ $p_{4861} = p_{4861} \oplus i_1$ $p_{5013} = p_{5013} \oplus i_1$ $p_{6162} = p_{6162} \oplus i_1$ $p_{6482} = p_{6482} \oplus i_1$ $p_{6945} = p_{6945} \oplus i_1$ $p_{6998} = p_{6998} \oplus i_1$ $p_{7596} = p_{7596} \oplus i_1$ $p_{8284} = p_{8284} \oplus i_1$ $p_{8520} = p_{8520} \oplus i_1$ [Equation 7]

4) For the 361st information bit i360, the addresses of the parity bit accumulators are given in the second row of the addresses of parity check matrix. In a similar manner the addresses of the parity bit accumulators for the following 359 information bits is, s=361, 362, ..., 719 are obtained using the Equation 6, where x denotes the address of the parity bit accumulator corresponding to the information bit i360, i.e., the entries in the second row of the addresses of parity check matrix.

5) In a similar manner, for every group of 360 new information bits, a new row from addresses of parity check matrixes used to find the addresses of the parity bit accumulators.

After all of the information bits are exhausted, the final parity bits are obtained as follows:

6) Sequentially perform the following operations starting with i=1

$p_i = p_i \oplus p_{i-1}, i=1,2,\ldots,N_{ldpc} - K_{ldpc} - 1$ [Equation 8]

where final content of pi, i=0, 1, ... Nldpc−Kldpc−1 is equal to the parity bit pi.

TABLE 30

| Code Rate | Qldpc |
|---|---|
| 5/15 | 120 |
| 6/15 | 108 |
| 7/15 | 96 |
| 8/15 | 84 |

TABLE 30-continued

| Code Rate | Qldpc |
|---|---|
| 9/15 | 72 |
| 10/15 | 60 |
| 11/15 | 48 |
| 12/15 | 36 |
| 13/15 | 24 |

This LDPC encoding procedure for a short FECBLOCK is in accordance with t LDPC encoding procedure for the long FECBLOCK, except replacing the table 30 with table 31, and replacing the addresses of parity check matrix for the long FECBLOCK with the addresses of parity check matrix for the short FECBLOCK.

TABLE 31

| Code Rate | Qldpc |
|---|---|
| 5/15 | 30 |
| 6/15 | 27 |
| 7/15 | 24 |
| 8/15 | 21 |
| 9/15 | 18 |
| 10/15 | 15 |
| 11/15 | 12 |
| 12/15 | 9 |
| 13/15 | 6 |

Figure 23:
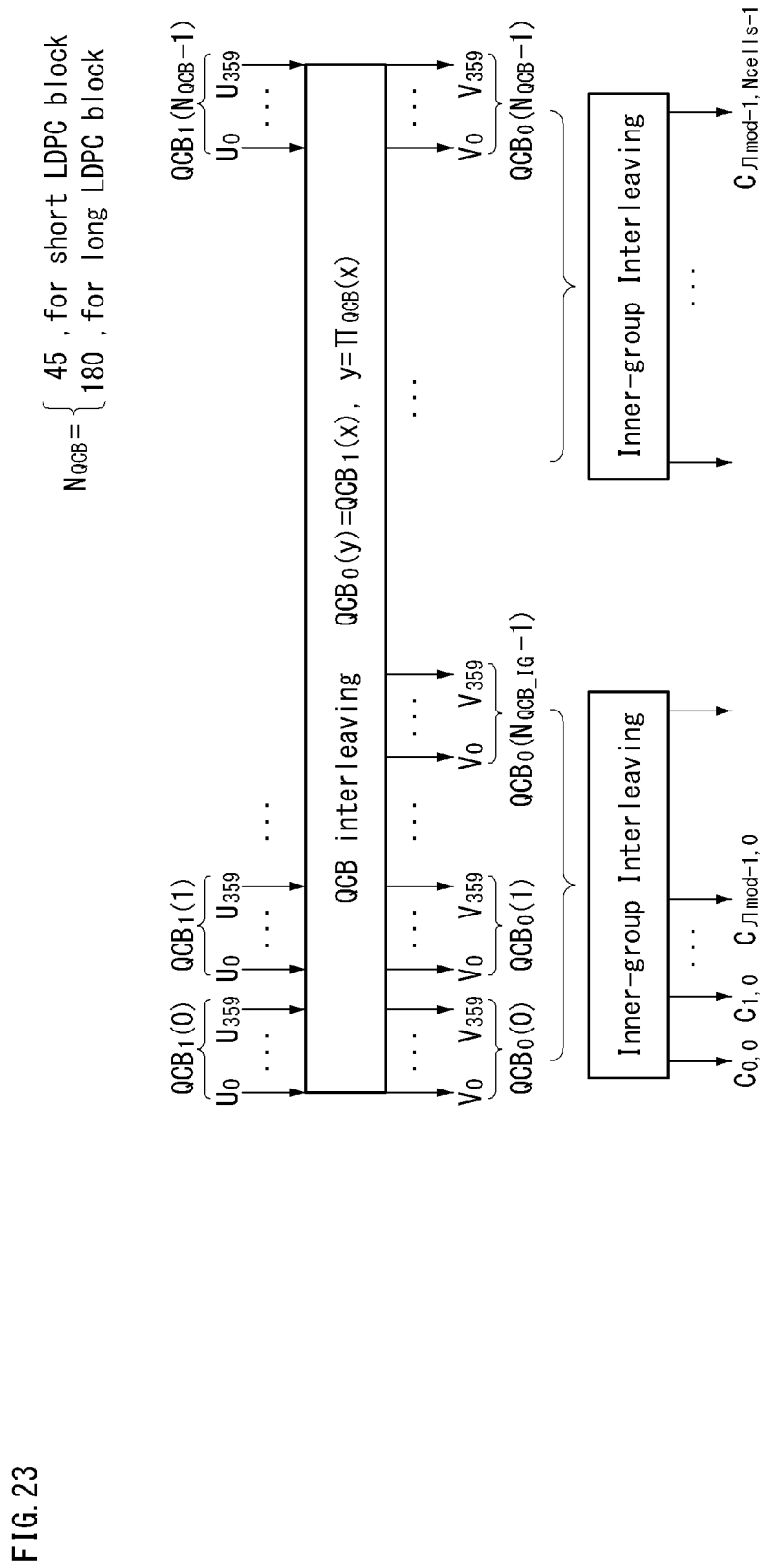
FIG. 23 illustrates a bit interleaving according to an embodiment of the present invention.

FIG. 23 illustrates a bit interleaving according to an embodiment of the present invention.

The outputs of the LDPC encoder are bit-interleaved, which consists of parity interleaving followed by Quasi-Cyclic Block (QCB) interleaving and inner-group interleaving.

shows Quasi-Cyclic Block (QCB) interleaving and (b) shows inner-group interleaving.

The FECBLOCK may be parity interleaved. At the output of the parity interleaving, the LDPC codeword consists of 180 adjacent QC blocks in a long FECBLOCK and 45 adjacent QC blocks in a short FECBLOCK. Each QC block in either a long or short FECBLOCK consists of 360 bits. The parity interleaved LDPC codeword is interleaved by QCB interleaving. The unit of QCB interleaving is a QC block. The QC blocks at the output of parity interleaving are permutated by QCB interleaving as illustrated in FIG. 23, where Ncells=64800/η mod or 16200/η mod according to the FECBLOCK length. The QCB interleaving pattern is unique to each combination of modulation type and LDPC code rate.

After QCB interleaving, inner-group interleaving is performed according to modulation type and order (η mod) which is defined in the below table 32. The number of QC blocks for one inner-group, NQCB_IG, is also defined.

TABLE 32

| Modulation type | ηmod | NQCB_IG |
|---|---|---|
| QAM-16 | 4 | 2 |
| NUC-16 | 4 | 4 |
| NUQ-64 | 6 | 3 |
| NUC-64 | 6 | 6 |
| NUQ-256 | 8 | 4 |
| NUC-256 | 8 | 8 |
| NUQ-1024 | 10 | 5 |
| NUC-1024 | 10 | 10 |

The inner-group interleaving process is performed with NQCB_IG QC blocks of the QCB interleaving output. Inner-group interleaving has a process of writing and reading the bits of the inner-group using 360 columns and NQCB_IG rows. In the write operation, the bits from the QCB interleaving output are written row-wise. The read operation is performed column-wise to read out m bits from each row, where m is equal to 1 for NUC and 2 for NUQ.

Figure 24:
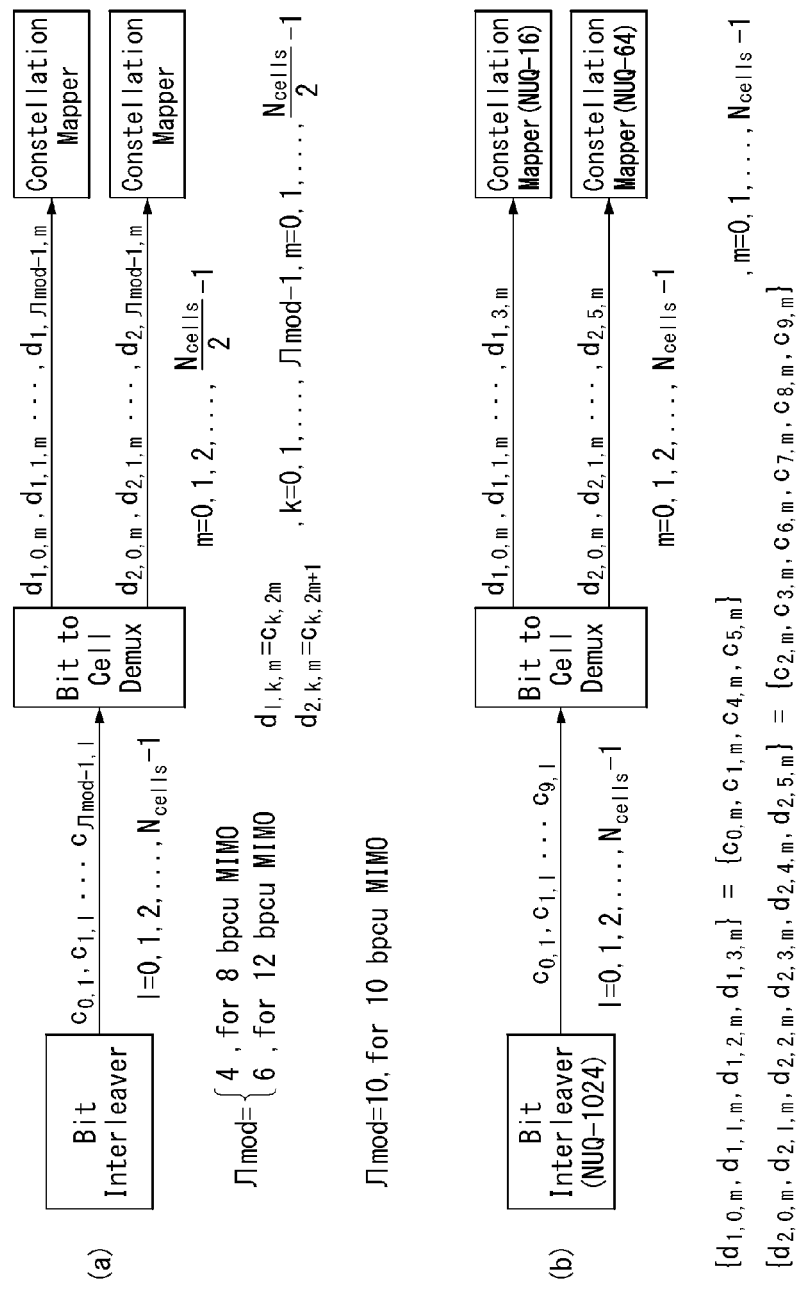
FIG. 24 illustrates a cell-word demultiplexing according to an embodiment of the present invention.

FIG. 24 illustrates a cell-word demultiplexing according to an embodiment of the present invention.

shows a cell-word demultiplexing for 8 and 12 bpcu MIMO and (b) shows a cell-word demultiplexing for 10 bpcu MIMO.

Each cell word ($c0,1, c1,1, \ldots, c\eta \bmod{-1},1$) of the bit interleaving output is demultiplexed into ($d1,0,m, d1,1,m \ldots, d1,\eta \bmod{-1},m$) and ($d2,0,m, d2,1,m \ldots, d2,\eta \bmod{-1},m$) as shown in (a), which describes the cell-word demultiplexing process for one XFECBLOCK.

For the 10 bpcu MIMO case using different types of NUQ for MIMO encoding, the Bit Interleaver for NUQ-1024 is re-used. Each cell word ($c0,1, c1,1, \ldots, c9,1$) of the Bit Interleaver output is demultiplexed into ($d1,0,m, d1,1,m \ldots, d1,3,m$) and ($d2,0,m, d2,1,m \ldots, d2,5,m$), as shown in (b).

Figure 25:
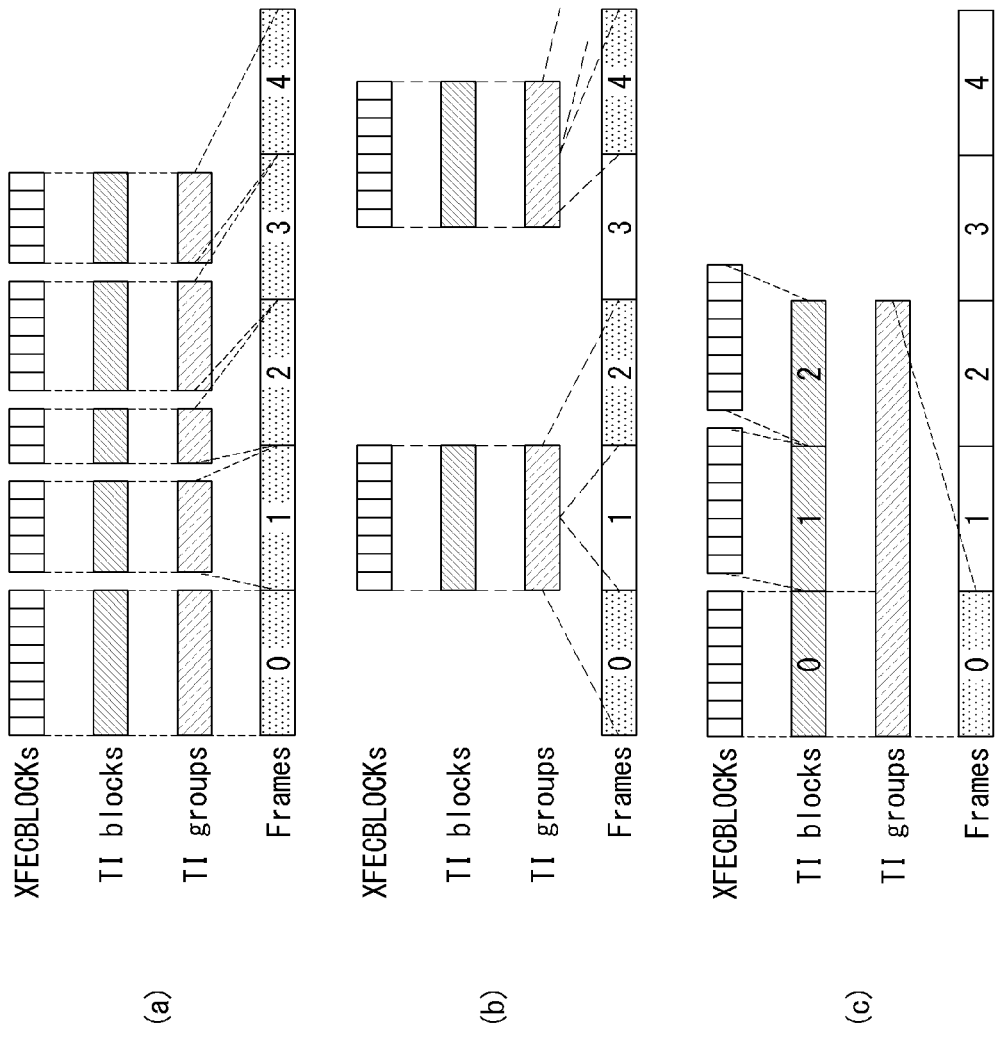
FIG. 25 illustrates a time interleaving according to an embodiment of the present invention.

FIG. 25 illustrates a time interleaving according to an embodiment of the present invention.

(a) to (c) show examples of TI mode.

The time interleaver operates at the DP level. The parameters of time interleaving (TI) may be set differently for each DP.

The following parameters, which appear in part of the PLS2-STAT data, configure the TI:

DP_TI_TYPE (allowed values: 0 or 1): Represents the TI mode; '0' indicates the mode with multiple TI blocks (more than one TI block) per TI group. In this case, one TI group is directly mapped to one frame (no inter-frame interleaving). '1' indicates the mode with only one TI block per TI group. In this case, the TI block may be spread over more than one frame (inter-frame interleaving).

DP_TI_LENGTH: If DP_TI_TYPE='0', this parameter is the number of TI blocks NTI per TI group. For DP_TI_TYPE='1', this parameter is the number of frames PI spread from one TI group.

DP_NUM_BLOCK_MAX (allowed values: 0 to 1023): Represents the maximum number of XFECBLOCKs per TI group.

DP_FRAME_INTERVAL (allowed values: 1, 2, 4, 8): Represents the number of the frames IJUMP between two successive frames carrying the same DP of a given PHY profile.

DP_TI_BYPASS (allowed values: 0 or 1): If time interleaving is not used for a DP, this parameter is set to '1'. It is set to '0' if time interleaving is used.

Additionally, the parameter DP_NUM_BLOCK from the PLS2-DYN data is used to represent the number of XFECBLOCKs carried by one TI group of the DP.

When time interleaving is not used for a DP, the following TI group, time interleaving operation, and TI mode are not considered. However, the Delay Compensation block for the dynamic configuration information from the scheduler will still be required. In each DP, the XFECBLOCKs received from the SSD/MIMO encoding are grouped into TI groups. That is, each TI group is a set of an integer number of XFECBLOCKs and will contain a dynamically variable number of XFECBLOCKs. The number of XFECBLOCKs in the TI group of index n is denoted by NxBLOCK_Group(n) and is signaled as DP_NUM_BLOCK in the PLS2-DYN data. Note that NxBLOCK_Group(n) may vary from the minimum value of 0 to the maximum value NxBLOCK_Group MAX (corresponding to DP_NUM_BLOCK_MAX) of which the largest value is 1023.

Each TI group is either mapped directly onto one frame or spread over PI frames. Each TI group is also divided into more than one TI blocks(NTI), where each TI block corresponds to one usage of time interleaver memory. The TI blocks within the TI group may contain slightly different numbers of XFECBLOCKs. If the TI group is divided into multiple TI blocks, it is directly mapped to only one frame. There are three options for time interleaving (except the extra option of skipping the time interleaving) as shown in the below table 33.

TABLE 33

| Mode | Description |
| --- | --- |
| Option-1 | Each TI group contains one TI block and is mapped directly to one frame as shown in (a). This option is signaled in the PLS2-STAT by DP_TI_TYPE = '0' and DP_TI_LENGTH = '1' ($N_{TI}$ = 1). |
| Option-2 | Each TI group contains one TI block and is mapped to more than one frame. (b) shows an example, where one TI group is mapped to two frames, i.e., DP_TI_LENGTH = '2' ($P_I$ = 2) and DP_FRAME_INTERVAL ($I_{JUMP}$ = 2). This provides greater time diversity for low data-rate services. This option is signaled in the PLS2-STAT by DP_TI_TYPE = '1'. |
| Option-3 | Each TI group is divided into multiple TI blocks and is mapped directly to one frame as shown in (c). Each TI block may use full TI memory, so as to provide the maximum bit-rate for a DP. This option is signaled in the PLS2-STAT signaling by DP_TI_TYPE = '0' and DP_TI_LENGTH = NTI, while $P_I$ = 1. |

In each DP, the TI memory stores the input XFEC-BLOCKs (output XFECBLOCKs from the SSD/MIMO encoding block). Assume that input XFECBLOCKs are defined as $$(d_{n,s,0,0}, d_{n,s,0,1}, \ldots, d_{n,s,0,N_{cells}-1}, d_{n,s,1,0}, \ldots,$$
$$d_{n,s,1,N_{cells}-1}, \ldots, d_{n,s,N_{xBLOCK\_TI}(n,s)-1,0}, \ldots,$$
$$d_{n,s,N_{xBLOCK\_TI}(n,s)-1,N_{cells}-1}),$$

where $d_{n,s,r,q}$ is the qth cell of the rth XFECBLOCK in the sth TI block of the nth TI group and represents the outputs of SSD and MIMO encodings as follows $$d_{n,s,r,q} = \begin{cases} f_{n,s,r,q}, & \text{the output of } SSD \text{ encoding} \\ g_{n,s,r,q}, & \text{the output of } MIMO \text{ encoding} \end{cases}.$$

In addition, assume that output XFECBLOCKs from the time interleaver 5050 are defined as $$(h_{n,s,0}, h_{n,s,1}, \ldots, h_{n,s,i}, \ldots, h_{n,s,N_{xBLOCK\_TI}(n,s) \times N_{cells}-1})$$

where $h_{n,s,i}$ is the ith output cell (for $i=0, \ldots, N_{xBLOCK\_TI}(n,s) \times N_{cells}-1$) in the sth TI block of the nth TI group.

Typically, the time interleaver will also act as a buffer for DP data prior to the process of frame building. This is achieved by means of two memory banks for each DP. The first TI-block is written to the first bank. The second TI-block is written to the second bank while the first bank is being read from and so on.

The TI is a twisted row-column block interleaver. For the sth TI block of the nth TI group, the number of rows $N_r$ of a TI memory is equal to the number of cells $N_{cells}$, i.e., $N_r = N_{cells}$ while the number of columns $N_c$ is equal to the number $N_{xBLOCK\_TI}(n,s)$ Hereinafter, the input formatting module/step and output formatting module/step in the method of transmitting and receiving a broadcast signal described above will be described additionally.

As described above with reference to FIG. 1, the input formatting module of the broadcast transmitter may demultiplex an input stream to at least one data pipe (DP) and the input stream may be input as IP streams/packets, MPEG-2 TS, or a type of generic stream. Also, as illustrated in FIGS. 2 through 4, the input formatting module may include a mode adaptation module and a stream adaptation module. As illustrated in FIGS. 2 and 3, the mode adaptation module slices input data stream and insert the same to a data field of a baseband (BB) frame. Hereinafter, operations of a broadcast signal transmitter and a broadcast signal receiver in a case in which input and output streams are IP streams will be described. In the present disclosure, the broadcast signal transmitter may also be referred to as a broadcast transmitter or a broadcast signal transmission apparatus and the broadcast signal receiver may also be referred to as a broadcast receiver or a broadcast signal reception apparatus.

Figure 26:
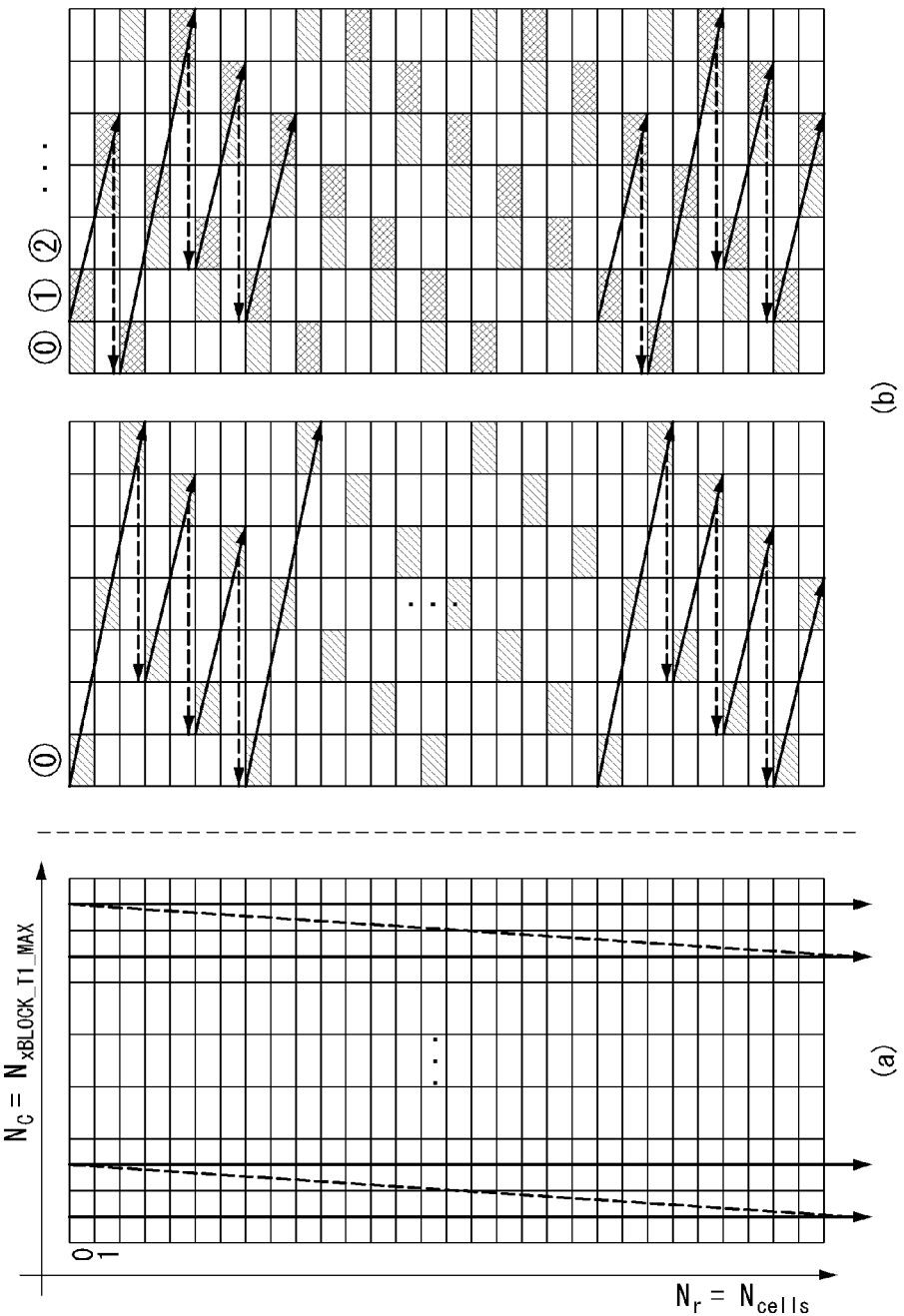
FIG. 26 illustrates a basic operation of a twisted row-column block interleaver according to an exemplary embodiment of the present invention.

FIG. 26 illustrates a basic operation of a twisted row-column block interleaver according to an exemplary embodiment of the present invention.

FIG. 26A illustrates a writing operation in a time interleaver and FIG. 26B illustrates a reading operation in the time interleaver. As illustrated in FIG. 26A, a first XFECBLOCK is written in a first column of a time interleaving memory in a column direction and a second XFECBLOCK is written in a next column, and such an operation is continued. In addition, in an interleaving array, a cell is read in a diagonal direction. As illustrated in FIG. 26B, while the diagonal reading is in progress from a first row (to a right side along the row starting from a leftmost column) to a last row, $N_r$ cells are read. In detail, when it is assumed that $z_{n,s,i}(i=0, \ldots, N_r N_c)$ is a time interleaving memory cell position to be sequentially read, the reading operation in the interleaving array is executed by calculating a row index $R_{n,s,i}$, a column index $C_{n,s,i}$, and associated twist parameter $T_{n,s,i}$ as shown in an equation given below.

$$\text{GENERATE}(R_{n,s,i}, C_{n,s,i}) = \quad [\text{Equation 9}]$$
$$\{$$
$$R_{n,s,i} = \text{mod}(i, N_r),$$
$$T_{n,s,i} = \text{mod}(S_{shift} \times R_{n,s,i}, N_c),$$
$$C_{n,s,i} = \text{mod}\left(T_{n,s,i} + \left\lfloor \frac{i}{N_t} \right\rfloor, N_c\right)$$
$$\}$$

Where, $S_{shift}$ is a common shift value for a diagonal reading process regardless of $N_{xBLOCK\_TI}(n,s)$ and the shift value is decided by $N_{xBLOCK\_TI\_MAX}$ given in PLS2-STAT as shown in an equation given below.

[Equation 10]

for $$\begin{cases} N'_{xBLOCK\_TI\_MAX} = N_{xBLOCK\_TI\_MAX} + 1, & \text{if } N_{xBLOCK\_TI\_MAX} \text{mod} 2 = 0 \\ N'_{xBLOCK\_TI\_MAX} = N_{xBLOCK\_TI\_MAX}, & \text{if } N_{xBLOCK\_TI\_MAX} \text{mod} 2 = 1 \end{cases},$$

$$S_{shift} = \frac{N'_{xBLOCK\_TI\_MAX} - 1}{2}$$

Consequently, the cell position to be read is calculated by a coordinate $z_{n,s,i} = N_r C_{n,s,i} + R_{n,s,i}$.

Figure 27:
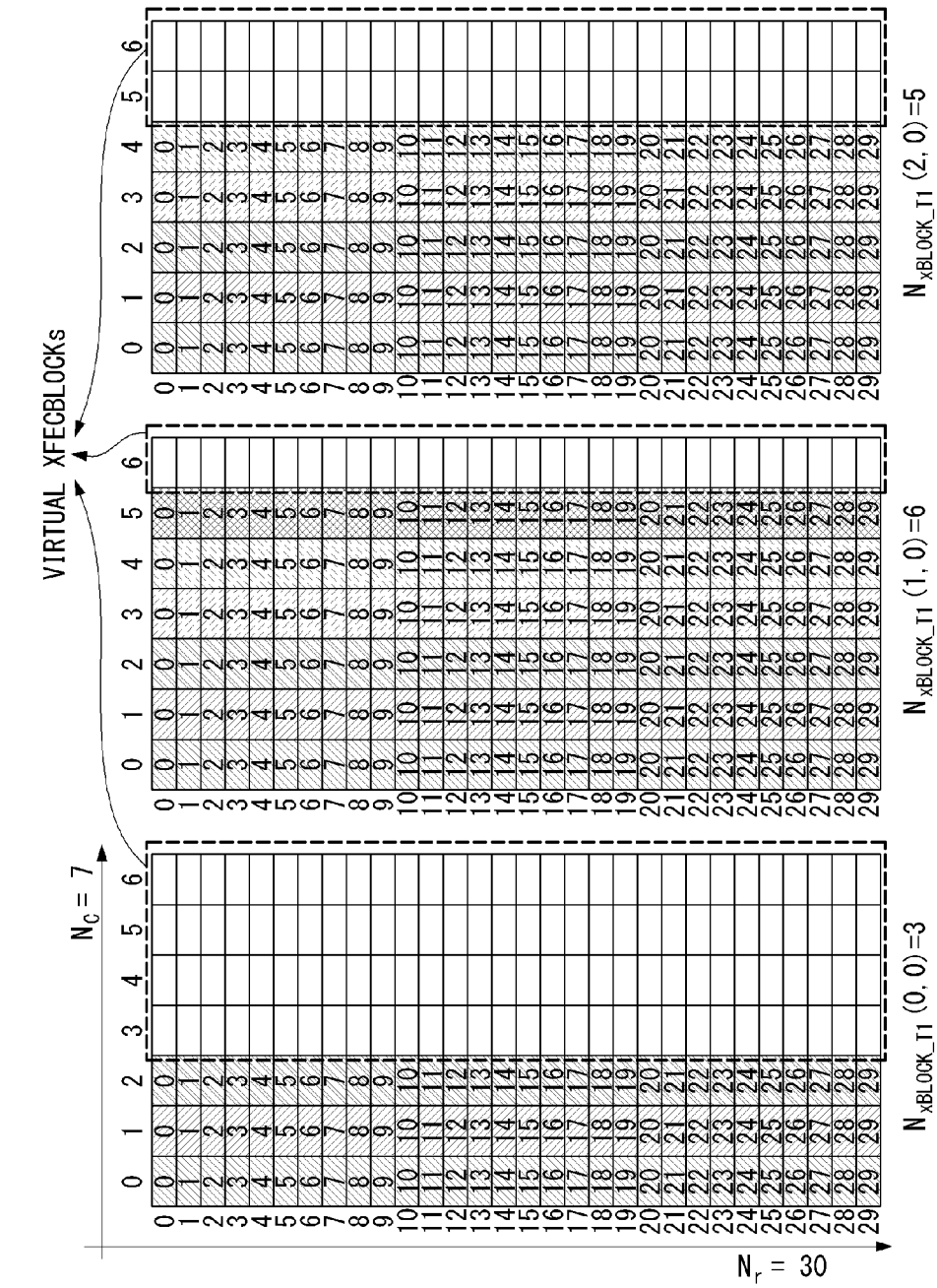
FIG. 27 illustrates an operation of a twisted row-column block interleaver according to another exemplary embodiment of the present invention.

FIG. 27 illustrates an operation of a twisted row-column block interleaver according to another exemplary embodiment of the present invention.

In more detail, FIG. 27 illustrates an interleaving array in the time interleaving memory for respective time interleaving groups including a virtual XFECBLOCK when $N_{xBLOCK\_TI}(0,0)=3$, $N_{xBLOCK\_TI}(1,0)=6$, and $N_{xBLOCK\_TI}(2,0)=5$.

A variable $N_{xBLOCK\_TI}(n,x)=N_r$ will be equal to or smaller than $N_{xBLOCK\_TI\_MAX}$. Accordingly, in order for a receiver to achieve single memory interleaving regardless of $N_{xBLOCK\_TI}(n,s)$, the size of the interleaving array for the twisted row-column block interleaver is set to a size of $N_r \times N_c = N_{cells} \times N_{xBLOCK\_TI\_MAX}$ by inserting the virtual XFECBLOCK the time interleaving memory and a reading process is achieved as shown in an equation given below.

$$p=0;$$

$$\text{for } i=0; i<N_{cells}N_{xBLOCK\_TI\_MAX}; i=i+1$$

$$\{\text{GENERATE}(R_{n,s,i}, C_{n,s,i}),$$

$$V_i = N_F C_{n,s,i} + R_{n,s,i}$$

$$\text{if } V_i < N_{cells}N_{xBLOCK\_TI}(n,s)$$

$$\{$$

$$Z_{n,s,p} = V_i; p=p+1;$$

$$\}$$

$$\} \quad [\text{Equation 11}]$$

The number of the time interleaving groups is set to 3. An option of the time interleaver is signaled in the PLS2-STAT by DP_TI_TYPE='0', DP_FRAME_INTERVAL='1', and DP_TI_LENGTH='1', that is, NTI=1, IJUMP=1, and PI=1. The number of respective XFECBLOCKs per time interleaving group, of which Ncells=30 is signaled in PLS2-DYN data by NxBLOCK_TI(0,0)=3, NxBLOCK_TI(1,0)=6, and NxBLOCK_TI(2,0)=5 of the respective XFECBLOCKs. The maximum number of XFECBLOCKs is signaled in the PLS2-STAT data by NxBLOCK_Group MAX and this is continued to $\lfloor N_{xBLOCK\_Group\_MAX}/N_{TI} \rfloor = N_{xBLOCK\_TI\_MAX} = 6$.

Figure 28:
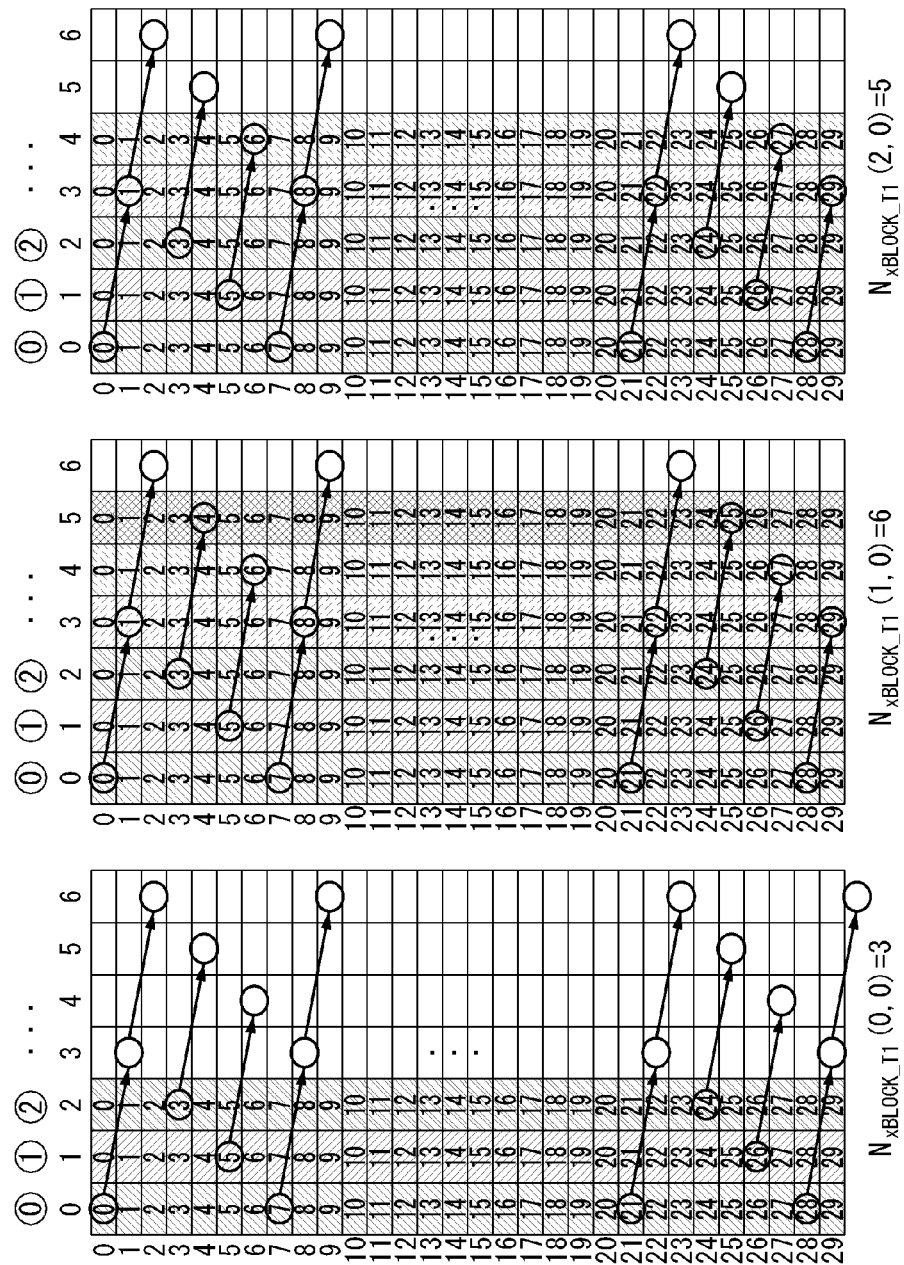
FIG. 28 illustrates a diagonal reading pattern of the twisted row-column block interleaver according to the exemplary embodiment of the present invention.

FIG. 28 illustrates a diagonal reading pattern of the twisted row-column block interleaver according to the exemplary embodiment of the present invention.

In more detail, FIG. 28 illustrates a diagonal reading pattern from respective interleaving arrays having parameters $N_{xBLOCK\_TI\_MAX}=7$ and Sshift=(7-1)/2=3. In this case, during a reading process expressed by a pseudo code given above, when $V_i \geq N_{cells}N_{xBLOCK\_TI}(n,s)$, a value of Vi is omitted and a next calculation value of Vi is used.

Figure 29:
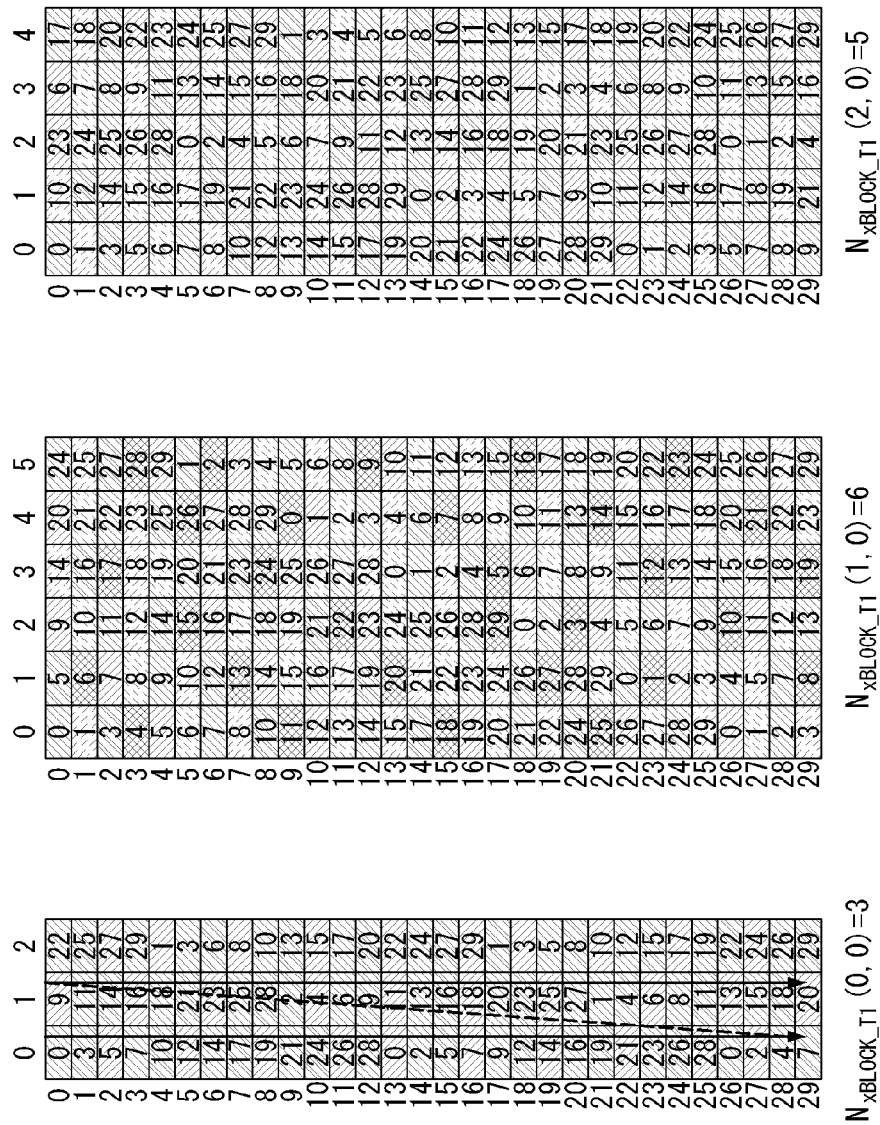
FIG. 29 illustrates XFECBLOCK interleaved from each interleaving array according to an exemplary embodiment of the present invention.

FIG. 29 illustrates XFECBLOCK interleaved from each interleaving array according to an exemplary embodiment of the present invention.

FIG. 29 illustrates XFECBLOCK interleaved from each interleaving array having parameters $N_{xBLOCK\_TI\_MAX}'=7$ and Sshift=3 according to an exemplary embodiment of the present invention.

In what follows, a method for processing signaling information included in a broadcast signal will be described.

As shown in FIG. 1, the signaling generation block 1040 generates physical layer signaling information, and generated signaling information can be transmitted via the BICM unit 1010, frame building unit 1020, and OFDM generation unit 1030. The BICM block processing signaling information may be operated as illustrated in FIGS. 2 and 6. In what follows, operation of a broadcast signal transmitter and a broadcast signal receiver which process signaling information will be further described in more detail.

In this specification, PLS1 information may be called L1-static information, and PLS2 information may be called L1-dynamic information. In other words, signaling information includes information for configuring physical layer parameters, L1 static information with a fixed length, and L1 dynamic information with a variable length. Also, a data pipe may be called a Physical Layer Pipe (PLP).

Figure 30:
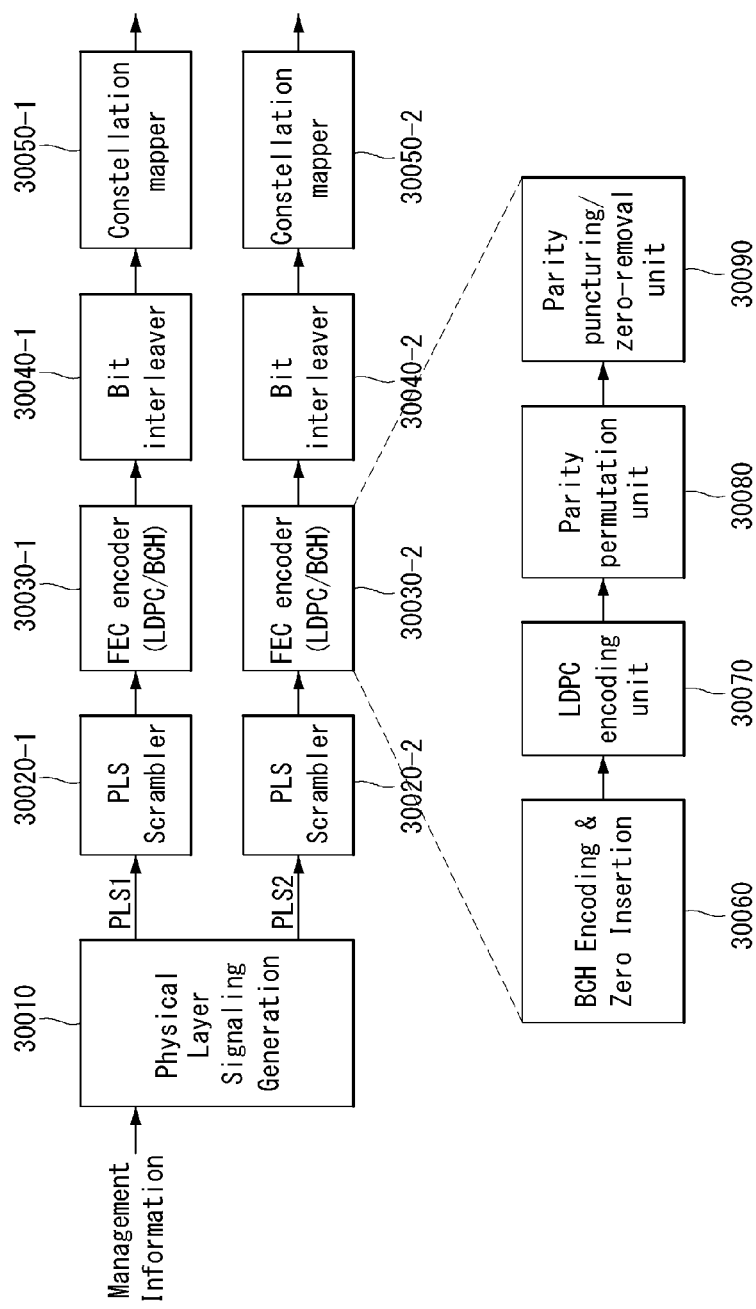
FIG. 30 illustrates building blocks of a broadcast signal transmitter for processing signaling information according to one embodiment of the present invention.

FIG. 30 illustrates building blocks of a broadcast signal transmitter for processing signaling information according to one embodiment of the present invention.

As shown in FIG. 30, a broadcast signal transmitter can comprise a PLS generation unit 30010, a PLS scrambler 30020, an FEC encoder 30030 (shortened/punctured FEC encoder), a bit interleaver 30040, and a constellation mapper 30050. In case the signaling information to be processed is PLS1, the broadcast signal transmitter uses a first PLS scrambler 30020-1, a first FEC encoder 30020-1, a first bit interleaver 30040-1, and a first constellation mapper 30050-1, while, in case the signaling information to be processed is PLS2, the broadcast signal transmitter uses a second PLS scrambler 30020-2, a second FEC encoder 30030-2, a second bit interleaver 30040-2, and a second constellation mapper 30050-2.

FIG. 30 shows the block for processing signaling information as illustrated in FIGS. 1 and 2, and the data processed by the processing blocks of FIG. 30 can be transmitted via the frame building unit 1020 and the OFDM generation unit 1030.

The PLS1 and PLS2 generated by the PLS generation unit can be processed on the basis of FEC encoding units. The PLS1 has a fixed length and can provide information by using a predetermined format within a super frame. The PLS1 can include information for decoding the PLS2. The PLS2 may be divided into PLS2-static information of which the value does not change frame to frame and PLS2-dynamic information of which the value changes. The PLS2 can include information required for decoding a data pipe which transmits a service. As described above, the PLS2-static information or the PLS2-dynamic information may be called L1-dynamic information.

As shown in FIG. 30, the broadcast signal transmitter generates signaling information by using the PLS generation unit 30010 and scrambles signaling information signaling information for data randomization by using the PLS scrambler 30020. The operation of the bit interleaver 30040 and the constellation mapper 30050 follows what is described above. In one embodiment, the bit interleaver 30040 can perform block interleaving and bit demultiplexing, the constellation mapper 30050 can map the data received in bit units into QAM symbols, and QAM may use constellation ranging from BPSK to 256 QAM. The scrambled signaling information can be encoded by FEC encoder units. In case the bit interleaver performs block interleaving and bit demultiplexing, the bit interleaver may be called a bit demultiplexer (demux).

As shown in FIG. 30, the FEC encoder 30030 can further comprise a BCH encoding/zero inserting unit 30060, an LDPC encoding unit 30070 (LDPC encoding/permutation), a parity permutation unit 30080, and a parity puncturing/zero removal unit 30090.

The BCH encoding/zero inserting unit 30060 can perform BCH encoding (shortened systematic BCH encoding) on signaling information and zero insertion/padding to fill up information bits of LDPC encoding. According to one embodiment, the broadcast signal transmitter may perform permutation by taking into account the shortening order in case processed data is PLS1, while, in the case of PLS2, the broadcast signal transmitter may secure shortening performance through column permutation of the LDPC H matrix instead of carrying out the permutation.

The LDPC encoding unit 30070 can perform LDPC encoding on the zero-padded data. The LDPC encoding unit 30070 LDPC encodes K_ldpc LDPC information bits to output N_ldpc data, where (N_ldpc−K_ldpc) LDPC parity bits are added to the output data.

The parity permutation unit 30080 can perform parity interleaving on the LDPC encoded data, output data in units of QC blocks, and permutate the data in units of QC blocks. The QC block may be called a bit group. As described above, the QC block can correspond to a bit group including 360 bits. The parity permutation unit 30080 can output parity interleaved signaling information by permutating the parity interleaved signaling information in units of QC blocks (QCBs). If the QCB units are employed, a receiver system can be easily implemented since the receiver can address parity data in units of QCBs. The parity permutation unit 30080 may be called a parity interleaving/permutation unit 30080.

The parity puncturing/zero removal unit 30090 can perform puncturing on the permutated LDPC parity bits, where punctured bits are not transmitted to the frames which carry signaling information. The parity puncturing/zero removal unit 30090 can remove zero padding bits. The parity puncturing/zero removal unit 30090 can secure code length to be transmitted through parity puncturing and zero removal.

In what follows, the FEC encoder 30030 of FIG. 30 will be described in more detail.

Figure 31:
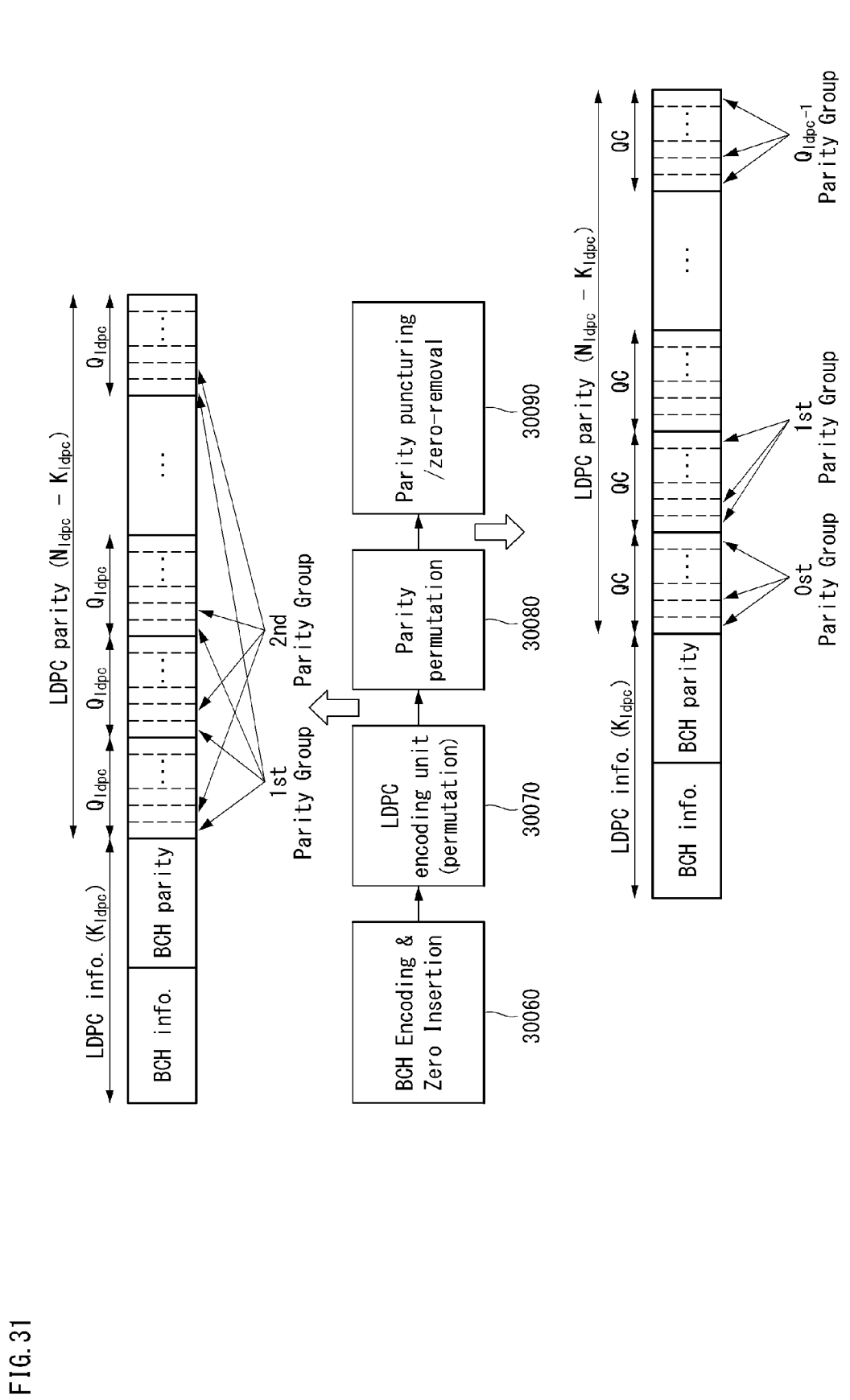
FIG. 31 illustrates an FEC encoding method according to one embodiment of the present invention.

FIG. 31 illustrates an FEC encoding method according to one embodiment of the present invention.

FIG. 31 illustrates operation of the FEC encoder described with reference to FIG. 30 together with a data processing process.

The BCH encoding/zero inserting unit 30060 performs BCH encoding (shortening systematic BCH encoding) on signaling data. Also, the BCH encoding/zero inserting unit 30060 can perform zero insertion or zero padding to fill up the information bits of the LDPC encoding, namely, to make the size of the LDPC encoding data equal the size (K_ldpc) of LDPC information. As one embodiment, zero bit(s) may be inserted to the front of the BCH data information.

The LDPC encoding unit 30070 can carry out LDPC encoding on the zero-padded signaling data. The LDPC encoding unit 30070 LDPC encodes K_ldpc LDPC information bits to output N_ldpc data, where (N_ldpc−K_ldpc) LDPC parity bits are added to the output data.

The parity permutation unit 30080 can perform parity interleaving on the LDPC encoded data to output data in units of QCBs. As shown in FIG. 31, parity interleaved data can be output in 360 bit groups ranging from a 0-th parity group to a (Q_ldpc−1)-th parity group. And the parity permutation unit 30080 can perform parity permutation in units of bit groups according to a predetermined order as described above.

The parity puncturing/zero removal unit 30090 can perform puncturing on the permutated LDPC parity bits, and the punctured bits are not transmitted to the frames which carry signaling information. And the parity puncturing/zero removal unit 30080 can remove zero padding bits. Removal of zero bits can also be performed as described above. The puncturing method can vary according to target performance of the system and a mother code employed. As an example, in case the FEC code rate is 3/15 and performance of −3 dB is aimed, N_punc, which is the number of puncturing bits, can be determined by the equation below.

$$N\_punc = \text{floor}(368/256 \times (K\_bch - K\_sig) + 8060 \quad \text{[Equation 12]}$$

K_sig represents the amount of scrambled data, and K_bch becomes 3072(9*361−168).

Parity puncturing can be performed sequentially from the front part of the parity bits or sequentially in a reserve order from the rear part of the parity bits.

Figure 32:
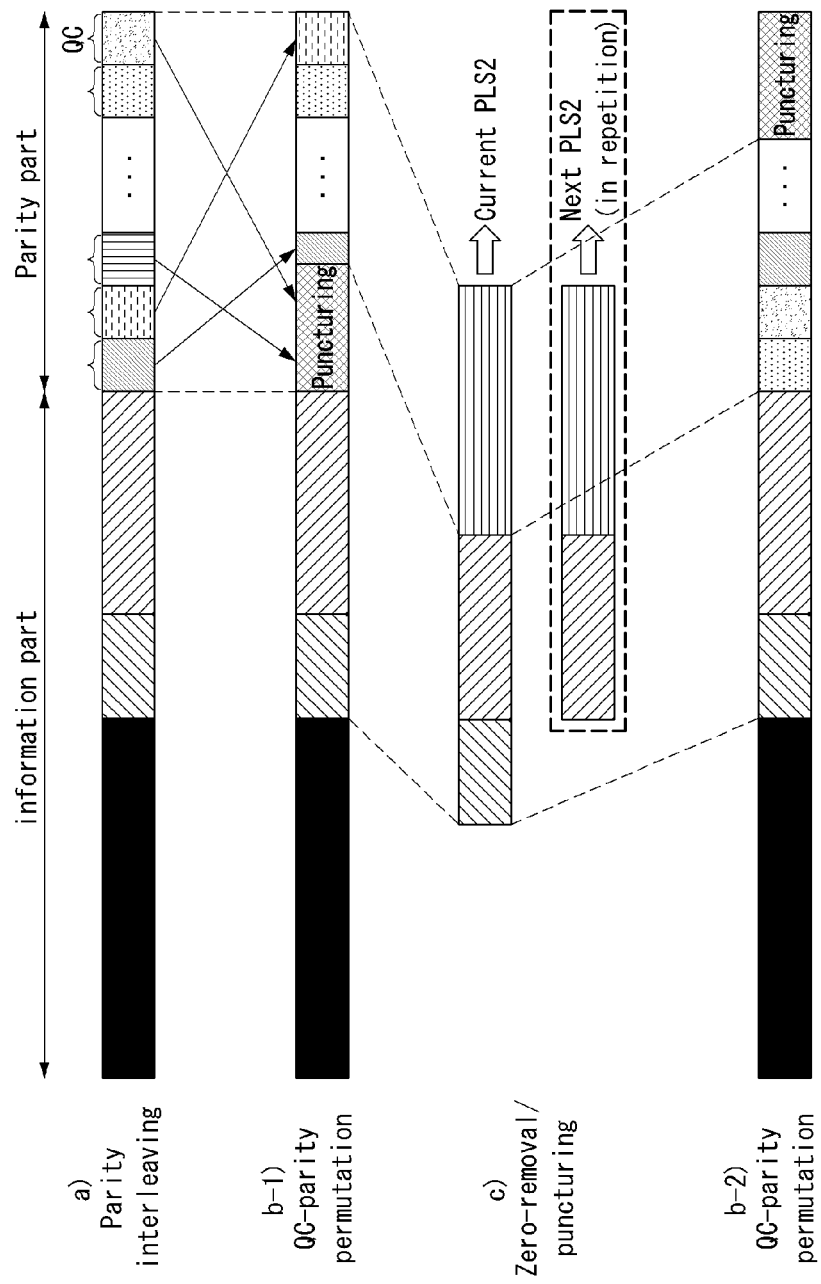
FIG. 32 illustrates an FEC encoding method according to one embodiment of the present invention.

FIG. 32 illustrates an FEC encoding method according to one embodiment of the present invention.

FIG. 32 illustrates a data structure according to parity permutation, parity puncturing, and zero removal, in particular, after parity interleaving in conjunction with FIGS. 30 and 31.

In FIG. 32, (a) represents the data to which parity interleaving has been applied, (b) represents the data to which permutation in units of QC have been applied, and (c) represents the data to which zero removal and puncturing have been applied.

FIG. 32(*a*) shows that the parity part of the data to which parity interleaving has been applied is output in units of QCBs.

FIG. 32(*b*) illustrates that the order of the parity part of FIG. 32(*a*) has been changed through permutation. FIG. 32(*b*-1) illustrates a puncturing method by which parity puncturing is performed sequentially from the front part of permutated parity parts, while FIG. 32(*b*-2) illustrates a puncturing method by which parity puncturing is performed sequentially from the rear part of the permutated parity parts. In other words, in the case of FIG. 32(*b*-2), the permutation order is the reverse of the permutation order of FIG. 32(*b*-1). In case last N_punc bits are punctured starting from the rear part as in FIG. 32(*b*-2), the overall transceiver operation can be simplified. The broadcast signal transmitter can perform permutation according to a puncturing method and in the case of FIG. 32, can perform permutation according to a puncturing order so that bits can be punctured starting from the rear part.

FIG. 32(*c*) illustrates the data part transmitted to the next block after zero removal and puncturing. As one embodiment, part of LDPC encoded signaling information and punctured parity bits may be transmitted being repeated in the next PLS2 frame.

Figure 33:
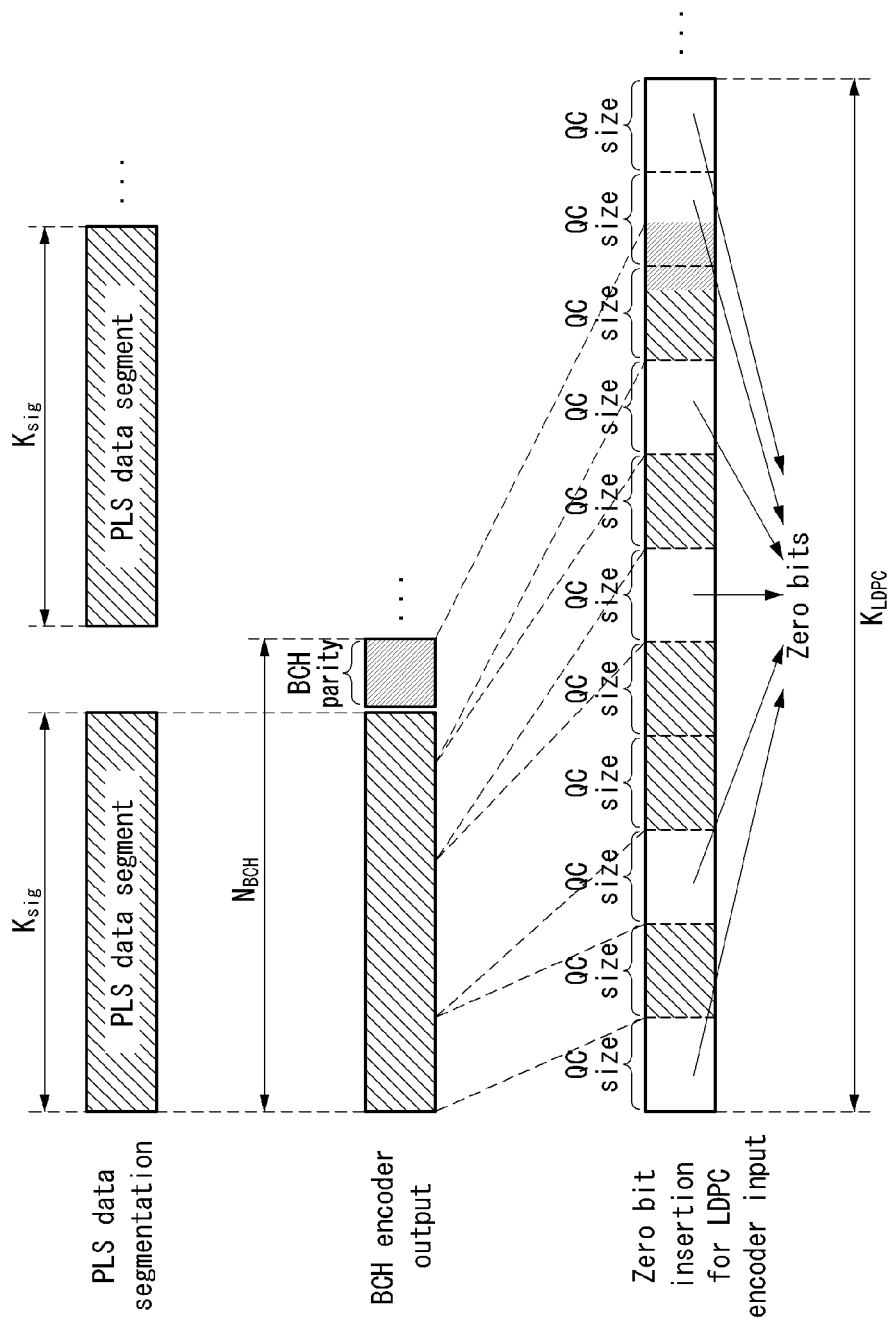
FIG. 33 illustrates a BCH encoding and zero padding method according to one embodiment of the present invention.

FIG. 33 illustrates a BCH encoding and zero padding method according to one embodiment of the present invention.

As shown in FIG. 33, the BCH encoder/zero inserting unit performs BCH encoding on K_sig PLS data segments to output N_BCH (N_BCH=K_sig+B_BCHParity) data. The length of BCH encoded data block, N_bch, can be smaller or equal to the LDPC encoder input length, K_ldpc. In case the length (N_BCH) of BCH encoding data is shorter than the length (K_LDPC) of data for LDPC encoding, the broadcast signal transmitter inserts as many zero bit(s) as the corresponding length disparity (K_ldpc−N_bch) to perform LDPC encoding on the data with a length of K_ldpc. Since the padded zero bit(s) is not transmitted being removed after LDPC encoding, the padded zero bit(s) are used to generate shortened LDPC symbols. Shortening may refer to removal of inserted zero bits, a process of inserting zero bits and removing the zero bits after LDPC encoding, or a process of inserting zero bits.

In view of performance taking account of characteristics of the LDPC symbols, an order of priority exists for positions of padded zero bits, according to which shortening can be applied first or later. The present invention can define the order of priority by K_ldpc/QC size. In other words, the order of priority can be represented by group units obtained by dividing the data to be LDPC encoded by the predetermined number of bit groups (for example, 360). The QC size may correspond to the Quasi-Cyclic size of the LDPC matrix and may correspond to 360 bit size as in the embodiment described above.

As shown in FIG. 33, the broadcast signal transmitter can perform zero insertion subsequent to the BCH encoding by using the BCH encoder/zero inserting unit.

As in FIG. 33, the broadcast signal transmitter can insert as many zero bits as the length of (K_ldpc−N_bch) to particular positions according to the LDPC shortening pattern order. In case (K_ldpc−N_bch) is not a multiple of the QC size, zero bit(s) can be inserted sequentially within the next QC size. In this way, the data of a BCH encoded block can be split and inserted sequentially into the remaining positions except for those positions into which zero bits have been inserted; and input to the LDPC encoder.

In other words, as shown in FIG. 33, the broadcast signal transmitter can calculate the number of groups to be zero-padded by 360 bit group units. For example, if K_ldpc=3240 and K_bch=2000, the number of zero bits to be padded becomes 1240 (=3240−2000), and the number N pad of bit groups required for zero padding becomes 3 (since 1240=360*3+160). Therefore, according to the shortening pattern order, 160 zeros remained after applying zero padding to 3 bit groups can be used for applying zero padding to the next bit group. And the BCH encoded bits (N_bch) can be mapped sequentially to the bit positions to which zeros have not been padded.

FIG. 33 illustrates an embodiment where zero bits are padded to the first, third, sixth, eighth, and eleventh groups according to a shortening pattern order, remaining bits not enough to fill up one group are padded to the tenth group, and BCH encoded bits are mapped sequentially to the remaining positions. In the embodiment of FIG. 33, zeros may be padded first to the front part of the tenth group and the last BCH data part may be placed subsequently.

According to FIG. 33, the structure of the transceiver can be simplified and a data processing rate can be improved by padding zeros at the LDPC input node and performing LDPC shortening without employing a complicated process including the BCH encoding. Also, variable BCH output lengths can be applied to the fixed input of the LDPC encoder.

L1 signaling information includes information essential for decoding data symbols transmitted within a frame. Therefore, decoding delay of L1-FEC is of critical importance to the overall delay of broadcast signal reception. The L1 signaling length required commonly for small PLP is very short. However, in the case of the existing DVB-T2/NGH, a (large) BCH encoding/decoding time period with a fixed length is needed irrespective of the length of L1 signaling information. This is so because zeros are inserted blindly before BCH encoding to ensure the LDPC encoding length. The new structure according to the present invention provides such an advantage that BCH encoding/decoding time period is reduced in proportion as the L1 signaling length (BCH input length) is shortened. (In the case of L1-free, the BCH codeword occupies 7200 bits to perform 200-bit signaling according to an existing method; however, only 368-bit codeword is needed according to an embodiment of the present invention.)

Figure 34:
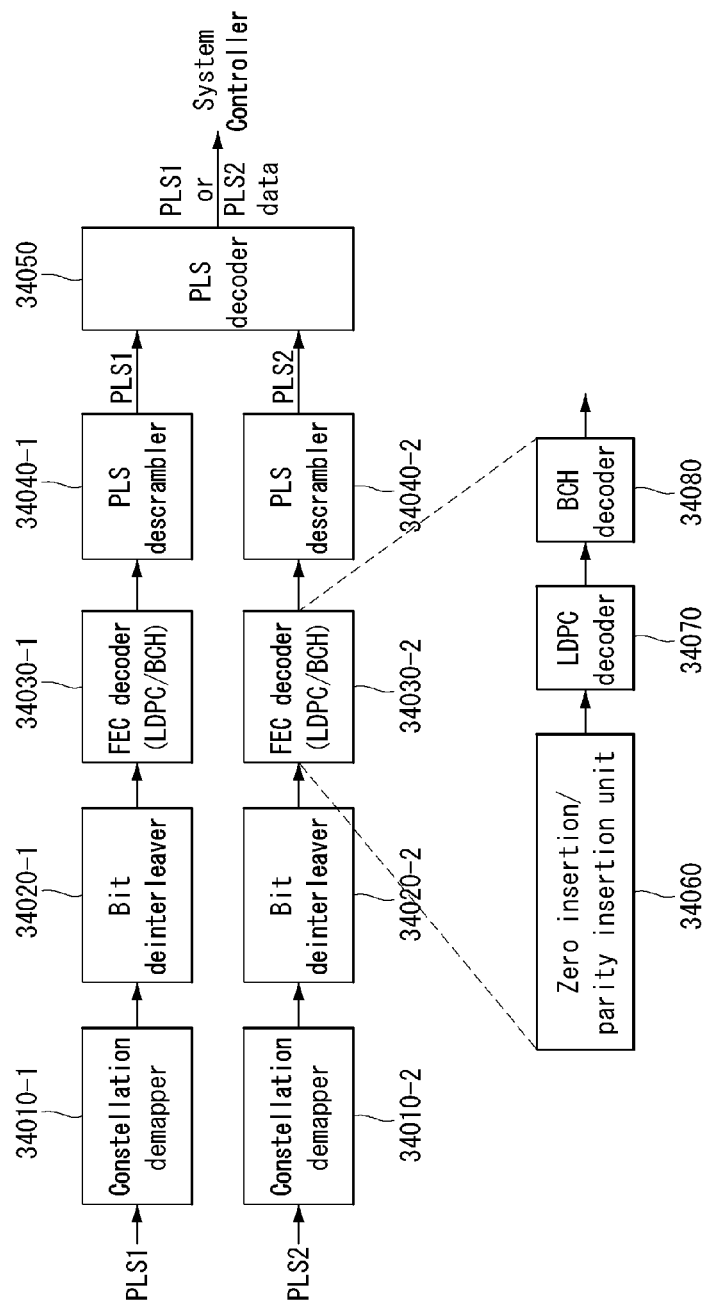
FIG. 34 illustrates building blocks of a broadcast signal receiver for processing signaling information according to one embodiment of the present invention.

FIG. 34 illustrates building blocks of a broadcast signal receiver for processing signaling information according to one embodiment of the present invention.

FIG. 34 describes the demapping/decoding unit and signaling decoding unit of FIG. 8 in more detail. The broadcast signal receiver demodulates a received signal as illustrated in FIG. 9, performs frame parsing, and decodes signaling information through the operation of FIG. 34.

As shown in FIG. 34, the broadcast signal receiver comprises a constellation demapper 34010, a bit deinterleaver 34020, an FEC decoder 34030 (shortened/punctured FEC decoder), a PLS descrambler 34040, and a PLS decoder 34050. The broadcast signal receiver can perform the inverse process of the signal processing method of the broadcast signal transmitter.

In case the signaling information being processed corresponds to PLS1, the broadcast signal receiver can process the signaling information by using a first constellation demapper 34010-1, a first bit deinterleaver 34020-1, a first FEC decoder 34030-1, and a first PLS descrambler 34040-1. In the case of PLS2, the broadcast signal receiver can process the signaling information by using a second constellation demapper 34010-2, a second bit deinterleaver 34020-2, a second FEC decoder 34030-2, and a second PLS descrambler 34040-2. The constellation demapper 34010 can perform constellation demapping on the data of demodulated symbol units. The output data of the constellation demapper 34010, which are LLR values in bit units, can be soft values.

The bit deinterleaver 34020 can perform the inverse process of the bit interleaver of FIG. 30. The bit deinterleaver 34020 performs bit deinterleaving on received data. In other words, the bit deinterleaver 34020 can perform bit multiplexing and block deinterleaving on the received signaling information, which in this case, the bit deinterleaver 34020 may be called a bit multiplexer.

The FEC decoder 34030 can perform FEC decoding, namely, LDPC decoding and BCH decoding on the received data. The FEC decoder 34030 can further comprise three sub-units (zero insertion/parity insertion unit 34060, LDPC decoder 34070, and BCH decoder 34080), of which detailed operations will be described below.

The PLS descrambler 34040 can descramble the received signaling information.

The PLS decoder 34050 can parse/decode signaling information and transmit the decoded data to the system controller. And the system controller can control signal reception and the overall processing operation of the broadcast signal receiver according to the received signaling information.

The zero insertion/parity insertion unit 34060 can insert zero bit(s) removed from the shortening operation of the transmitter side and punctured parity bit(s). In this case, the zero insertion/parity insertion unit 34060 inserts LLRs of infinite value to the positions of zero bits to which the shortening operation has been applied and inserts LLRs of 0 value to the positions of punctured parity bits. Since the values of bits processed by the shortening operation are 0, positive infinite LLR values are inserted thereto; on the other hand, since the punctured parity bits are obtained from decoding, LLR values of 0, which can be 0 or 1, are inserted to the punctured parity bits. As an embodiment, the broadcast signal receiver may perform initialization by inserting infinite LLR values to the information part and 0 LLR values to the parity bits; and for LDPC decoding, may insert bit deinterleaver outputs directly to appropriate positions.

The LDPC decoder 34070 performs LDPC decoding. As an embodiment, the receiver may LDPC decode signaling information by using an LDPC decoder for data.

The BCH decoder 34080 can perform BCH decoding on the LDPC decoded data. The BCH decoder 34080 can perform BCH decoding by extracting the part for BCH decoding from the output of the LDCP decoder 34070. In this case, the BCH decoder 34080 can remove inserted zero bits and perform BCH decoding on the remaining BCH data after the zero removal.

Figure 35:
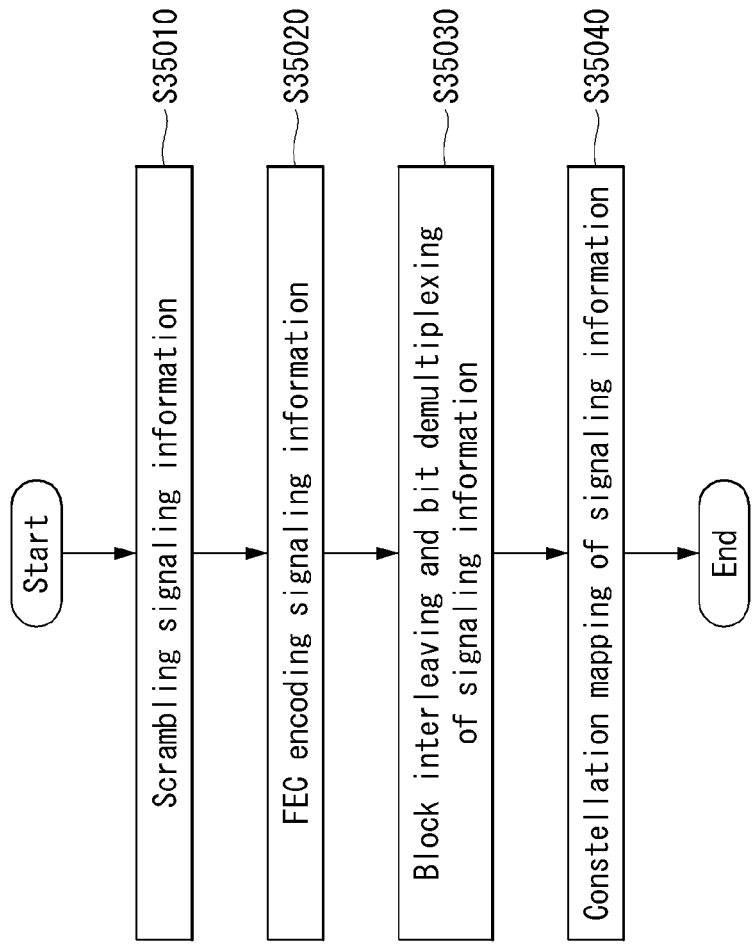
FIG. 35 illustrates a method for processing signaling information included in a broadcast signal of a broadcast signal transmitter according to one embodiment of the present invention.

FIG. 35 illustrates a method for processing signaling information included in a broadcast signal of a broadcast signal transmitter according to one embodiment of the present invention.

The broadcast signal transmitter can scramble signaling information generated from the signaling generation unit by using the scrambler S35010. The broadcast signal transmitter can FEC encode the scrambled signaling information by using the FEC encoder S35020. The broadcast signal transmitter can perform block interleaving and bit demultiplexing of the FEC encoded signaling information by using the bit interleaver S35030. And the broadcast signal transmitter can perform constellation mapping of the signaling information in bit units into data cells/symbols by using the constellation mapper S35040.

In particular, the FEC encoding S35020 of the broadcast signal transmitter according to the present invention can further comprise BCH encoding signaling information by using the BCH encoding/zero inserting unit and inserting zero bits according to the length of BCH encoded signaling information. In this case, the broadcast signal transmitter can pad as many zero bits as the difference when the length of BCH encoded data is shorter than the length of LDPC encoded input data.

The FEC encoding S35020 of the broadcast signal transmitter further comprise LDPC encoding signaling information by using the LDPC encoding unit, where LDPC parity bits are added to the LDPC encoded signaling information.

The FEC encoding S35020 of the broadcast signal transmitter can further comprise interleaving and permutating LDPC parity bits by using the parity permutation unit. The broadcast signal transmitter can split interleaved parity bits into at least one of bit group units and perform permutation on the split bit group units.

The FEC encoding S35020 of the broadcast signal transmitter can further comprise puncturing LDPC parity bits included in the signaling information and removing padded zero bits by using the parity puncturing/zero removal unit. The broadcast signal transmitter may puncture last N_punc parity bits among parity bits in permutated bit group units.

The broadcast signal transmitter can pad zero bits by bit group units according to a shortening pattern order and map/pad BCH encoded signaling information sequentially into the bit positions which are not padded with zero bits.

For a signaling information processing method of the broadcast signal transmitter, the aforementioned method can be used in conjunction with the drawings above.

Figure 36:
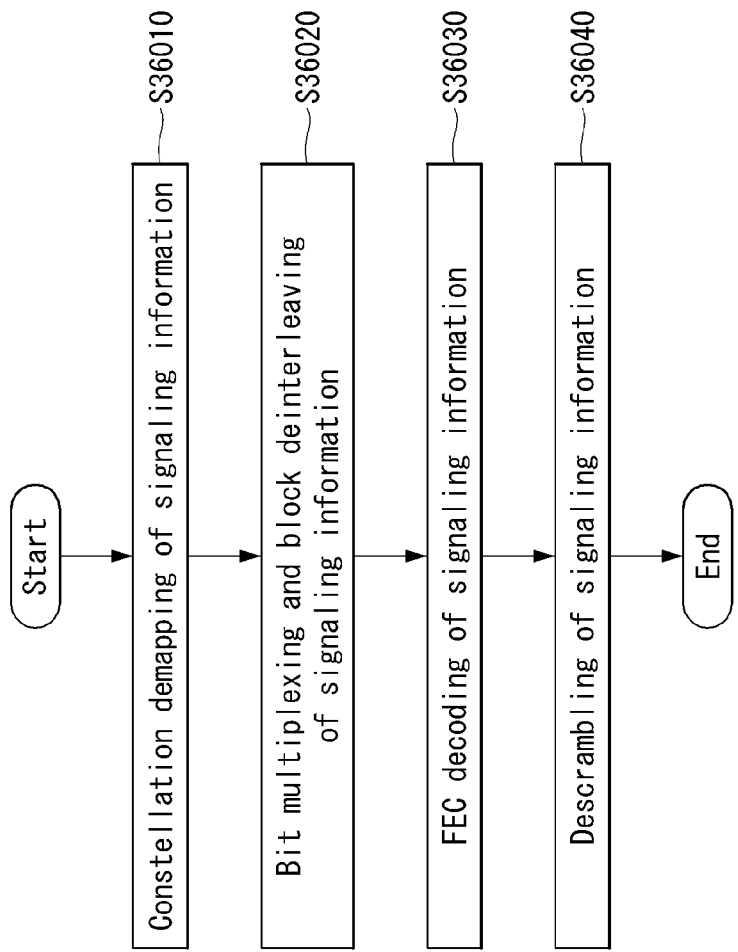
FIG. 36 illustrates a method for processing signaling information included in a broadcast signal of a broadcast signal receiver according to one embodiment of the present invention.

FIG. 36 illustrates a method for processing signaling information included in a broadcast signal of a broadcast signal receiver according to one embodiment of the present invention.

The broadcast signal receiver can perform symbol demapping on the signaling information included in a received broadcast signal into LLR values by using the constellation demapper S36010. The broadcast signal receiver can perform bit multiplexing and block interleaving on the signaling information by using the bit deinterleaver S36020. The broadcast signal receiver can FEC decode the signaling information by using the FEC decoder S36030. And the broadcast signal receiver can descramble the signaling information by using the descrambler S36040.

In particular, the FEC decoding S36030 of a method for processing signaling information according to the present invention further comprises inserting shortened zero bits and punctured parity bits into the signaling information by using the zero insertion and parity insertion unit. In this case, the broadcast signal receiver inserts LLRs of infinite values as the zero bits and LLRs of zero values as the parity bits. Since the punctured parity bits corresponds to the last N_punc parity bits which have been permutated and punctured as described above, the receiver can insert the punctured, last parity bits into the rear part of the signaling information as zero LLR values.

Also, the signaling information included in a received broadcast signal is characterized such that the zero bits are padded in bit group units according to a shortening pattern order and the BCH encoded signaling information is mapped/padded sequentially into the bit positions which are not padded with the zero bits. As described above, the zero bits are padded to fill up the LDPC information bits in case the number of BCH encoded bits is smaller than the number of LDPC information bits, and the signaling information is such kind of information received after the zero bits have been removed.

In a signaling information processing method of the broadcast signal receiver, the method described above in conjunction with the drawings of FIG. 1 to FIG. 35 can be used together in addition to the description with respect to FIG. 36.

The present invention is related to a signaling protection method by using LDPC coding, and this document describes the whole protection process ranging from scrambling to symbol mapping. In particular, zeros can be disposed in the front part of a signal for applying LDPC encoding, or zero padding can be carried out according to a shortening order as shown in FIG. 33. In case zero bits are placed in the front part of a BCH encoded signal, complexity/delay of the encoder/decoder can be reduced by fully utilizing the characteristics of the shortened-BCH codes.

Shortening can reduce complexity in implementation, and secure optimized shortening performance through column permutation of the H-matrix. Also, shortening may be performed sequentially.

Carrying out parity interleaving by taking into account complexity of the receiver, the receiver can carry out LDPC decoding in a QC form, namely, in bit group units.

For parity puncturing, parity permutation can be carried out on the basis of QC units, and puncturing can be carried out from the front or rear part of the parity bits depending on the amount of puncturing.

By employing bit (block) interleaving and bit demultiplexing, reliable mapping can be carried out between the LDPC output and the QAM symbols according to various signaling information lengths. And various constellations that are capable of signaling fitted to mobile, fixed, or high SNR services may be used.

Also, the present invention can perform LDPC shortening by padding zeros at the LDPC input node without undergoing the complex process of BCH encoding, thereby saving the burden of the BCH encoder, improving BCH encoding performance, and reducing system complexity. Also, through this method, varying BCH encoder output can be adapted to the fixed LDPC input length.

The additional delay in signal processing can be reduced only if the receiver is able to quickly decode signaling information. This is so because the BCH decoding latency generated from the receiver-side increases according to the sum of the size of BCH parity bits and the size of zero padding bits. Therefore, as in the present invention, by carrying out zero padding after BCH encoding, the BCH decoding latency at the receiver can be significantly reduced.

It should be clearly understood by those skilled in the art that various modifications and changes of the present invention can be made without leaving the technical principles and scope of the present invention. Therefore, it should be understood that the present invention includes the modifications and changes of the present invention supported by the appended claims and their equivalents.

This document describes all of the apparatus and methods related to the present invention, and descriptions thereof can be applied in a complementary manner.

What is claimed is:

1. A broadcast signal receiver for processing a broadcast signal including signaling information, the broadcast signal receiver comprising:
  a constellation demapper for symbol-demapping the signaling information;
  a bit deinterleaver for bit multiplexing and block deinterleaving the signaling information;
  a forward error correction (FEC) decoder for FEC decoding the signaling information; and
  a descrambler for descrambling the signaling information,
  wherein the FEC decoder further comprises
  a zero inserting/parity inserting unit for inserting values for zero bits and values for parity bits into the signaling information;
  a low-density parity-check (LDPC) decoder for LDPC decoding the signaling information; and
  a Bose-Chaudhuri-Hochquenghem (BCH) decoder for removing the inserted zero bits of the signaling information and BCH decoding the signaling information.

2. The broadcast signal receiver of claim 1, wherein the zero inserting and parity inserting unit inserts infinite LLR values as the values for the zero bits and inserts zero LLR values as the values for the parity bits.

3. The broadcast signal receiver of claim 1, wherein the signaling information includes the parity bits split into at least one bit group and permuted based on a unit of the bit group.

4. The broadcast signal receiver of claim 3, wherein the zero inserting and parity inserting unit inserts the values for the parity bits into the positions of punctured last parity bits.

5. The broadcast signal receiver of claim 1, wherein the signaling information includes the zero bits padded in bit group units according to a shortening pattern order and the BCH encoded signaling information padded sequentially into the bit positions which are not padded with the zero bits.

6. The broadcast signal receiver of claim 1, wherein the values for the zero bits are inserted to fill up LDPC information bits in case the number of BCH encoded bits is smaller than the number of the LDPC information bits.

7. The broadcast signal receiver of claim 1, wherein the signaling information includes information for configuring physical layer parameters, layer 1 (L1) static information with a fixed length, and L1 dynamic information with a variable length.

8. A method for receiving a broadcast signal for processing a broadcast signal including signaling information, the method for receiving a broadcast signal comprising:
symbol-demapping the signaling information;
bit multiplexing and block interleaving the signaling information;
forward error correction (FEC) decoding the signaling information; and
descrambling the signaling information,
wherein the FEC decoding further comprises
inserting values for zero bits and values for parity bits into the signaling information;
low-density parity-check (LDPC) decoding the signaling information; and
removing the inserted zero bits of the signaling information and Bose-Chaudhuri-Hochquenghem (BCH) decoding the signaling information.

9. The method of claim 8, wherein the inserting zero bits and parity bits inserts infinite LLR values as the values for the zero bits and zero LLR values as the values for the parity bits.

10. The method of claim 8, wherein the signalling information includes the parity bits split into at least one bit group and permuted based on a unit of the bit group.

11. The method of claim 10, wherein the values for the parity bits are inserted into the positions of punctured last parity bits.

12. The method of claim 8, wherein the signaling information includes the zero bits padded in bit group units according to a shortening pattern order and the BCH encoded signaling information padded sequentially into the bit positions which are not padded with the zero bits.

13. The method of claim 8, wherein the values for the zero bits are inserted to fill up LDPC information bits in case the number of BCH encoded bits is smaller than the number of the LDPC information bits.

14. The method of claim 8, wherein the signaling information includes information for configuring physical layer parameters, layer 1 (L1) static information with a fixed length, and L1 dynamic information with a variable length.

* * * * *